US008816073B2

(12) United States Patent
Sattigeri et al.

(10) Patent No.: US 8,816,073 B2
(45) Date of Patent: Aug. 26, 2014

(54) MATRIX METALLOPROTEINASE INHIBITORS

(71) Applicant: Ranbaxy Laboratories Limited, New Delhi (IN)

(72) Inventors: Viswajanani J. Sattigeri, Gurgaon (IN); Venkata P. Palle, Pune (IN); Manoj Kumar Khera, Gurgaon (IN); Ranadheer Reddy, Suryapet (IN); Manoj Kumar Tiwari, Mumbai (IN); Ajay Soni, New Delhi (IN); Abdul Rehman Abdul Rauf, Buldane (IN); Sony Joseph, Ernakulam (IN); Arpita Musib, Bankura (IN); Sunanda G. Dastidar, New Delhi (IN); Punit Kumar Sricastava, Guraon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/936,382

(22) Filed: Jul. 8, 2013

(65) Prior Publication Data

US 2013/0295141 A1    Nov. 7, 2013

Related U.S. Application Data

(62) Division of application No. 12/438,182, filed as application No. PCT/IB2007/053340 on Aug. 21, 2007, now Pat. No. 8,507,670.

(30) Foreign Application Priority Data

Aug. 22, 2006  (IN) ............................ 1880/DEL/2006

(51) Int. Cl.
   *C07D 401/06*     (2006.01)
   *C07D 401/14*     (2006.01)
   *A61K 31/53*      (2006.01)
   *A61P 19/02*      (2006.01)

(52) U.S. Cl.
   USPC .......................................... 544/180; 514/241

(58) Field of Classification Search
   USPC ........................................... 544/180; 514/241
   See application file for complete search history.

(56) References Cited

U.S. PATENT DOCUMENTS

| | | | |
|---|---|---|---|
| 3,007,923 A | 11/1961 | Muller et al. ............ 260/239.55 |
| 3,642,896 A | 2/1972 | Collin ........................ 260/570.6 |
| 3,644,353 A | 2/1972 | Lunts et al. ............ 260/247.5 R |
| 3,700,681 A | 10/1972 | Barth ....................... 260/296 AE |
| 3,705,233 A | 12/1972 | Lunts et al. ...................... 424/45 |
| 3,929,768 A | 12/1975 | Brattsand et al. .... 260/239.55 D |
| 3,937,838 A | 2/1976 | Wetterlin et al. .............. 424/311 |
| 3,994,974 A | 11/1976 | Murakami et al. ......... 260/562 A |
| 4,011,258 A | 3/1977 | Wetterlin et al. ......... 260/479 R |
| 4,419,364 A | 12/1983 | Olsson et al. .................. 424/300 |
| 4,992,474 A | 2/1991 | Skidmore et al. ............. 514/653 |
| 5,126,375 A | 6/1992 | Skidmore et al. ............. 514/651 |
| 5,243,076 A | 9/1993 | Skidmore et al. ............. 564/346 |
| 5,399,578 A | 3/1995 | Bühlmayer et al. .......... 514/381 |
| 5,482,934 A | 1/1996 | Calatayud et al. ............ 514/174 |
| 6,350,885 B1 | 2/2002 | O'Brien et al. ............... 549/460 |
| 6,605,604 B1 | 8/2003 | Casara et al. ................. 514/173 |
| 7,601,729 B2 * | 10/2009 | Gaines et al. ................. 514/269 |
| 8,507,670 B2 * | 8/2013 | Sattigeri et al. ............... 544/180 |
| 2008/0194565 A1 * | 8/2008 | Palle et al. ..................... 514/246 |

FOREIGN PATENT DOCUMENTS

| | | | |
|---|---|---|---|
| DE | 1 113 690 | 9/1961 | |
| DE | 2 305 092 | 8/1973 | ............. C07C 91/34 |
| GB | 869511 | 5/1961 | |
| WO | WO 96/15096 | 5/1996 | ............. C07C 59/88 |
| WO | WO 98/09940 | 3/1998 | ............. C07C 251/48 |
| WO | WO 2004/110974 | 12/2004 | ............. C07C 59/48 |
| WO | WO 2004/113279 | 12/2004 | ............. C07C 311/08 |
| WO | WO 2005/026120 | 3/2005 | ........... C07D 209/48 |
| WO | WO 2006/090235 | 8/2006 | ........... C07D 249/18 |

OTHER PUBLICATIONS

Slessor and Tracey, "1,2:5,6-Di-*O*-isopropylidene-D-hexofuranoses and their 3-keto derivatives", *Canadian Journal of Chemistry*, 47:3989-3995 (1969).

Greene, T.Q. and Wuts, P.G.M., 1991. *Protective Groups in Organic Synthesis*. 2nd . Edition. New York: Wiley Interscience Publications.

Hooper, "Families of zinc metalloproteases", *FEBS Letters*, 354:1-6 (1994).

Barron et al., "Synthesis and Antiinflammatory Activity of 4-(*p*-Biphenylyl)-3-hyroxybutyric Acid and Related Compounds", *Journal of Medicinal Chemistry*, 11(6):1139-1144 (1968).

Vartak and Gemeinhart, "Matrix metalloproteases: Underutilized targets for drug delivery", *Journal of Drug Targeting*, 15(1):1-20 (2007).

(Continued)

*Primary Examiner* — Venkataraman Balasubramanian

(57) ABSTRACT

The present invention relates to β-hydroxy and amino-substituted carboxylic acids, which act as matrix metalloproteinase inhibitors, particularly diastereomerically pure β-hydroxy carboxylic acids, corresponding processes for their synthesis, and pharmaceutical compositions containing the compounds of the present invention. Compounds of the present invention are useful in the treatment of various inflammatory, autoimmune, and allergic diseases, such as methods of treating asthma, rheumatoid arthritis, COPD, rhinitis, osteoarthritis, psoriatic arthritis, psoriasis, pulmonary fibrosis, wound healing disorders, pulmonary inflammation, acute respiratory distress syndrome, perodontitis, multiple sclerosis, gingivitis, atherosclerosis, neointimal proliferation, which leads to restenosis and ischemic heart failure, stroke, renal diseases, tumor metastasis, and other inflammatory disorders characterized by the over-expression and over-activation of a matrix metalloproteinase.

3 Claims, No Drawings

(56) References Cited

OTHER PUBLICATIONS

Whittaker et al., "Design and Therapeutic Application of Matrix Metalloproteinase Inhibitors", *Chemical Reviews*, 99(9):2735-2776 (1999).

O'Neil, ed., 2006. Budesonide. *In: The Merck Index: An Encyclopedia of Chemicals, Drugs, and Biologicals*. 14th edition. Merck Research Laboratories, p. 240.

O'Neil, ed., 2006. Ciclesonide. *In: The Merck Index: An Encyclopedia of Chemicals, Drugs, and Biologicals*. 14th edition. Merck Research Laboratories, p. 376.

O'Neil, ed., 2006. Dexamethasone. *In: The Merck Index: An Encyclopedia of Chemicals, Drugs, and Biologicals*. 14th edition. Merck Research Laboratories, p. 500.

O'Neil, ed., 2006. Formoterol. *In: The Merck Index: An Encyclopedia of Chemicals, Drugs, and Biologicals*. 14th edition. Merck Research Laboratories, p. 728.

O'Neil, ed., 2006. Valsartan. *In: The Merck Index: An Encyclopedia of Chemicals, Drugs, and Biologicals*. 14th edition. Merck Research Laboratories, p. 1705.

Rosowsky et al., "*N*-[4-[[(3,4-Dihydro-4-oxo-1,2,3-benzotriazin-6-yl)methyl]amino]benzoyl]-L-glutamic Acid, a Novel A-Ring Analogue of 2-Desamino-5,8-dideazafolic Acid",*Journal of Medicinal Chemistry*, 35(14):2626-2630 (1992).

McKennon et al., "A Convenient Reduction of Amino Acids and Their Derivatives", *Journal of Organic Chemistry*, 58(13):3568-3571 (1993).

Delaunay et al., "Reactivity of β-Amino Alcohols with Carbon Disulfide. Study on the Synthesis of 2-Oxazolidinethiones and 2-Thiazolidinethiones", *Journal of Organic Chemistry*, 60(20):6604-6607 (1995).

McClelland et al., "Kinetics and equilibrium in the ammonolysis of substituted phthalimides", *Canadian Journal of Chemistry*, 63(1):121-128 (1985).

* cited by examiner

MATRIX METALLOPROTEINASE INHIBITORS

FIELD OF THE INVENTION

The present invention relates to certain β-hydroxy- and amino-substituted carboxylic acids as matrix metalloproteinase inhibitors, particularly diastereomerically pure β-hydroxy-carboxylic acids, and to processes for their syntheses.

This invention also relates to pharmacological compositions containing the compounds of the present invention, and methods of treating asthma, rheumatoid arthritis, COPD, rhinitis, osteoarthritis, psoriatic arthritis, psoriasis, pulmonary fibrosis, wound healing disorders, pulmonary inflammation, acute respiratory distress syndrome, perodontitis, multiple sclerosis, gingivitis, atherosclerosis, neointimal proliferation which leads to restenosis and ischemic heart failure, stroke, renal diseases, tumor metastasis, and other inflammatory disorders characterized by the over-expression and over-activation of a matrix metalloproteinase by using said compounds.

BACKGROUND OF THE INVENTION

Matrix metalloproteinases (MMPs) are a naturally occurring superfamily of proteinases (enzymes) found in most mammals. The superfamily is composed of at least 26 members of zinc-containing enzymes produced by many cell types and sharing structural and functional features. Based on structural and functional considerations proteinases have been classified into different families and subfamilies (Vartak et al., *J. Drug Targeting*, 15, 1-20 (2007) and Hooper, *FEBS Letters*, 354, 1-6 (1994)), such as collagenases (MMP-1, -8, and -13), gelatinases (MMP-2 and -9), metalloelastases (MMP-12), the MT-MMPs (MMP-14, -15, -16, -17, -24, and -25), matrilysins (MMP-7 and -26), stromelysins (MMP-3, -10, and -11) and sheddases such as TNF-converting enzymes (TACE and ACE).

Metalloproteinases are believed to be important in physiological disease processes that involve remodeling such as embryonic development, bone formation, and uterine remodeling during menstruation. One major biological function of MMPs is to catalyze the breakdown of connective tissues or extra-cellular matrix by their ability to hydrolyze various components of tissue or matrix. Apart from their role in degrading connective tissue, MMPs are involved in the activation of zymogen (pro) forms of other MMPs, thereby inducing MMP activation. They are also involved in the biosynthesis of TNF-alpha which is implicated in many pathological conditions.

MMP-12, also known as macrophage elastase or metalloelastase, is expressed in activated macrophages and has been shown to be secreted from alveolar macrophages from smokers as well as in foam cells in atherosclerotic lesions. MMP-12 knockout mouse studies have shown the development of significant emphysema, thus supporting its role in COPD. MMP-9 (gelatinase B, 92 kDa type IV collagenase) is one member of the MMP family that is released as a proenzyme and subsequently activated via a protease cascade in vivo.

The concentration of MMP-9 is increased in diseases like asthma, interstitial pulmonary fibrosis (IPF), adult respiratory distress syndrome (ARDS), and chronic obstructive pulmonary disease (COPD). Because of its proteolytic ability, MMP-9 has been implicated in tissue remodelling of the airways and lungs in chronic inflammatory diseases such as severe asthma and COPD. MMP-9 is also likely to be physiologically important because of its ability to regulate the digestion of components of the extracellular matrix as well as the activity of other proteases and cytokines MMP-9 is secreted in neutrophils, macrophages, and osteoclasts, which are easily induced by cytokines and growth factors, and plays a role in various physiological and pathological processes.

Over-expression or over-activation of an MMP or an imbalance between an MMP and a natural (i.e., endogenous) tissue inhibitor of a matrix metalloproteinase (TIMP) has been linked to a pathogenesis of diseases characterized by the breakdown of connective tissue or extracellular matrix.

Inhibition of the activity of one or more MMPs may be of benefit in the treatment of various inflammatory, autoimmune and allergic diseases such as inflammation of the joint, inflammation of the GI tract, inflammation of the skin, collagen remodeling, wound healing disorders, etc.

The design and therapeutic application of MMP inhibitors has revealed that the requirement of a molecule to be an effective inhibitor of MMP class of enzymes is a functional group (e.g., carboxylic acid, hydroxamic acid, or sulphydryl) capable of chelating to the active site $Zn^{2+}$ ion (Whittaker et al., *Chem. Rev.*, 99, 2735-76, (1999)).

WO 2004/110974 discloses compounds and their physiologically functional derivatives described as inhibitors of matrix metalloproteinase enzymes. WO 2004/113279 discloses alleged inhibitors of matrix metalloproteinase. WO 2005/026120 discloses compounds also described as inhibitors of matrix metalloproteinase. U.S. Pat. No. 6,350,885 discloses tricyclic heteroaromatic compounds and their derivatives believed to be inhibitors of matrix metalloproteinases. WO 98/09940 discloses biphenyl butyric acids and their derivatives described as inhibitors of matrix metalloproteinases. *J. Med. Chem.*, Vol. 11(6), 1139-1144 (1968), discloses the synthesis and anti-inflammatory activity of 4-(p-biphenylyl)-3-hydroxybutyric acid and related compounds. WO 96/15096 discloses substituted 4-biarylbutyric or 5-biarylpentanoic acids and derivatives as alleged matrix metalloproteinase inhibitors. WO 2006/090235 describes 5-phenyl-pentanoic acid derivatives described as matrix metalloproteinase inhibitors for the treatment of asthma and other diseases.

Research has been carried out into the identification of inhibitors that are selective, e.g., for a few of the MMP sub-types. An MMP inhibitor of improved selectivity would avoid potential side effects associated with inhibition of MMPs that are not involved in the pathogenesis of the disease being treated.

Further, the use of more selective MMP inhibitors would require administration of a lower amount of the inhibitor for treatment of the disease than would otherwise be required and, after administration, partitioned in vivo among multiple MMPs. Still further, the administration of a lower amount of the compound would improve the margin of safety between the dose of the inhibitor required for therapeutic activity and the dose of the inhibitor at which toxicity is observed.

Many drugs exist as asymmetric three-dimensional molecules, i.e., chiral, and will therefore have several stereoisomers, depending upon the number of chiral centers present. The importance of evaluating new chemical entities having chiral centers as single isomers is to understand their effect on pharmacological and toxicological aspects. There are often pharmacodynamic, pharmacokinetic, and/or toxicological differences between enantiomers/diastereomers. Even if natural physiological mediators are achiral, based on their target environment, their receptors/enzymes may demonstrate a preference for only one optically pure enantiomer of agonists, antagonists, or inhibitors. From a pharmacokinetics point of view, chirality can have an influence on drug absorption, distribution, metabolism, and elimination. Pure single isomers may also offer advantages in terms of these pharmacokinetic parameters, thus enabling better developability of such molecules as drug candidates. It is also known that chirality has a significant effect of the physicochemical properties and crystallinity of a chiral molecule, which in turn have profound effects on the pharmacokinetics and developability of the molecule. Besides those mentioned above, regulatory principles guide one to preferably develop single isomers as drug candidates in order to avoid any pharmacological, pharmacokinetic, and toxicological problems that may arise due to interactions of an unwanted isomer with undesirable molecular targets.

In this context, synthetic strategies to produce pure single isomers offer advantages over analytical techniques of separation of isomers, not only in terms of cost and efficiency but larger amounts of compound can be prepared for elaborate pharmaceutical testing. Thus, compounds of present invention, which are single chiral isomers, have improved potency, improved pharmacokinetics, and/or improved physicochemical properties as compared to racemic compounds.

The present invention is directed to overcoming problems encountered in the art.

SUMMARY OF THE INVENTION

The present invention relates to β-hydroxy and amino substituted carboxylic acids, which act as matrix metalloproteinase inhibitors, particularly diastereomerically pure β-hydroxy carboxylic acids, corresponding processes for the synthesis of and pharmaceutical compositions containing the compounds of the present invention. The present invention relates to matrix metalloproteinase inhibitors useful as effective therapeutic or prophylactic agents in treatment of various inflammatory, autoimmune, and allergic diseases and other inflammatory disorders characterized by the over-expression and over-activation of a matrix metalloproteinase using the compounds.

The present invention relates to compounds that act as dual MMP-9/12 inhibitors, which have desirable activity profiles and beneficial potency, selectivity, and/or pharmacokinetic properties.

The present invention includes new chemical entities having chiral centers as single isomers. Synthetic strategies to produce pure single isomers that offer advantages over analytical techniques of separation of isomers, not only in terms of cost and efficiency, but also a larger amount of the compound can be prepared for elaborate pharmaceutical testing are also provided.

Other aspects will be set forth in the description which follows, and in part will be apparent from the description or may be learned by the practice of the invention.

DETAILED DESCRIPTION OF THE INVENTION

The present invention relates to compounds having the structure of Formula I:

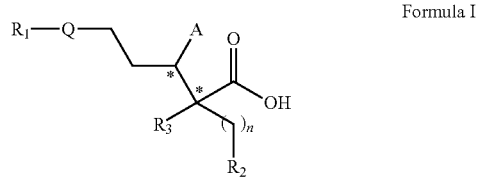

Formula I wherein
* denotes or represents a stereogenic or asymmetric center of defined configuration selected from (R,R), (S,S), (R,S), and (S,R);
n is an integer from 1 to 5;
$R_1$ is hydrogen, optionally substituted alkyl, alkenyl, alkynyl, cycloalkyl, aryl, heterocyclyl, heteroaryl, aralkyl, alkoxy, aryloxy, alkenyloxy or alkynyloxy; and
$R_2$ is heterocyclyl, heteroaryl, $NR_4R_5$, $-NHC(=Y)R_4$, $-NHC(=Y)NR_5R_x$, $-NHC(=O)OR_4$, $-NHSO_2R_4$, $C(=Y)NR_4R_5$, or $C(=O)OR_6$;

wherein
Y is oxygen, sulphur, $OR_5$, $-OC(=O)NR_4R_5$, O-acyl, $S(O)_mR_4$, $-SO_2N(R_4)_2$, cyano, amidino, or guanidine;
$R_x$ is $R_4$ or $-SO_2N(R_4)_2$; and
$R_6$ is hydrogen, alkyl, cycloalkyl, aralkyl, heteroarylalkyl, heterocyclylalkyl, or cycloalkylalkyl;

wherein
$R_4$ is alkyl, alkenyl, alkynyl, cycloalkyl, aryl, heterocyclyl, heteroaryl, aralkyl, heteroarylalkyl, heterocyclylalkyl, or cycloalkylalkyl;
m is an integer from 0 to 2;
$R_5$ is hydrogen or $R_4$;
$R_3$ is hydrogen, fluorine, alkyl, cycloalkylalkyl, or aralkyl;
A is OH, $OR_4$, $-OC(=O)NR_4R_5$, O-acyl, $NH_2$, $NR_4R_5$, $-NHC(=Y)R_4$, $-NHC(=Y)NR_5R_x$, $-NHC(=O)OR_4$, or $-NHSO_2R_4$; and
Q is optionally substituted aryl or heteroaryl.

Compounds of Formula I have particularly advantageous properties, which may include biological activities, such as modelling of LPS-included rat neutrophilia, selective inhibition of MMP-9 and MMP-12 activity, and inhibition of these activities without selectivity towards MMP-1 activity. Further, these advantageous properties may include solubilities which enhance preparation and administration of dosage forms, and improved bioavailability, as compared to known compounds, for example, those of WO 2005/026120.

In one embodiment, the invention relates to compounds of general Formula Ia,

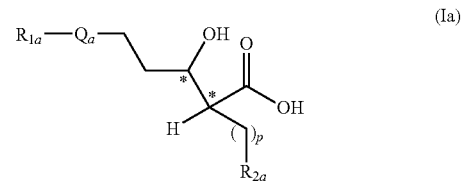

(Ia)

wherein
* denotes or represents a stereogenic or asymmetric center of defined configuration selected from (R,R), (S,S), (R,S), and (S,R);
p is an integer from 1 to 3;
$R_{1a}$ is an optionally substituted aryl or heteroaryl;
$R_{2a}$ is a 5-6 membered N-containing heterocyclyl linked through N atom, which is optionally fused to aryl or heteroaryl, or spirofused to cycloalkyl, which can optionally be further substituted with one or more oxo groups, alkyl, cycloalkyl, halo, alkoxy, trifluoroalkyl, or aryl; and
$Q_a$ is an optionally substituted 5 or 6 membered heteroaryl containing 1 to 3 heteroatoms selected from O, N, or S.

Compounds of Formula Ia have particularly advantageous properties, which may include biological activities, such as modelling of LPS-included rat neutrophilia, selective inhibition of MMP-9 and MMP-12 activity, and inhibition of these activities without selectivity towards MMP-1 activity. Further, these advantageous properties may include solubilities which enhance preparation and administration of dosage forms, and improved bioavailability, as compared to known compounds, for example, those of WO 2005/026120.

In another embodiment, the invention relates to compounds of general Formula Ib,

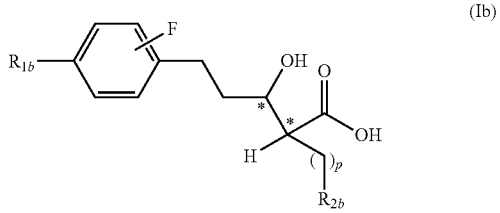

wherein
* denotes or represents a stereogenic or asymmetric center of defined configuration selected from (R,R), (S,S), (R,S), and (S,R);
p is an integer from 1 to 3;
$R_{1b}$ is an optionally substituted phenyl or heteroaryl wherein optional substituents can be selected from one or more of alkyl, cycloalkyl, halo, alkoxy, trifluoroalkyl, or aryl; and
$R_{2b}$ is a 5-6 membered N-containing heterocyclyl linked through N atom, which is optionally fused to aryl or heteroaryl, or spirofused to cycloalkyl, which can optionally be further substituted with one or more oxo group, alkyl, cycloalkyl, halo, alkoxy, trifluoroalkyl, or aryl.

Compounds of Formula Ib have particularly advantageous properties, which may include biological activities, such as modelling of LPS-included rat neutrophilia, selective inhibition of MMP-9 and MMP-12 activity, and inhibition of these activities without selectivity towards MMP-1 activity. Further, these advantageous properties may include solubilities which enhance preparation and administration of dosage forms, and improved bioavailability, as compared to known compounds, for example, those of WO 2005/026120.

In another embodiment, the invention relates to compounds of general Formula Ic,

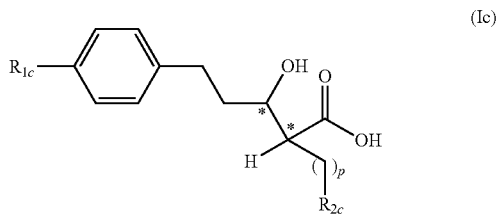

wherein
* denotes or represents a stereogenic or asymmetric center of defined configuration selected from (R,R), (S,S), (R,S), and (S,R);
p is an integer from 1 to 3;
$R_{1c}$ is optionally substituted phenyl, pyridyl, pyrimidyl, thienyl, or pyrazolyl; wherein optional substitutent can be selected from with one or more alkyl, halo, alkoxy, trifluoroalkyl, or aryl; and
$R_{2c}$ is a 5-6 membered N-containing heterocyclyl linked through N atom, which is optionally fused to aryl or heteroaryl, or spirofused to cycloalkyl, which can optionally be further substituted with one or more oxo group, alkyl, cycloalkyl, halo, alkoxy, trifluoroalkyl, or aryl.

In compounds of Formula Ic, $R_{2c}$ represents 5-6 membered N-containing heterocyclyl linked through N atom, which is optionally fused to aryl or heteroaryl, or spirofused to cycloalkyl, for example, benzotriazinone, isoindoledione, pyrimidinedione, aza-spiro[4.5]decanedione, benzo-oxazinedione, imidazolidinedione, or phthalazinone.

Compounds of Formula Ic have particularly advantageous properties, which may include biological activities, such as modelling of LPS-included rat neutrophilia, selective inhibition of MMP-9 and MMP-12 activity, and inhibition of these activities without selectivity towards MMP-1 activity. Further, these advantageous properties may include solubilities which enhance preparation and administration of dosage forms, and improved bioavailability, as compared to known compounds, for example, those of WO 2005/026120.

The diastereomers, rotational isomers, N-oxides, polymorphs, pharmaceutically acceptable salts and pharmaceutically acceptable solvates of these compounds, prodrugs, and metabolites having the same type of activity are also provided, as well as pharmaceutical compositions comprising the compounds, their metabolites, diastereomers, conformational isomers, N-oxides, polymorphs, solvates, or pharmaceutically acceptable salts thereof, in combination with a pharmaceutically acceptable carrier and optionally included excipients.

In one embodiment, the invention encompasses compounds of Formula (I), which may include, but are not limited to, the following, for example,
(2S,3R)-3-hydroxy-2-[2-(4-oxo-1,2,3-benzotriazin-3(4H)-yl)ethyl]-5-(4-pyrimidin-5-ylphenyl)pentanoic acid (Compound No. 1);
(2S,3R)-2-[2-(5-tert-butyl-1,3-dioxo-1,3-dihydro-2H-isoindol-2-yl)ethyl]-3-hydroxy-5-[4-(6-methoxypyridin-3-yl)phenyl]pentanoic acid (Compound No. 2);
(2S,3R)-2-[2-(1,3-dioxo-1,3-dihydro-2H-isoindol-2-yl)ethyl]-3-hydroxy-5-[4-(6-methylpyridin-3-yl)phenyl]pentanoic acid (Compound No. 3);
(2S,3R)-2-[2-(1,3-dioxo-1,3-dihydro-2H-isoindol-2-yl)ethyl]-5-(4'-fluorobiphenyl-4-yl)-3-hydroxypentanoic acid (Compound No. 4);
(2S,3R)-5-(3',4'-difluorobiphenyl-4-yl)-2-[2-(1,3-dioxo-1,3-dihydro-2H-isoindol-2-yl)ethyl]-3-hydroxypentanoic acid (Compound No. 5);
(2S,3R)-3-hydroxy-5-[4-(6-methylpyridin-3-yl)phenyl]-2-[2-(4-oxo-1,2,3-benzotriazin-3(4H)-yl)ethyl]pentanoic acid (Compound No. 6);
(2S,3R)-3-hydroxy-2-[2-(5-methyl-1,3-dioxo-1,3-dihydro-2H-isoindol-2-yl)ethyl]-5-[4-(6-methylpyridin-3-yl)phenyl]pentanoic acid (Compound No. 7);
(2S,3R)-5-(4'-fluorobiphenyl-4-yl)-3-hydroxy-2-[2-(5-methyl-1,3-dioxo-1,3-dihydro-2H-isoindol-2-yl)ethyl]pentanoic acid (Compound No. 8);
(2S,3R)-5-(4'-fluorobiphenyl-4-yl)-3-hydroxy-2-[2-(4-oxo-1,2,3-benzotriazin-3(4H)-yl)ethyl]pentanoic acid (Compound No. 9);
(2S,3R)-3-hydroxy-5-(4'-methoxybiphenyl-4-yl)-2-[2-(4-oxo-1,2,3-benzotriazin-3(4H)-yl)ethyl]pentanoic acid (Compound No. 10);
(2S,3R)-5-(3',4'-difluorobiphenyl-4-yl)-3-hydroxy-2-[2-(5-methyl-1,3-dioxo-1,3-dihydro-2H-isoindol-2-yl)ethyl]pentanoic acid (Compound No. 11);

(2S,3R)-5-(3',4'-difluorobiphenyl-4-yl)-3-hydroxy-2-[2-(4-oxo-1,2,3-benzotriazin-3(4H)-yl)ethyl]pentanoic acid (Compound No. 12);

(2S,3R)-2-[2-(1,3-dioxo-1,3-dihydro-2H-isoindol-2-yl)ethyl]-3-hydroxy-5-(4'-methoxybiphenyl-4-yl)pentanoic acid (Compound No. 13);

(2S,3R)-2-[2-(1,3-dioxo-1,3-dihydro-2H-isoindol-2-yl)ethyl]-3-hydroxy-5-[4'-(trifluoromethoxy)biphenyl-4-yl]pentanoic acid (Compound No. 14);

(2S,3R)-5-(4'-chloro-3'-fluorobiphenyl-4-yl)-3-hydroxy-2-[2-(4-oxo-1,2,3-benzotriazin-3(4H)-yl)ethyl]pentanoic acid (Compound No. 15);

(2S,3R)-2-[2-(5-tert-butyl-1,3-dioxo-1,3-dihydro-2H-isoindol-2-yl)ethyl]-5-(3',4'-difluorobiphenyl-4-yl)-3-hydroxypentanoic acid (Compound No. 16);

(2S,3R)-2-[2-(5-tert-butyl-1,3-dioxo-1,3-dihydro-2H-isoindol-2-yl)ethyl]-3-hydroxy-5-(4'-methoxybiphenyl-4-yl)pentanoic acid (Compound No. 17);

(2S,3R)-3-hydroxy-2-[2-(4-oxo-1,2,3-benzotriazin-3(4H)-yl)ethyl]-5-[4'-(trifluoromethyl)biphenyl-4-yl]pentanoic acid (Compound No. 18);

(2S,3R)-2-[2-(5-tert-butyl-1,3-dioxo-1,3-dihydro-2H-isoindol-2-yl)ethyl]-5-(4'-fluorobiphenyl-4-yl)-3-hydroxypentanoic acid (Compound No. 19);

(2S,3R)-2-[2-(5-tert-butyl-1,3-dioxo-1,3-dihydro-2H-isoindol-2-yl)ethyl]-5-(4'-chlorobiphenyl-4-yl)-3-hydroxypentanoic acid (Compound No. 20);

(2S,3R)-2-[2-(1,3-dioxo-1,3-dihydro-2H-isoindol-2-yl)ethyl]-3-hydroxy-5-[4'-(trifluoromethyl)biphenyl-4-yl]pentanoic acid (Compound No. 21);

(2S,3R)-2-[2-(1,3-dioxo-1,3-dihydro-2H-isoindol-2-yl)ethyl]-3-hydroxy-5-(4'-methylbiphenyl-4-yl)pentanoic acid (Compound No. 22);

(2S,3R)-2-[2-(1,3-dioxo-1,3-dihydro-2H-isoindol-2-yl)ethyl]-5-(3'-fluoro-4'-methoxybiphenyl-4-yl)-3-hydroxypentanoic acid (Compound No. 23);

(2S,3R)-3-hydroxy-5-[4-(6-methoxypyridin-3-yl)phenyl]-2-[2-(5-methyl-1,3-dioxo-1,3-dihydro-2H-isoindol-2-yl)ethyl]pentanoic acid (Compound No. 24);

(2S,3R)-3-hydroxy-5-(4'-methylbiphenyl-4-yl)-2-[2-(4-oxo-1,2,3-benzotriazin-3(4H)-yl)ethyl]pentanoic acid (Compound No. 25);

(2S,3R)-5-(4'-ethylbiphenyl-4-yl)-3-hydroxy-2-[2-(4-oxo-1,2,3-benzotriazin-3(4H)-yl)ethyl]pentanoic acid (Compound No. 26);

(2S,3R)-5-(4'-chlorobiphenyl-4-yl)-3-hydroxy-2-[2-(5-methyl-1,3-dioxo-1,3-dihydro-2H-isoindol-2-yl)ethyl]pentanoic acid (Compound No. 27);

(2S,3R)-5-(4'-chlorobiphenyl-4-yl)-3-hydroxy-2-[2-(4-oxo-1,2,3-benzotriazin-3(4H)-yl)ethyl]pentanoic acid (Compound No. 28);

(2S,3R)-2-[2-(1,3-dioxo-1,3-dihydro-2H-isoindol-2-yl)ethyl]-3-hydroxy-5-(4-pyrimidin-5-ylphenyl)pentanoic acid (Compound No. 29);

(2S,3R)-2-[2-(1,3-dioxo-1,3-dihydro-2H-isoindol-2-yl)ethyl]-3-hydroxy-5-[4-(1-methyl-1H-pyrazol-4-yl)phenyl]pentanoic acid (Compound No. 30);

(2S,3R)-2-[2-(1,3-dioxo-1,3-dihydro-2H-isoindol-2-yl)ethyl]-3-hydroxy-5-(4-pyridin-3-ylphenyl)pentanoic acid (Compound No. 31);

(2S,3R)-5-[4-(2,3-dihydro-1,4-benzodioxin-6-yl)phenyl]-3-hydroxy-2-[2-(4-oxo-1,2,3-benzotriazin-3(4H)-yl)ethyl]pentanoic acid (Compound No. 32);

(2S,3R)-3-hydroxy-5-[4-(6-methoxypyridin-3-yl)phenyl]-2-[2-(8-methyl-4-oxo-1,2,3-benzotriazin-3(4H)-yl)ethyl]pentanoic acid (Compound No. 33);

(2S,3R)-3-hydroxy-2-[2-(8-methyl-4-oxo-1,2,3-benzotriazin-3(4H)-yl)ethyl]-5-[4-(6-methylpyridin-3-yl)phenyl]pentanoic acid (Compound No. 34);

(2S,3R)-3-hydroxy-5-[4-(1-methyl-1H-pyrazol-4-yl)phenyl]-2-[2-(4-oxo-1,2,3-benzotriazin-3(4H)-yl)ethyl]pentanoic acid (Compound No. 35);

(2S,3R)-3-hydroxy-2-[2-(8-methoxy-4-oxo-1,2,3-benzotriazin-3(4H)-yl)ethyl]-5-[4-(6-methoxypyridin-3-yl)phenyl]pentanoic acid (Compound No. 36);

(2S,3R)-2-[2-(7-chloro-4-oxo-1,2,3-benzotriazin-3(4H)-yl)ethyl]-3-hydroxy-5-[4-(6-methoxypyridin-3-yl)phenyl]pentanoic acid (Compound No. 37);

(2S,3R)-3-hydroxy-2-{2-[7-(6-methoxypyridin-3-yl)-4-oxo-1,2,3-benzotriazin-3(4H)-yl]ethyl}-5-[4-(6-methoxypyridin-3-yl)phenyl]pentanoic acid (Compound No. 38);

(2S,3R)-2-[2-(6,7-difluoro-4-oxo-1,2,3-benzotriazin-3(4H)-yl)ethyl]-3-hydroxy-5-[4-(6-methoxypyridin-3-yl)phenyl]pentanoic acid (Compound No. 39);

(2S,3R)-2-[2-(5-fluoro-4-oxo-1,2,3-benzotriazin-3(4H)-yl)ethyl]-3-hydroxy-5-[4-(6-methoxypyridin-3-yl)phenyl]pentanoic acid (Compound No. 40);

(2S,3R)-3-hydroxy-2-[2-(8-methoxy-4-oxo-1,2,3-benzotriazin-3(4H)-yl)ethyl]-5-[4-(6-methylpyridin-3-yl)phenyl]pentanoic acid (Compound No. 41);

(2S,3R)-3-hydroxy-2-{2-[5-(6-methoxypyridin-3-yl)-4-oxo-1,2,3-benzotriazin-3(4H)-yl]ethyl}-5-[4-(6-methoxypyridin-3-yl)phenyl]pentanoic acid (Compound No. 42);

(2S,3R)-5-(4'-chloro-3'-fluorobiphenyl-4-yl)-2-[2-(1,3-dioxo-1,3-dihydro-2H-isoindol-2-yl)ethyl]-3-hydroxypentanoic acid (Compound No. 43);

(2S,3R)-2-[2-(1,3-dioxo-1,3-dihydro-2H-isoindol-2-yl)ethyl]-3-hydroxy-5-[4-(1-isobutyl-1H-pyrazol-4-yl)phenyl]pentanoic acid (Compound No. 44);

(2S,3R)-5-biphenyl-4-yl-2-[2-(1,3-dioxo-1,3-dihydro-2H-isoindol-2-yl)ethyl]-3-hydroxypentanoic acid (Compound No. 45);

(2S,3R)-2-[2-(1,3-dioxo-1,3-dihydro-2H-isoindol-2-yl)ethyl]-5-(3'-fluoro-4'-methylbiphenyl-4-yl)-3-hydroxypentanoic acid (Compound No. 46);

(2S,3R)-5-(3,3'-difluoro-4'-methoxybiphenyl-4-yl)-2-[2-(1,3-dioxo-1,3-dihydro-2H-isoindol-2-yl)ethyl]-3-hydroxypentanoic acid (Compound No. 47);

(2S,3R)-5-[4-(2,3-dihydro-1,4-benzodioxin-6-yl)phenyl]-2-[2-(1,3-dioxo-1,3-dihydro-2H-isoindol-2-yl)ethyl]-3-hydroxypentanoic acid (Compound No. 48);

(2S,3R)-2-[2-(1,3-dioxo-1,3-dihydro-2H-isoindol-2-yl)ethyl]-3-hydroxy-5-[4-(1H-tetrazol-1-yl)phenyl]pentanoic acid (Compound No. 49);

(2S,3R)-2-[2-(1,3-dioxo-1,3-dihydro-2H-isoindol-2-yl)ethyl]-5-[2-fluoro-4-(6-methoxypyridin-3-yl)phenyl]-3-hydroxypentanoic acid (Compound No. 50);

(2S,3R)-5-(3'-fluoro-4'-methylbiphenyl-4-yl)-3-hydroxy-2-[2-(4-oxo-1,2,3-benzotriazin-3(4H)-yl)ethyl]pentanoic acid (Compound No. 51);

(2S,3R)-3-hydroxy-5-[4-(1-isobutyl-1H-pyrazol-4-yl)phenyl]-2-[2-(4-oxo-1,2,3-benzotriazin-3(4H)-yl)ethyl]pentanoic acid (Compound No. 52);

(2S,3R)-5-biphenyl-4-yl-3-hydroxy-2-[2-(4-oxo-1,2,3-benzotriazin-3(4H)-yl)ethyl]pentanoic acid (Compound No. 53);

(2S,3R)-3-hydroxy-5-[4-(6-methoxypyridin-3-yl)phenyl]-2-[2-(7-methyl-4-oxo-1,2,3-benzotriazin-3(4H)-yl)ethyl]pentanoic acid (Compound No. 54);

(2S,3R)-2-[2-(1,3-dioxo-1,3-dihydro-2H-isoindol-2-yl)ethyl]-5-[6-(3-fluoro-4-methoxyphenyl)pyridin-3-yl]-3-hydroxypentanoic acid (Compound No. 55);

(2S,3R)-5-(4'-chloro-3-fluorobiphenyl-4-yl)-2-[2-(1,3-dioxo-1,3-dihydro-2H-isoindol-2-yl)ethyl]-3-hydroxypentanoic acid (Compound No. 56);

(2S,3R)-2-[2-(1,3-dioxo-1,3-dihydro-2H-isoindol-2-yl)ethyl]-3-hydroxy-5-[6-(4-methoxyphenyl)pyridin-3-yl]pentanoic acid (Compound No. 57);

(2S,3R)-2-[2-(1,3-dioxo-1,3-dihydro-2H-isoindol-2-yl)ethyl]-5-(3-fluoro-4'-methoxybiphenyl-4-yl)-3-hydroxypentanoic acid (Compound No. 58);

(2S,3R)-5-[6-(4-chlorophenyl)pyridin-3-yl]-2-[2-(1,3-dioxo-1,3-dihydro-2H-isoindol-2-yl)ethyl]-3-hydroxypentanoic acid (Compound No. 59);

(2S,3R)-2-[2-(1,3-dioxo-1,3-dihydro-2H-isoindol-2-yl)ethyl]-3-hydroxy-5-(6'-methoxy-2,3'-bipyridin-5-yl)pentanoic acid (Compound No. 60);

(2S,3R)-5-[4-(4-chlorophenyl)-2-thienyl]-2-[2-(1,3-dioxo-1,3-dihydro-2H-isoindol-2-yl)ethyl]-3-hydroxypentanoic acid (Compound No. 61);

(2S,3R)-2-[2-(1,3-dioxo-1,3-dihydro-2H-isoindol-2-yl)ethyl]-3-hydroxy-5-[4-(6-methoxypyridin-3-yl)-2-thienyl]pentanoic acid (Compound No. 62);

(2S,3R)-2-[2-(1,3-dioxo-1,3-dihydro-2H-isoindol-2-yl)ethyl]-3-hydroxy-5-{4-[4-(trifluoromethyl)phenyl]-2-thienyl}pentanoic acid (Compound No. 63);

(2S,3R)-2-[2-(1,3-dioxo-1,3-dihydro-2H-isoindol-2-yl)ethyl]-5-[4-(3-fluoro-4-methoxyphenyl)-2-thienyl]-3-hydroxypentanoic acid (Compound No. 64);

(2S,3R)-3-hydroxy-2-[2-(7-methyl-4-oxo-1,2,3-benzotriazin-3(4H)-yl)ethyl]-5-[4'-(trifluoromethyl)biphenyl-4-yl]pentanoic acid (Compound No. 65);

(2S,3R)-3-hydroxy-2-[2-(6-methyl-4-oxo-1,2,3-benzotriazin-3(4H)-yl)ethyl]-5-[4'-(trifluoromethyl)biphenyl-4-yl]pentanoic acid (Compound No. 66);

(2S,3R)-2-[2-(7-chloro-4-oxo-1,2,3-benzotriazin-3(4H)-yl)ethyl]-3-hydroxy-5-(4'-methylbiphenyl-4-yl)pentanoic acid (Compound No. 67);

(2S,3R)-3-hydroxy-2-[2-(8-methoxy-4-oxo-1,2,3-benzotriazin-3(4H)-yl)ethyl]-5-[4'-(trifluoromethyl)biphenyl-4-yl]pentanoic acid (Compound No. 68);

(2S,3R)-2-[2-(6,7-difluoro-4-oxo-1,2,3-benzotriazin-3(4H)-yl)ethyl]-3-hydroxy-5-[4'-(trifluoromethyl)biphenyl-4-yl]pentanoic acid (Compound No. 69);

(2S,3R)-2-[2-(1,3-dioxo-1,3-dihydro-2H-isoindol-2-yl)ethyl]-5-[2-fluoro-5-(6-methoxypyridin-3-yl)phenyl]-3-hydroxypentanoic acid (Compound No. 70);

(2S,3R)-5-(4'-chloro-4-fluorobiphenyl-3-yl)-2-[2-(1,3-dioxo-1,3-dihydro-2H-isoindol-2-yl)ethyl]-3-hydroxypentanoic acid (Compound No. 71);

(2S,3R)-2-[2-(1,3-dioxo-1,3-dihydro-2H-isoindol-2-yl)ethyl]-5-[6-fluoro-4'-(trifluoromethyl)biphenyl-3-yl]-3-hydroxypentanoic acid (Compound No. 72);

(2S,3R)-2-[2-(1,3-dioxo-1,3-dihydro-2H-isoindol-2-yl)ethyl]-5-[4-fluoro-3-(6-methoxypyridin-3-yl)phenyl]-3-hydroxypentanoic acid (Compound No. 73);

(2S,3R)-5-(4'-chloro-6-fluorobiphenyl-3-yl)-2-[2-(1,3-dioxo-1,3-dihydro-2H-isoindol-2-yl)ethyl]-3-hydroxypentanoic acid (Compound No. 74);

(2S,3R)-5-(3',6-difluoro-4'-methoxybiphenyl-3-yl)-2-[2-(1,3-dioxo-1,3-dihydro-2H-isoindol-2-yl)ethyl]-3-hydroxypentanoic acid (Compound No. 75);

(2S,3R)-2-[2-(5-fluoro-4-oxo-1,2,3-benzotriazin-3(4H)-yl)ethyl]-5-(4'-methoxybiphenyl-4-yl)pentanoic acid (Compound No. 76);

(2S,3R)-5-(4'-fluorobiphenyl-4-yl)-2-[2-(5-fluoro-4-oxo-1,2,3-benzotriazin-3(4H)-yl)ethyl]-3-hydroxypentanoic acid (Compound No. 77);

(2S,3R)-3-hydroxy-2-[2-(6-methyl-4-oxo-1,2,3-benzotriazin-3(4H)-yl)ethyl]-5-[4-(1-methyl-1H-pyrazol-4-yl)phenyl]pentanoic acid (Compound No. 78);

(2S,3R)-2-[2-(5-chloro-1,3-dioxo-1,3-dihydro-2H-isoindol-2-yl)ethyl]-3-hydroxy-5-[4'-(trifluoromethyl)biphenyl-4-yl]pentanoic acid (Compound No. 79);

(2S,3R)-2-[2-(4-fluoro-1,3-dioxo-1,3-dihydro-2H-isoindol-2-yl)ethyl]-3-hydroxy-5-[4'-(trifluoromethyl)biphenyl-4-yl]pentanoic acid (Compound No. 80);

(2S,3R)-5-(3',4'-difluorobiphenyl-4-yl)-2-[2-(5-fluoro-4-oxo-1,2,3-benzotriazin-3(4H)-yl)ethyl]-3-hydroxypentanoic acid (Compound No. 81);

(2S,3R)-3-hydroxy-2-[2-(4-oxo-1,2,3-benzotriazin-3(4H)-yl)ethyl]-5-phenylpentanoic acid (Compound No. 82);

(2S,3R)-2-[2-(1,3-dioxo-1,3-dihydro-2H-isoindol-2-yl)ethyl]-3-hydroxy-5-phenylpentanoic acid (Compound No. 83);

(2S,3R)-2-[2-(1,3-dioxo-1,3-dihydro-2H-isoindol-2-yl)ethyl]-3-hydroxy-5-[4(trifluoromethyl)phenyl]pentanoic acid (Compound No. 84);

(2S,3R)-5-(4-tert-butylphenyl)-2-[2-(1,3-dioxo-1,3-dihydro-2H-isoindol-2-yl)ethyl]-3-hydroxypentanoic acid (Compound No. 85);

(2S,3R)-3-hydroxy-2-[2-(7-methyl-4-oxo-1,2,3-benzotriazin-3(4H)-yl)ethyl]-5-[4-(1-methyl-1H-pyrazol-4-yl)phenyl]pentanoic acid (Compound No. 90);

(2S,3R)-3-hydroxy-2-[2-(8-methoxy-4-oxo-1,2,3-benzotriazin-3(4H)-yl)ethyl]-5-[4-(1-methyl-1H-pyrazol-4-yl)phenyl]pentanoic acid (Compound No. 91);

(2S,3R)-2-[2-(7-chloro-4-oxo-1,2,3-benzotriazin-3(4H)-yl)ethyl]-5-(3',4'-difluorobiphenyl-4-yl)-3-hydroxypentanoic acid (Compound No. 92);

(2S,3R)-2-[2-(7-chloro-4-oxo-1,2,3-benzotriazin-3(4H)-yl)ethyl]-3-hydroxy-5-(4'-methoxybiphenyl-4-yl)pentanoic acid (Compound No. 93);

(2S,3R)-2-[2-(7-chloro-4-oxo-1,2,3-benzotriazin-3(4H)-yl)ethyl]-5-(4'-fluorobiphenyl-4-yl)-3-hydroxypentanoic acid (Compound No. 94);

(2S,3R)-2-[2-(7-chloro-4-oxo-1,2,3-benzotriazin-3(4H)-yl)ethyl]-3-hydroxy-5-[4-(6-methylpyridin-3-yl)phenyl]pentanoic acid (Compound No. 95);

(2S,3R)-5-(2',4'-difluorobiphenyl-4-yl)-2-[2-(1,3-dioxo-1,3-dihydro-2H-isoindol-2-yl)ethyl]-3-hydroxypentanoic acid (Compound No. 97);

(2S,3R)-2-[2-(6-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 98);

(2S,3R)-2-[2-(5-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 99);

(2S,3R)-2-[2-(1,3-dioxo-1,3-dihydro-2H-isoindol-2-yl)ethyl]-3-hydroxy-5-(4'-isopropylbiphenyl-4-yl)pentanoic acid (Compound No. 100);

(2S,3R)-5-(3'-chloro-4'-fluorobiphenyl-4-yl)-2-[2-(1,3-dioxo-1,3-dihydro-2H-isoindol-2-yl)ethyl]-3-hydroxypentanoic acid (Compound No. 101);

(2S,3R)-5-(4'-butylbiphenyl-4-yl)-3-hydroxy-2-[2-(4-oxo-1,2,3-benzotriazin-3(4H)-yl)ethyl]pentanoic acid (Compound No. 102);

(2S,3R)-5-(2'-fluorobiphenyl-4-yl)-3-hydroxy-2-[2-(4-oxo-1,2,3-benzotriazin-3(4H)-yl)ethyl]pentanoic acid (Compound No. 103);

(2S,3R)-2-[2-(5-fluoro-4-oxo-1,2,3-benzotriazin-3(4H)-yl)ethyl]-3-hydroxy-5-[4-(1-methyl-1H-pyrazol-4-yl)phenyl]pentanoic acid (Compound No. 104);

(2S,3R)-3-hydroxy-2-[2-(8-methyl-4-oxo-1,2,3-benzotriazin-3(4H)-yl)ethyl]-5-[4-(1-methyl-1H-pyrazol-4-yl)phenyl]pentanoic acid (Compound No. 105);

(2S,3R)-2-[2-(1,3-dioxo-1,3-dihydro-2H-isoindol-2-yl)ethyl]-3-hydroxy-5-{6-[4-(trifluoromethyl)phenyl]pyridin-3-yl}pentanoic acid (Compound No. 106);

(2S,3R)-5-[6-(3,4-difluorophenyl)pyridin-3-yl]-2-[2-(1,3-dioxo-1,3-dihydro-2H-isoindol-2-yl)ethyl]-3-hydroxypentanoic acid (Compound No. 107);

(2S,3R)-5-[6-(4-chloro-3-fluorophenyl)pyridin-3-yl]-2-[2-(1,3-dioxo-1,3-dihydro-2H-isoindol-2-yl)ethyl]-3-hydroxypentanoic acid (Compound No. 108);

(2S,3R)-2-[2-(1,3-dioxo-1,3-dihydro-2H-isoindol-2-yl)ethyl]-5-[6-(4-fluorophenyl)pyridin-3-yl]-3-hydroxypentanoic acid (Compound No. 109);

(2S,3R)-2-[2-(1,3-dioxo-1,3-dihydro-2H-isoindol-2-yl)ethyl]-5-[6-(3-fluoro-4-methylphenyl)pyridin-3-yl]-3-hydroxypentanoic acid (Compound No. 110);

(2S,3R)-2-[2-(7-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 111);

(2S,3R)-2-[2-(8-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 112);

(2S,3R)-2-[2-(6,7-difluoro-4-oxo-1,2,3-benzotriazin-3(4H)-yl)ethyl]-3-hydroxy-5-[4-(1-methyl-1H-pyrazol-4-yl)phenyl]pentanoic acid (Compound No. 113);

(2S,3R)-3-hydroxy-2-[2-(7-methyl-4-oxo-1,2,3-benzotriazin-3(4H)-yl)ethyl]-5-[4'-(trifluoromethoxy)biphenyl-4-yl]pentanoic acid (Compound No. 114);

(2S,3R)-3-hydroxy-5-(4'-methylbiphenyl-4-yl)-2-[2-(7-methyl-4-oxo-1,2,3-benzotriazin-3(4H)-yl)ethyl]pentanoic acid (Compound No. 115);

(2S,3R)-5-(4'-fluorobiphenyl-4-yl)-3-hydroxy-2-[2-(7-methyl-4-oxo-1,2,3-benzotriazin-3(4H)-yl)ethyl]pentanoic acid (Compound No. 116);

(2S,3R)-5-(3',4'-difluorobiphenyl-4-yl)-3-hydroxy-2-[2-(7-methyl-4-oxo-1,2,3-benzotriazin-3(4H)-yl)ethyl]pentanoic acid (Compound No. 117);

(2S,3R)-3-hydroxy-2-[2-(7-methyl-4-oxo-1,2,3-benzotriazin-3(4H)-yl)ethyl]-5-[4-(6-methylpyridin-3-yl)phenyl]pentanoic acid (Compound No. 118);

(2S,3R)-5-[4-(2,3-dihydro-1,4-benzodioxin-6-yl)phenyl]-3-hydroxy-2-[2-(7-methyl-4-oxo-1,2,3-benzotriazin-3(4H)-yl)ethyl]pentanoic acid (Compound No. 119);

(2S,3R)-2-[2-(5-chloro-4-oxo-1,2,3-benzotriazin-3(4H)-yl)ethyl]-3-hydroxy-5-(6'-methoxy-2,3'-bipyridin-5-yl)pentanoic acid (Compound No. 121);

(2S,3R)-2-[2-(7-chloro-4-oxo-1,2,3-benzotriazin-3(4H)-yl)ethyl]-3-hydroxy-5-(6'-methoxy-2,3'-bipyridin-5-yl)pentanoic acid (Compound No. 122);

(2S,3R)-2-[2-(6,7-difluoro-4-oxo-1,2,3-benzotriazin-3(4H)-yl)ethyl]-3-hydroxy-5-(6'-methoxy-2,3'-bipyridin-5-yl)pentanoic acid (Compound No. 123);

(2S,3R)-5-(3'-fluoro-4'-methylbiphenyl-4-yl)-3-hydroxy-2-[2-(7-methyl-4-oxo-1,2,3-benzotriazin-3(4H)-yl)ethyl]pentanoic acid (Compound No. 124);

(2S,3R)-3-hydroxy-5-[4-(1-isobutyl-1H-pyrazol-4-yl)phenyl]-2-[2-(7-methyl-4-oxo-1,2,3-benzotriazin-3(4H)-yl)ethyl]pentanoic acid (Compound No. 125);

(2S,3R)-2-[2-(5-fluoro-4-oxo-1,2,3-benzotriazin-3(4H)-yl)ethyl]-3-hydroxy-5-(6'-methoxy-2,3'-bipyridin-5-yl)pentanoic acid (Compound No. 126);

(2S,3R)-5-(4'-fluorobiphenyl-4-yl)-3-hydroxy-2-[2-(8-methoxy-4-oxo-1,2,3-benzotriazin-3(4H)-yl)ethyl]pentanoic acid (Compound No. 127);

(2S,3R)-5-(3',4'-difluorobiphenyl-4-yl)-3-hydroxy-2-[2-(8-methoxy-4-oxo-1,2,3-benzotriazin-3(4H)-yl)ethyl]pentanoic acid (Compound No. 128);

(2S,3R)-3-hydroxy-5-(4'-methoxybiphenyl-4-yl)-2-[2-(8-methoxy-4-oxo-1,2,3-benzotriazin-3(4H)-yl)ethyl]pentanoic acid (Compound No. 129);

(2S,3R)-2-[2-(7-chloro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 130);

(2S,3R)-2-[2-(6,7-difluoro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 131);

(2S,3R)-2-[2-(5-chloro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 132);

(2S,3R)-3-hydroxy-2-[2-(7-methyl-4-oxo-1,2,3-benzotriazin-3(4H)-yl)ethyl]-5-{6-[4-(trifluoromethyl)phenyl]pyridin-3-yl}pentanoic acid (Compound No. 133);

(2S,3R)-2-[2-(5-fluoro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 134);

(2S,3R)-3-hydroxy-2-[2-(8-methoxy-4-oxo-1,2,3-benzotriazin-3(4H)-yl)ethyl]-5-(4'-methylbiphenyl-4-yl)pentanoic acid (Compound No. 135);

(2S,3R)-5-(3'-fluoro-4'-methylbiphenyl-4-yl)-2-[2-(5-fluoro-4-oxo-1,2,3-benzotriazin-3(4H)-yl)ethyl]-3-hydroxypentanoic acid (Compound No. 136);

(2S,3R)-2-[2-(6,7-difluoro-4-oxo-1,2,3-benzotriazin-3(4H)-yl)ethyl]-3-hydroxy-5-(4'-methylbiphenyl-4-yl)pentanoic acid (Compound No. 137);

(2S,3R)-2-[2-(5-fluoro-4-oxo-1,2,3-benzotriazin-3(4H)-yl)ethyl]-3-hydroxy-5-(4'-methylbiphenyl-4-yl)pentanoic acid (Compound No. 138);

(2S,3R)-5-(4'-chlorobiphenyl-4-yl)-2-[2-(5-fluoro-4-oxo-1,2,3-benzotriazin-3(4H)-yl)ethyl]-3-hydroxypentanoic acid (Compound No. 139);

(2S,3R)-3-hydroxy-5-(6'-methoxy-2,3'-bipyridin-5-yl)-2-[2-(4-oxo-1,2,3-benzotriazin-3(4H)-yl)ethyl]pentanoic acid (Compound No. 140);

(2S,3R)-3-hydroxy-5-(6'-methoxy-2,3'-bipyridin-5-yl)-2-[2-(6-methyl-4-oxo-1,2,3-benzotriazin-3(4H)-yl)ethyl]pentanoic acid (Compound No. 141);

(2S,3R)-3-hydroxy-5-(6'-methoxy-2,3'-bipyridin-5-yl)-2-[2-(7-methyl-4-oxo-1,2,3-benzotriazin-3(4H)-yl)ethyl]pentanoic acid (Compound No. 142);

(2S,3S)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 143);

(2S,3R)-2-[2-(6,7-difluoro-4-oxo-1,2,3-benzotriazin-3(4H)-yl)ethyl]-5-(3'-fluoro-4'-methylbiphenyl-4-yl)-3-hydroxypentanoic acid (Compound No. 144);

(2S,3R)-5-(4'-chlorobiphenyl-4-yl)-2-[2-(6,7-difluoro-4-oxo-1,2,3-benzotriazin-3(4H)-yl)ethyl]-3-hydroxypentanoic acid (Compound No. 145);

(2S,3R)-5-(3'-fluoro-4'-methylbiphenyl-4-yl)-3-hydroxy-2-[2-(8-methoxy-4-oxo-1,2,3-benzotriazin-3(4H)-yl)ethyl]pentanoic acid (Compound No. 146);

(2S,3R)-5-[4-(2,3-dihydro-1,4-benzodioxin-6-yl)phenyl]-3-hydroxy-2-[2-(8-methoxy-4-oxo-1,2,3-benzotriazin-3(4H)-yl)ethyl]pentanoic acid (Compound No. 147);

(2S,3R)-5-[4-(6-chloropyridin-3-yl)phenyl]-3-hydroxy-2-[2-(4-oxo-1,2,3-benzotriazin-3(4H)-yl)ethyl]pentanoic acid (Compound No. 148);

(2S,3R)-3-hydroxy-2-[2-(6-methoxy-4-oxo-1,2,3-benzotriazin-3 (4H)-yl)ethyl]-5-[4'-(trifluoromethyl)biphenyl-4-yl]pentanoic acid (Compound No. 149);

(2S,3R)-3-hydroxy-2-[2-(7-methoxy-4-oxo-1,2,3-benzotriazin-3 (4H)-yl)ethyl]-5-[4'-(trifluoromethyl)biphenyl-4-yl]pentanoic acid (Compound No. 150);

(2S,3R)-3-hydroxy-2-[2-(6-methoxy-4-oxo-1,2,3-benzotriazin-3 (4H)-yl)ethyl]-5-(4'-methylbiphenyl-4-yl)pentanoic acid (Compound No. 151);

(2S,3R)-3-hydroxy-5-(4'-methoxybiphenyl-4-yl)-2-[2-(6-methoxy-4-oxo-1,2,3-benzotriazin-3(4H)-yl)ethyl]pentanoic acid (Compound No. 152);

(2S,3R)-5-[2-fluoro-4-(6-methoxypyridin-3-yl)phenyl]-3-hydroxy-2-[2-(4-oxo-1,2,3-benzotriazin-3(4H)-yl)ethyl]pentanoic acid (Compound No. 153);

(2S,3R)-5-[2-fluoro-4-(6-methoxypyridin-3-yl)phenyl]-3-hydroxy-2-[2-(7-methoxy-4-oxo-1,2,3-benzotriazin-3 (4H)-yl)ethyl]pentanoic acid (Compound No. 154);

(2S,3R)-5-[2-fluoro-4-(6-methoxypyridin-3-yl)phenyl]-2-[2-(5-fluoro-4-oxo-1,2,3-benzotriazin-3 (4H)-yl)ethyl]-3-hydroxypentanoic acid (Compound No. 155);

(2S,3R)-5-[2-fluoro-4-(6-methoxypyridin-3-yl)phenyl]-3-hydroxy-2-[2-(7-methyl-4-oxo-1,2,3-benzotriazin-3 (4H)-yl)ethyl]pentanoic acid (Compound No. 156);

(2S,3R)-5-[2-fluoro-4-(6-methoxypyridin-3-yl)phenyl]-3-hydroxy-2-[2-(6-methyl-4-oxo-1,2,3-benzotriazin-3 (4H)-yl)ethyl]pentanoic acid (Compound No. 157);

(2S,3R)-3-hydroxy-5-(4'-methoxybiphenyl-4-yl)-2-[2-(7-methoxy-4-oxo-1,2,3-benzotriazin-3(4H)-yl)ethyl]pentanoic acid (Compound No. 158);

(2S,3R)-5-(4'-chlorobiphenyl-4-yl)-3-hydroxy-2-[2-(6-methoxy-4-oxo-1,2,3-benzotriazin-3(4H)-yl)ethyl]pentanoic acid (Compound No. 159);

(2S,3R)-3-hydroxy-2-[2-(7-methoxy-4-oxo-1,2,3-benzotriazin-3 (4H)-yl)ethyl]-5-[4-(6-methoxypyridin-3-yl)phenyl]pentanoic acid (Compound No. 160);

(2S,3R)-5-(3',4'-difluorobiphenyl-4-yl)-3-hydroxy-2-[2-(7-methoxy-4-oxo-1,2,3-benzotriazin-3(4H)-yl)ethyl]pentanoic acid (Compound No. 161);

(2S,3R)-3-hydroxy-2-[2-(6-methoxy-4-oxo-1,2,3-benzotriazin-3 (4H)-yl)ethyl]-5-[4-(6-methoxypyridin-3-yl)phenyl]pentanoic acid (Compound No. 162);

(2S,3R)-2-[2-(5-chloro-4-oxo-1,2,3-benzotriazin-3 (4H)-yl)ethyl]-5-[2-fluoro-4-(6-methoxypyridin-3-yl)phenyl]-3-hydroxypentanoic acid (Compound No. 163);

(2S,3R)-2-[2-(6,7-difluoro-4-oxo-1,2,3-benzotriazin-3 (4H)-yl)ethyl]-5-[2-fluoro-4-(6-methoxypyridin-3-yl) phenyl]-3-hydroxypentanoic acid (Compound No. 164);

(2S,3R)-5-[2-fluoro-4-(6-methoxypyridin-3-yl)phenyl]-3-hydroxy-2-[2-(5-methyl-4-oxo-1,2,3-benzotriazin-3 (4H)-yl)ethyl]pentanoic acid (Compound No. 165);

(2S,3R)-5-(4'-fluorobiphenyl-4-yl)-3-hydroxy-2-[2-(5-methyl-4-oxo-1,2,3-benzotriazin-3(4H)-yl)ethyl]pentanoic acid (Compound No. 166);

(2S,3R)-3-hydroxy-5-[4-(6-methoxypyridin-3-yl)phenyl]-2-[2-(5-methyl-4-oxo-1,2,3-benzotriazin-3(4H)-yl)ethyl] pentanoic acid (Compound No. 167);

(2S,3R)-3-hydroxy-5-(4'-methoxybiphenyl-4-yl)-2-[2-(5-methyl-4-oxo-1,2,3-benzotriazin-3(4H)-yl)ethyl]pentanoic acid (Compound No. 168);

(2S,3R)-3-hydroxy-5-(4'-methylbiphenyl-4-yl)-2-[2-(5-methyl-4-oxo-1,2,3-benzotriazin-3(4H)-yl)ethyl]pentanoic acid (Compound No. 169);

(2S,3R)-5-(4'-chlorobiphenyl-4-yl)-3-hydroxy-2-[2-(5-methyl-4-oxo-1,2,3-benzotriazin-3(4H)-yl)ethyl]pentanoic acid (Compound No. 170);

(2S,3R)-5-(4'-fluorobiphenyl-4-yl)-3-hydroxy-2-[2-(6-methoxy-4-oxo-1,2,3-benzotriazin-3(4H)-yl)ethyl]pentanoic acid (Compound No. 171);

(2S,3R)-5-(3',4'-difluorobiphenyl-4-yl)-3-hydroxy-2-[2-(6-methoxy-4-oxo-1,2,3-benzotriazin-3(4H)-yl)ethyl]pentanoic acid (Compound No. 172);

(2S,3R)-3-hydroxy-2-[2-(6-methoxy-4-oxo-1,2,3-benzotriazin-3(4H)-yl)ethyl]-5-[4'-(trifluoromethoxy)biphenyl-4-yl]pentanoic acid (Compound No. 173);

(2S,3R)-5-(3'-fluoro-4'-methylbiphenyl-4-yl)-3-hydroxy-2-[2-(6-methoxy-4-oxo-1,2,3-benzotriazin-3(4H)-yl)ethyl] pentanoic acid (Compound No. 174);

(2S,3R)-2-[2-(7-chloro-4-oxo-1,2,3-benzotriazin-3(4H)-yl) ethyl]-5-[2-fluoro-4-(6-methoxypyridin-3-yl)phenyl]-3-hydroxypentanoic acid (Compound No. 175);

(2S,3R)-3-hydroxy-5-[4-(1-methyl-1H-pyrazol-4-yl)-2-thienyl]-2-[2-(4-oxo-1,2,3-benzotriazin-3(4H)-yl)ethyl] pentanoic acid (Compound No. 176);

(2S,3R)-5-[2-fluoro-4-(6-methoxypyridin-3-yl)phenyl]-3-hydroxy-2-[2-(6-methoxy-4-oxo-1,2,3-benzotriazin-3 (4H)-yl)ethyl]pentanoic acid (Compound No. 177);

(2S,3R)-3-hydroxy-5-(6'-methoxy-2,3'-bipyridin-5-yl)-2-[2-(6-methoxy-4-oxo-1,2,3-benzotriazin-3(4H)-yl)ethyl] pentanoic acid (Compound No. 178);

(2S,3R)-3-hydroxy-2-[2-(6-methoxy-4-oxo-1,2,3-benzotriazin-3(4H)-yl)ethyl]-5-[4-(6-methylpyridin-3-yl)phenyl] pentanoic acid (Compound No. 179);

(2S,3R)-5-[4-(2-chloropyridin-3-yl)phenyl]-3-hydroxy-2-[2-(6-methoxy-4-oxo-1,2,3-benzotriazin-3(4H)-yl)ethyl] pentanoic acid (Compound No. 180);

(2S,3R)-2-[2-(6-fluoro-4-oxo-1,2,3-benzotriazin-3(4H)-yl) ethyl]-3-hydroxy-5-[4-(6-methoxypyridin-3-yl)phenyl] pentanoic acid (Compound No. 181);

(2S,3R)-5-(4'-chlorobiphenyl-4-yl)-2-[2-(6-fluoro-4-oxo-1,2,3-benzotriazin-3(4H)-yl)ethyl]-3-hydroxypentanoic acid (Compound No. 182);

(2S,3R)-5-(3',4'-difluorobiphenyl-4-yl)-2-[2-(6-fluoro-4-oxo-1,2,3-benzotriazin-3(4H)-yl)ethyl]-3-hydroxypentanoic acid (Compound No. 183);

(2S,3R)-2-[2-(6-fluoro-4-oxo-1,2,3-benzotriazin-3(4H)-yl) ethyl]-3-hydroxy-5-(4'-methoxybiphenyl-4-yl)pentanoic acid (Compound No. 184);

(2S,3R)-3-hydroxy-5-[4-(2-methoxypyrimidin-5-yl)phenyl]-2-[2-(4-oxo-1,2,3-benzotriazin-3(4H)-yl)ethyl]pentanoic acid (Compound No. 185);

(2S,3R)-5-[2-fluoro-4-(1-methyl-1H-pyrazol-4-yl)phenyl]-3-hydroxy-2-[2-(6-methyl-4-oxo-1,2,3-benzotriazin-3 (4H)-yl)ethyl]pentanoic acid (Compound No. 186);

(2S,3R)-5-[2-fluoro-4-(1-methyl-1H-pyrazol-4-yl)phenyl]-3-hydroxy-2-[2-(7-methyl-4-oxo-1,2,3-benzotriazin-3 (4H)-yl)ethyl]pentanoic acid (Compound No. 187);

(2S,3R)-2-[2-(5-chloro-4-oxo-1,2,3-benzotriazin-3(4H)-yl) ethyl]-5-[2-fluoro-4-(1-methyl-1H-pyrazol-4-yl)phenyl]-3-hydroxypentanoic acid (Compound No. 188);

(2S,3R)-2-[2-(7-chloro-4-oxo-1,2,3-benzotriazin-3(4H)-yl) ethyl]-5-[2-fluoro-4-(1-methyl-1H-pyrazol-4-yl)phenyl]-3-hydroxypentanoic acid (Compound No. 189);

(2S,3R)-5-[2-fluoro-4-(1-methyl-1H-pyrazol-4-yl)phenyl]-2-[2-(5-fluoro-4-oxo-1,2,3-benzotriazin-3(4H)-yl)ethyl]-3-hydroxypentanoic acid (Compound No. 190);

(2S,3R)-2-[2-(6,7-difluoro-4-oxo-1,2,3-benzotriazin-3(4H)-yl)ethyl]-5-[2-fluoro-4-(1-methyl-1H-pyrazol-4-yl)phenyl]-3-hydroxypentanoic acid (Compound No. 191);

(2S,3R)-5-[2-fluoro-4-(1-methyl-1H-pyrazol-4-yl)phenyl]-2-[2-(6-fluoro-4-oxo-1,2,3-benzotriazin-3(4H)-yl)ethyl]-3-hydroxypentanoic acid (Compound No. 192);

(2S,3R)-5-[2-fluoro-4-(1-methyl-1H-pyrazol-4-yl)phenyl]-3-hydroxy-2-[2-(8-methyl-4-oxo-1,2,3-benzotriazin-3(4H)-yl)ethyl]pentanoic acid (Compound No. 193);

(2S,3R)-3-hydroxy-2-[2-(6-methoxy-4-oxo-1,2,3-benzotriazin-3(4H)-yl)ethyl]-5-[4-(2-methoxypyrimidin-5-yl)phenyl]pentanoic acid (Compound No. 194);

(2S,3R)-2-[2-(1,3-dioxo-1,3-dihydro-2H-isoindol-2-yl)ethyl]-3-hydroxy-5-[4-(2-methoxypyrimidin-5-yl)phenyl]pentanoic acid (Compound No. 195);

(2S,3R)-5-[2-fluoro-4-(1-methyl-1H-pyrazol-4-yl)phenyl]-3-hydroxy-2-[2-(1-oxophthalazin-2(1H)-yl)ethyl]pentanoic acid (Compound No. 196);

(2S,3R)-5-[2-fluoro-4-(1-methyl-1H-pyrazol-4-yl)phenyl]-3-hydroxy-2-[2-(3-methyl-2,6-dioxo-3,6-dihydropyrimidin-1(2H)-yl)ethyl]pentanoic acid (Compound No. 197);

(2S,3R)-3-hydroxy-5-[4-(6-methoxypyridin-3-yl)phenyl]-2-{2-[4-oxo-7-(trifluoromethyl)-1,2,3-benzotriazin-3(4H)-yl]ethyl}pentanoic acid (Compound No. 198);

(2S,3R)-3-hydroxy-5-[4-(6-methoxypyridin-3-yl)phenyl]-2-[2-(1-oxophthalazin-2(1H)-yl)ethyl]pentanoic acid (Compound No. 199);

(2S,3R)-3-hydroxy-5-[4-(6-methoxypyridin-3-yl)phenyl]-2-[2-(3-methyl-2,6-dioxo-3,6-dihydropyrimidin-1(2H)-yl)ethyl]pentanoic acid (Compound No. 200);

(2S,3R)-2-[2-(7,9-dioxo-8-azaspiro[4.5]dec-8-yl)ethyl]-3-hydroxy-5-[4-(6-methoxypyridin-3-yl)phenyl]pentanoic acid (Compound No. 201);

(2S,3R)-2-[2-(2,4-dioxo-2H-1,3-benzoxazin-3(4H)-yl)ethyl]-3-hydroxy-5-[4-(6-methoxypyridin-3-yl)phenyl]pentanoic acid (Compound No. 202);

(2S,3R)-3-hydroxy-5-[4-(6-methoxypyridin-3-yl)phenyl]-2-[2-(3,4,4-trimethyl-2,5-dioxoimidazolidin-1-yl)ethyl]pentanoic acid (Compound No. 203);

(2S,3R)-5-(4-chloro-3-fluorophenyl)-2-[2-(1,3-dioxo-1,3-dihydro-2H-isoindol-2-yl)ethyl]-3-hydroxypentanoic acid (Compound No. 204);

(2R,3S)-2-[2-(1,3-dioxo-1,3-dihydro-2H-isoindol-2-yl)ethyl]-5-(3'-fluoro-4'-methylbiphenyl-4-yl)-3-hydroxypentanoic acid (Compound No. 205);

(2R,3S)-2-[2-(1,3-dioxo-1,3-dihydro-2H-isoindol-2-yl)ethyl]-5-(4'-fluorobiphenyl-4-yl)-3-hydroxypentanoic acid (Compound No. 206);

(2R,3S)-5-(3',4'-difluorobiphenyl-4-yl)-2-[2-(1,3-dioxo-1,3-dihydro-2H-isoindol-2-yl)ethyl]-3-hydroxypentanoic acid (Compound No. 207);

(2S,3S)-3-hydroxy-5-(4'-methoxybiphenyl-4-yl)-2-[2-(4-oxo-1,2,3-benzotriazin-3(4H)-yl)ethyl]pentanoic acid (Compound No. 208);

(2S,3R)-3-hydroxy-5-[4-(5-methylpyridin-2-yl)phenyl]-2-[2-(4-oxo-1,2,3-benzotriazin-3(4H)-yl)ethyl]pentanoic acid (Compound No. 209);

(2S,3R)-5-[4-(6-fluoropyridin-3-yl)phenyl]-3-hydroxy-2-[2-(4-oxo-1,2,3-benzotriazin-3(4H)-yl)ethyl]pentanoic acid (Compound No. 210);

(2S,3R)-2-[2-(5-fluoro-4-oxo-1,2,3-benzotriazin-3(4H)-yl)ethyl]-3-hydroxy-5-[4'-(trifluoromethyl)biphenyl-4-yl]pentanoic acid (Compound No. 211);

(2S,3R)-5-(4'-chlorobiphenyl-4-yl)-3-hydroxy-2-[2-(7-methyl-4-oxo-1,2,3-benzotriazin-3(4H)-yl)ethyl]pentanoic acid (Compound No. 212);

(2S,3R)-3-hydroxy-5-(6'-methoxy-2,3'-bipyridin-5-yl)-2-[2-(8-methyl-4-oxo-1,2,3-benzotriazin-3(4H)-yl)ethyl]pentanoic acid (Compound No. 213);

(2S,3R)-5-(3'-fluoro-4'-methylbiphenyl-4-yl)-3-hydroxy-2-[(4-oxo-1,2,3-benzotriazin-3(4H)-yl)methyl]pentanoic acid (Compound No. 214);

(2S,3R)-3-hydroxy-2-[(4-oxo-1,2,3-benzotriazin-3(4H)-yl)methyl]-5-[4'-(trifluoromethyl)biphenyl-4-yl]pentanoic acid (Compound No. 215);

(2S,3R)-5-(2',4'-difluorobiphenyl-4-yl)-3-hydroxy-2-[(4-oxo-1,2,3-benzotriazin-3(4H)-yl)methyl]pentanoic acid (Compound No. 216);

(2S,3R)-5-(4'-fluorobiphenyl-4-yl)-3-hydroxy-2-[(4-oxo-1,2,3-benzotriazin-3(4H)-yl)methyl]pentanoic acid (Compound No. 217);

(2S,3R)-5-(3'-fluoro-4'-methoxybiphenyl-4-yl)-3-hydroxy-2-[(4-oxo-1,2,3-benzotriazin-3(4H)-yl)methyl]pentanoic acid (Compound No. 218);

(2S,3R)-3-hydroxy-5-[4-(2-methoxypyrimidin-5-yl)phenyl]-2-[(4-oxo-1,2,3-benzotriazin-3(4H)-yl)methyl]pentanoic acid (Compound No. 219);

(2S,3R)-3-hydroxy-5-[4-(6-methoxypyridin-3-yl)phenyl]-2-[(4-oxo-1,2,3-benzotriazin-3(4H)-yl)methyl]pentanoic acid (Compound No. 220);

(2S,3R)-3-hydroxy-5-(4'-methylbiphenyl-4-yl)-2-[(4-oxo-1,2,3-benzotriazin-3(4H)-yl)methyl]pentanoic acid (Compound No. 221);

(2S,3R)-3-hydroxy-2-[(4-oxo-1,2,3-benzotriazin-3(4H)-yl)methyl]-5-[4'-(trifluoromethoxy)biphenyl-4-yl]pentanoic acid (Compound No. 222);

(2S,3R)-3-hydroxy-5-[4-(6-methylpyridin-3-yl)phenyl]-2-[(4-oxo-1,2,3-benzotriazin-3(4H)-yl)methyl]pentanoic acid (Compound No. 223);

(2S,3R)-5-(4'-chlorobiphenyl-4-yl)-3-hydroxy-2-[(4-oxo-1,2,3-benzotriazin-3(4H)-yl)methyl]pentanoic acid (Compound No. 224);

(2S,3R)-5-(3',4'-difluorobiphenyl-4-yl)-3-hydroxy-2-[(4-oxo-1,2,3-benzotriazin-3(4H)-yl)methyl]pentanoic acid (Compound No. 225);

(2S,3R)-3-hydroxy-5-[4-(6-hydroxypyridin-3-yl)phenyl]-2-[2-(4-oxo-1,2,3-benzotriazin-3(4H)-yl)ethyl]pentanoic acid (Compound No. 226);

(2S,3R)-3-hydroxy-5-(4'-methylbiphenyl-4-yl)-2-{2-[4-oxo-7-(trifluoromethyl)-1,2,3-benzotriazin-3(4H)-yl]ethyl}pentanoic acid (Compound No. 227);

(2S,3R)-2-[2-(2,4-dioxo-1,4-dihydroquinazolin-3(2H)-yl)ethyl]-3-hydroxy-5-[4-(6-methoxypyridin-3-yl)phenyl]pentanoic acid (Compound No. 228);

(2S,3R)-3-(acetyloxy)-5-[4-(6-methoxypyridin-3-yl)phenyl]-2-[2-(4-oxo-1,2,3-benzotriazin-3(4H)-yl)ethyl]pentanoic acid (Compound No. 229);

(2S,3R)-2-[2-(8-chloro-4-oxo-1,2,3-benzotriazin-3(4H)-yl)ethyl]-3-hydroxy-5-[4-(6-methoxypyridin-3-yl)phenyl]pentanoic acid (Compound No. 230);

(2S,3R)-5-(4'-chlorobiphenyl-4-yl)-2-[2-(2,4-dioxo-2H-1,3-benzoxazin-3(4H)-yl)ethyl]-3-hydroxypentanoic acid (Compound No. 231); and (2S,3R)-5-(4'-chlorobiphenyl-4-yl)-3-hydroxy-2-(2-{[(2-hydroxyphenyl)carbonyl]amino}ethyl)pentanoic acid (Compound No. 232).

In another embodiment, the present invention relates to a chiral auxiliary (4S)-4-benzyl-1,3-thiazolidin-2-one which would be of versatile utility for asymmetric synthesis. Chiral auxiliaries are utilized in a wide variety of synthetic transformations which include, but are not limited to, asymmetric aldol condensation, stereoselective alkylation, stereoselective Diels-Alder reaction, stereoselective Michael reactions, and stereoselective differentiation of enantiotopic groups in molecules bearing prochiral centers. The chiral auxiliary is used in stoichiometric amounts to induce the stereoselective formation of stereogenic centers.

In another embodiment, the present invention relates to the therapeutically effective dose of a compound of Formula I in combination with one or more other therapeutic agents used for treating various inflammatory and allergic diseases. Examples of such therapeutic agents include, but are not limited to:

1) Anti-inflammatory agents, experimental or commercial such as (i) nonsteroidal anti-inflammatory agents piroxicam, diclofenac, propionic acids, fenamates, pyrazolones, salicylates, PDE-4/p38 MAP Kinase/Cathepsin inhibitors, CCR-3 antagonists, iNOS inhibitors, tryptase and elastase inhibitors, beta-2 integrin antagonists, cell adhesion inhibitors (especially ICAM), or adenosine 2a agonists; (ii) leukotrienes LTC4/LTD4/LTE4/LTB4-Inhibitors, 5-lipoxygenase inhibitors, and PAF-receptor antagonists; (iii) Cox-2 inhibitors; (iv) other MMP inhibitors; (v) interleukin-1 inhibitors; or (vi) corticosteroids such as alclometasone, amcinonide, amelometasone, beclometasone, betamethasone, budesonide, ciclesonide, clobetasol, cloticasone, cyclomethasone, deflazacort, deprodone, dexbudesonide, diflorasone, difluprednate, fluticasone, flunisolide, halometasone, halopredone, hydrocortisone, methylprednisolone, mometasone, prednicarbate, prednisolone, rimexolone, tixocortol, triamcinolone, ulobetasol, rofleponide, GW 215864, KSR 592, ST-126, dexamethasone, and pharmaceutically acceptable salts or solvates thereof. Preferred corticosteroids include, for example, flunisolide, beclomethasone, triamcinolone, budesonide, fluticasone, mometasone, ciclesonide, and dexamethasone;

2) Beta-agonists, experimental or commercial, suitable β2-agonists include, for example, (i) one or more of albuterol, salbutamol, biltolterol, pirbuterol, levosalbutamol, tulobuterol, terbutaline, bambuterol, metaproterenol, fenoterol, salmeterol, carmoterol, arformoterol, or formoterol, and pharmaceutically acceptable salts or solvates thereof. One or more β2-agonists may be chosen from those in the art or subsequently discovered. (ii) The β2-agonists may include one or more compounds described in, for example, U.S. Pat. Nos. 3,705,233; 3,644,353; 3,642,896; 3,700,681; 4,579,985; 3,994,974; 3,937,838; 4,419,364; 5,126,375; 5,243,076; 4,992,474; and 4,011,258;

3) antihypertensive agents, (i) ACE inhibitors, e.g., enalapril, lisinopril, valsartan, Telmisartan, and quinapril; (ii) angiotensin II receptor antagonists and agonists, e.g., losartan, candesartan, irbesartan, valsartan, and eprosartan; (iii) β-blockers; and (iv) calcium channel blockers;

4) immunosuppressive agents, for example, cyclosporine, azathioprine, and methotrexate; anti-inflammatory corticosteroids; and 5) anti-infective agents, e.g., antibiotics and antivirals.

DEFINITIONS

The following definitions apply to terms as used herein.

The term "alkyl", unless otherwise specified, refers to a monoradical branched or unbranched saturated hydrocarbon chain having from 1 to 20 carbon atoms. Alkyl groups can be optionally interrupted by atoms or groups independently selected from oxygen, sulfur, a phenylene, sulphinyl, sulphonyl, group or —$NR_\alpha$—, wherein $R_\alpha$ can be hydrogen, alkyl, cycloalkyl, alkenyl, cycloalkenyl, alkynyl, aryl, acyl, aralkyl, —C(=O)$OR_\lambda$, $SO_mR_\psi$, or —C(=O)$NR_\lambda R_\pi$. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, aryl, heterocyclyl, heteroaryl, (heterocyclyl)alkyl, cycloalkoxy, —CH=N—O ($C_{1-6}$ alkyl), —CH=N—NH($C_{1-6}$alkyl), —CH=N—NH ($C_{1-6}$alkyl)-$C_{1-6}$alkyl, arylthio, thiol, alkylthio, aryloxy, nitro, aminosulfonyl, aminocarbonylamino, —NHC(=O)$R_\lambda$, —$NR_\lambda R_\pi$, —C(=O)$NR_\lambda R_\pi$, —NHC(=O)$NR_\lambda R_\pi$, —C(=O)heteroaryl, C(=O)heterocyclyl, —O—C(=O) $NR_\lambda R_\pi$ {wherein $R_\lambda$ and $R_\pi$ are independently selected from hydrogen, halogen, hydroxy, alkyl, alkenyl, alkynyl, alkenyl, alkoxy, cycloalkyl, cycloalkenyl, aryl, aralkyl, heterocyclyl, heteroaryl, heterocyclylalkyl, heteroarylalkyl, or carboxy}, nitro, or —$SO_mR_\psi$ (wherein m is an integer from 0-2 and $R_\psi$ is hydrogen, alkyl, alkenyl, alkynyl, cycloalkyl, aralkyl, aryl, heterocyclyl, heteroaryl, heteroarylalkyl, or heterocyclylalkyl). Unless otherwise constrained by the definition, alkyl substituents may be further substituted by 1-3 substituents selected from alkyl, alkenyl, alkynyl, carboxy, —$NR_\lambda R_\pi$, —C(=O)$NR_\lambda R_\pi$, —OC(=O)$NR_\lambda R_\pi$, —NHC(=O) $NR_\lambda R_\pi$, hydroxy, alkoxy, halogen, $CF_3$, cyano, and —$SO_mR_\psi$; or an alkyl group also may be interrupted by 1-5 atoms of groups independently selected from oxygen, sulfur or —$NR_\alpha$— (wherein $R_\alpha$, $R_\lambda$, $R_\pi$, m, and $R_\psi$ are the same as defined earlier). Unless otherwise constrained by the definition, all substituents may be substituted further by 1-3 substituents selected from alkyl, alkenyl, alkynyl, carboxy, carboxyalkyl, —$NR_\lambda R_\pi$, —C(=O)$NR_\lambda R_\pi$, —O—C(=O) $NR_\lambda R_\pi$, hydroxy, alkoxy, halogen, $CF_3$, cyano, and —$SO_mR_\psi$ (wherein $R_\lambda$, $R_\pi$, m, and $R_\psi$ are the same as defined earlier); or an alkyl group as defined above that has both substituents as defined above and is also interrupted by 1-5 atoms or groups as defined above.

The term "alkenyl", unless otherwise specified, refers to a monoradical of a branched or unbranched unsaturated hydrocarbon group having from 2 to 20 carbon atoms with cis, trans or geminal geometry. Alkenyl groups can be optionally interrupted by atoms or groups independently chosen from oxygen, sulfur, phenylene, sulphinyl, sulphonyl and —$NR_\alpha$— (wherein $R_\alpha$ is the same as defined earlier). In the event that alkenyl is attached to a heteroatom, the double bond cannot be alpha to the heteroatom. Alkenyl groups may be substituted further with one or more substituents selected from alkyl, alkenyl, alkynyl, alkoxy, cycloalkyl, cycloalkenyl, acyl, acylamino, acyloxy, —NHC(=O)$R_\lambda$, —$NR_\lambda R_\pi$, —C(=O)$NR_\lambda R_\pi$, —NHC(=O)$NR_\lambda R_\pi$, —O—C(=O)$NR_\lambda R_\pi$, alkoxycarbonylamino, azido, cyano, halogen, hydroxy, oxo, keto, carboxyalkyl, thiocarbonyl, carboxy, arylthio, thiol, alkylthio, aryl, aralkyl, aryloxy, heterocyclyl, heteroaryl, heterocyclyl alkyl, heteroaryl alkyl, aminosulfonyl, aminocarbonylamino, alkoxyamino, hydroxyamino, alkoxyamino, nitro, or $SO_mR_\psi$ (wherein $R_\lambda$, $R_\pi$, m and $R_\psi$ are as defined earlier). Unless otherwise constrained by the definition, alkenyl substituents optionally may be substituted further by 1-3 substituents selected from alkyl, alkenyl, alkynyl, carboxy, hydroxy, alkoxy, halogen, —$CF_3$, cyano, —$NR_\lambda R_\pi$, —C(=O)$NR_\lambda R_\pi$, —O—C(=O)$NR_\lambda R_\pi$, and —$SO_mR_\psi$ (wherein $R_\lambda$, $R_\pi$, m, and $R_\psi$ are as defined earlier). Groups, such as ethenyl or vinyl (CH=$CH_2$), 1-propylene, allyl (—$CH_2$CH=$CH_2$), iso-propylene (—C($CH_3$)=$CH_2$), bicyclo[2.2.1]heptene, and the like, exemplify this term.

The term "alkynyl", unless otherwise specified, refers to a monoradical of an unsaturated hydrocarbon, having from 2 to 20 carbon atoms. Alkynyl groups can be optionally interrupted by atoms or groups independently chosen from oxygen, sulfur, phenylene, sulphinyl, sulphonyl, and —$NR_\alpha$— (wherein $R_\alpha$ is the same as defined earlier). In the event that alkynyl groups are attached to a heteroatom, the triple bond cannot be alpha to the heteroatom. Alkynyl groups may be substituted further with one or more substituents selected from alkyl, alkenyl, alkoxy, cycloalkyl, cycloalkenyl, acyl, acylamino, acyloxy, alkoxycarbonylamino, azido, cyano, halogen, hydroxy, keto, oxo, thiocarbonyl, carboxy, carboxyalkyl, arylthio, thiol, alkylthio, aryl, aralkyl, aryloxy, aminosulfonyl, aminocarbonylamino, hydroxyamino, alkoxyamino, nitro, heterocyclyl, heteroaryl, heterocyclylalkyl, heteroarylalkyl, —NHC(=O)$R_\lambda$, —NR$_\lambda$R$_\pi$, —NHC(=O)NR$_\lambda$R$_\pi$, —C(=O)NR$_\lambda$R$_\pi$, —O—C(=O)NR$_\lambda$R$_\pi$ or —SO$_m$R$_\psi$, (wherein R$_\lambda$, R$_\pi$, m, and R$_\psi$ are the same as defined earlier). Unless otherwise constrained by the definition, alkynyl substituents optionally may be substituted further by 1-3 substituents selected from alkyl, alkenyl, alkynyl, carboxy, carboxyalkyl, hydroxy, alkoxy, halogen, CF$_3$, —NR$_\lambda$R$_\pi$, —C(=O)NR$_\lambda$R$_\pi$, —NHC(=O)NR$_\lambda$R$_\pi$, —C(=O)NR$_\lambda$R$_\pi$, cyano, or —SO$_m$R$_\psi$ (wherein R$_\lambda$, R$_\pi$, m, and R$_\psi$ are the same as defined earlier).

The term "cycloalkyl", unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentenyl, and the like, or multiple ring structures, including adamantanyl, bicyclo[2.2.1]heptane, or cyclic alkyl groups to which is fused an aryl group, for example, indane and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, —NR$_\lambda$R$_\pi$, —NHC(=O)NR$_\lambda$R$_\pi$, —NHC(=O)R$_\lambda$, —C(=O)NR$_\lambda$R$_\pi$, —O—C(=O)NR$_\lambda$R$_\pi$, nitro, heterocyclyl, heteroaryl, heterocyclylalkyl, heteroarylalkyl, or SO$_m$R$_\psi$ (wherein R$_\lambda$, R$_\pi$, m, and R$_\psi$ are the same as defined earlier). Unless otherwise constrained by the definition, cycloalkyl substituents optionally may be substituted further by 1-3 substituents selected from alkyl, alkenyl, alkynyl, carboxy, hydroxy, alkoxy, halogen, CF$_3$, —NR$_\lambda$R$_\pi$, —NHC(=O)NR$_\lambda$R$_\pi$, —NHC(=O)NR$_\lambda$R$_\pi$, —OC(=O)NR$_\lambda$R$_\pi$, cyano, or —SO$_m$R$_\psi$ (wherein R$_\lambda$, R$_\pi$, m, and R$_\psi$ are the same as defined earlier). "Cycloalkylalkyl" refers to alkyl-cycloalkyl group linked through alkyl portion, wherein the alkyl and cycloalkyl are the same as defined earlier.

The term "aralkyl", unless otherwise specified, refers to alkyl-aryl linked through an alkyl portion (wherein alkyl is as defined above) and the alkyl portion contains 1 to 6 carbon atoms and aryl is as defined below. Examples of aralkyl groups include benzyl, ethylphenyl, propylphenyl, naphthylmethyl, and the like.

The term "aryl", unless otherwise specified, refers to aromatic system having 6 to 14 carbon atoms, wherein the ring system can be mono-, bi-, or tricyclic and are carbocyclic aromatic groups. For example, aryl groups include, but are not limited to, phenyl, biphenyl, anthryl, or naphthyl ring and the like, optionally substituted with 1 to 3 substituents selected from halogen (e.g., F, Cl, Br, I), hydroxy, alkyl, alkenyl, alkynyl, cycloalkyl, alkoxy, acyl, aryloxy, CF$_3$, cyano, nitro, COOR$_\psi$, NHC(=O)R$_\lambda$, —NR$_\lambda$R$_\pi$, —C(=O)NR$_\lambda$R$_\pi$, —NHC(=O)NR$_\lambda$R$_\pi$, —O—C(=O)NR$_\lambda$R$_\pi$, —SO$_m$R$_\psi$, carboxy, heterocyclyl, heteroaryl, heterocyclylalkyl, heteroarylalkyl or amino carbonyl amino, mercapto, haloalkyl, optionally substituted aryl, optionally substituted heterocyclylalkyl, thioalkyl, —CONHR$_\pi$, —OCOR$_\pi$, —COR$_\pi$, —NHSO$_2$R$_\pi$, or —SO$_2$NHR$_\pi$ (wherein R$_\lambda$, R$_\pi$, m, and R$_\psi$ are the same as defined earlier). Aryl groups optionally may be fused with a cycloalkyl group, wherein the cycloalkyl group may optionally contain heteroatoms selected from O, N, or S. Groups such as phenyl, naphthyl, anthryl, biphenyl, and the like exemplify this term.

The term "aryloxy" denotes the group O-aryl wherein aryl is the same as defined above.

The term "heteroaryl", unless otherwise specified, refers to an aromatic ring structure containing 5 or 6 ring atoms or a bicyclic or tricyclic aromatic group having from 8 to 10 ring atoms, with one or more heteroatoms independently selected from N, O, or S optionally substituted with 1 to 4 substituents selected from halogen (e.g., F, Cl, Br, I), hydroxy, alkyl, alkenyl, alkynyl, cycloalkyl, acyl, carboxy, aryl, alkoxy, aralkyl, cyano, nitro, heterocyclyl, heteroaryl, —NR$_\lambda$R$_\pi$, CH=NOH, —(CH$_2$)$_w$C(=O)R$_\eta$ {wherein w is an integer from 0 to 4 and R$_\eta$ is hydrogen, hydroxy, OR$_\lambda$, NR$_\lambda$R$_\pi$, —NHOR$_\omega$, or —NHOH}, —C(=O)NR$_\lambda$R$_\pi$—NHC(=O)NR$_\lambda$R$_\pi$, —SO$_m$R$_\psi$, —O—C(=O)NR$_\lambda$R$_\pi$, —O—C(=O)R$_\lambda$, or —O—C(=O)OR$_\lambda$ (wherein m, R$_\psi$, R$_\lambda$, and R$_\pi$ are as defined earlier and R$_\omega$ is alkyl, cycloalkyl, aryl, heteroaryl, heterocyclyl, heteroarylalkyl, or heterocyclylalkyl). Unless otherwise constrained by the definition, the substituents are attached to a ring atom, i.e., carbon or heteroatom in the ring. Examples of heteroaryl groups include oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzthiazinyl, benzthiazinonyl, benzoxazinyl, benzoxazinonyl, quinazonyl, carbazolyl phenothiazinyl, phenoxazinyl, benzothiazolyl, or benzoxazolyl, and the like.

The term "heterocyclyl", unless otherwise specified, refers to a non-aromatic monocyclic or bicyclic cycloalkyl group having 5 to 10 atoms wherein 1 to 4 carbon atoms in a ring are replaced by heteroatoms selected from O, S, or N, and optionally are benzofused or fused with a heteroaryl having 5 to 6 ring members and/or optionally are substituted, wherein the substituents are selected from halogen (e.g., F, Cl, Br, I), hydroxy, alkyl, alkenyl, alkynyl, cycloalkyl, acyl, optionally substituted aryl, alkoxy, alkaryl, cyano, nitro, oxo, carboxy, optionally substituted heterocyclyl, optionally substituted heterocyclylalkyl, optionally substituted heteroaryl, —O—C(=O)Rλ, —O—C(=O)ORλ, —C(=O)NRλRπ, SOmRψ, —O—C(=O)NRλRπ, —NHC(=O)NRλRπ, —NRλRπ, mercapto, haloalkyl, thioalkyl, —COORψ, —COONHRλ, —CORλ, —NHSO2Rλ, or SO2NHRλ (wherein m, Rψ, Rλ, and Rπ are as defined earlier) or guanidine. Heterocyclyl can optionally include rings having one or more double bonds. Such ring systems can be mono-, bi-, or tricyclic. Carbonyl or sulfonyl group can replace carbon atoms of heterocyclyl. Unless otherwise constrained by the definition, the substituents are attached to the ring atom, i.e., carbon or heteroatom in the ring. Also, unless otherwise constrained by the definition, the heterocyclyl ring optionally may contain one or more olefinic bonds. Examples of heterocyclyl groups include benzotriazinone, isoindoledione, pyrimidinedione, aza-spiro[4.5]decanedione, benzo-oxazinedione, imidazolidinedione, phthalazinone, oxazolidinyl, tetrahydrofuranyl, dihydrofuranyl, benzoxazinyl, benzthiazinyl, imidazolyl, benzimidazolyl, tetrazolyl, carbaxolyl, indolyl, phenoxazinyl, phenothiazinyl, dihydropyridinyl, dihydroisoxazolyl, dihydrobenzofuryl, azabicyclohexyl, thiazolidinyl, dihydroindolyl, pyridinyl, isoindole 1,3-dione, piperidinyl, tetrahydropyranyl, piperazinyl, 3H-imidazo[4,5-b]pyridine, isoquinolinyl, 1H-pyrrolo[2,3-b]pyridine, or piperazinyl, and the like.

The term "cycloalkylalkyl" refers to cycloalkyl group linked through alkyl portion, wherein the alkyl having 1 to 6 carbon atoms and cycloalkyl are the same as defined earlier.

The term "heteroarylalkyl" refers to heteroaryl group linked through alkyl portion, wherein the alkyl having 1 to 6 carbon atoms and heteroaryl are the same as defined earlier.

The term "heterocyclylalkyl" refers to heterocyclyl group linked through alkyl portion, wherein the alkyl having 1 to 6 carbon atoms and heterocyclyl are the same as defined earlier.

The term "amino" refers to —$NH_2$.

The term "acyl" refers to —$C(=O)R_4$ wherein $R_4$ is the same as defined earlier.

The term "thioacyl" refers to —$C(=S)R_4$ wherein $R_4$ is the same as defined above.

The term "halogen" refers to fluorine, chlorine, bromine, or iodine.

The term "leaving group" refers to groups that exhibit or potentially exhibit the properties of being labile under the synthetic conditions and also of being readily separated from synthetic products under defined conditions. Examples of leaving groups include, but are not limited to, halogen (e.g., F, Cl, Br, I), triflates, tosylate, mesylates, alkoxy, thioalkoxy, or hydroxy radicals, and the like.

The term "protecting groups" refers to moieties that prevent chemical reaction at a location of a molecule intended to be left unaffected during chemical modification of such molecule. Unless otherwise specified, protecting groups may be used on groups, such as hydroxy, amino, or carboxy. Examples of protecting groups are found in T. W. Greene and P. G. M. Wuts, "Protective Groups in Organic Synthesis", $2^{nd}$ Ed., John Wiley and Sons, New York, N.Y., which is incorporated herein by reference. The species of the carboxylic protecting groups, amino protecting groups, or hydroxy protecting groups employed are not critical, as long as the derivatised moiety/moieties is/are stable to conditions of subsequent reactions and can be removed without disrupting the remainder of the molecule.

Compounds described herein can contain one or more asymmetric carbon atoms and thus occur as diastereomers. These compounds can also exist as conformers/rotamers. All such isomeric forms of these compounds are included herein. Each stereogenic carbon may be of the R or S configuration. Although the specific compounds exemplified in this application may be depicted in a particular stereochemical configuration, compounds having either the opposite stereochemistry at any given chiral center, or mixtures thereof, are envisioned.

The term "pharmaceutically acceptable salts" forming part of this invention includes the salts of carboxylic acid moiety, which may be prepared by reacting the compound with appropriate base to provide corresponding base addition salts. Examples of such bases are alkali metal hydroxides including potassium hydroxide, sodium hydroxide and lithium hydroxide; or alkaline earth metal hydroxides such as magnesium hydroxide and calcium hydroxide. Further, the salts of organic bases such as lysine, arginine, guanidine, ethanolamine, choline, and the like; inorganic bases, e.g., ammonium or substituted ammonium salts are also included. Wherever appropriate, compounds of the present invention may also form the acid addition salts by treating the said compounds with pharmaceutically acceptable organic and inorganic acids, e.g., hydrohalides such as hydrochloride, hydrobromide, or hydroiodide; other mineral acids and their corresponding salts such as sulphate, nitrate, phosphate, etc.; and alkyl and mono-arylsulphonates such as ethane sulphonate, toluene sulphonate, and benzene sulphonate; and other organic acids and their corresponding salts such as acetate, tartarate, maleate, succinate, citrate, etc.

The salt forms differ from the compound described herein in certain physical properties such as solubility, but the salts are otherwise equivalent for the purpose of this invention.

The term "pharmaceutically acceptable solvates" refers to solvates with water (i.e., hydrates) or pharmaceutically acceptable solvents, for example, solvates with ethanol and the like. Such solvates are also encompassed within the scope of the disclosure. Furthermore, some of the crystalline forms for compounds described herein may exist as polymorphs and as such are intended to be included in the scope of the disclosure.

The term "polymorphs" includes all crystalline forms as well as amorphous forms for compounds described herein, and as such are included in the present invention.

The phrase "pharmaceutically acceptable carriers" is intended to include non-toxic, inert solid, semi-solid, or liquid filler, diluent, encapsulating material, or formulation auxiliary of any type.

The term "pharmaceutically acceptable" means approved by regulatory agency of the federal or a state government or listed in the U.S. Pharmacopoeia or other generally recognized pharmacopoeia for use in animals, and more particularly, in humans.

Examples of inflammatory conditions and autoimmune disorders in which the compounds of the invention have potentially beneficial effects in treatment methods may include, but are not limited to, diseases of the respiratory tract such as asthma (including allergen-induced asthmatic reactions), cystic fibrosis, bronchitis (including chronic bronchitis), chronic obstructive pulmonary disease (COPD), adult respiratory distress syndrome (ARDS), chronic pulmonary inflammation, rhinitis and upper respiratory tract inflammatory disorders (URID), ventilator induced lung injury, silicosis, pulmonary sarcoidosis, idiopathic pulmonary fibrosis, bronchopulmonary dysplasia, arthritis, e.g., rheumatoid arthritis, osteoarthritis, infectious arthritis, psoriatic arthritis, traumatic arthritis, rubella arthritis, Reiter's syndrome, gouty arthritis, and prosthetic joint failure, gout, acute synovitis, spondylitis, and non-articular inflammatory conditions, e.g., herniated/ruptured/prolapsed intervertebral disk syndrome, bursitis, tendonitis, tenosynovitic, fibromyalgic syndrome, and other inflammatory conditions associated with ligamentous sprain and regional musculoskeletal strain, inflammatory disorders of the gastrointestinal tract, e.g., ulcerative colitis, diverticulitis, Crohn's disease, inflammatory bowel diseases, irritable bowel syndrome, and gastritis, multiple sclerosis, systemic lupus erythematosus, scleroderma, autoimmune exocrinopathy, autoimmune encephalomyelitis, diabetes, tumor angiogenesis and metastasis, cancer including carcinoma of the breast, colon, rectum, lung, kidney, ovary, stomach, uterus, pancreas, liver, oral, laryngeal, and prostate, melanoma, acute and chronic leukemia, periodontal disease, neurodegenerative disease, Alzheimer's disease, Parkinson's disease, epilepsy, muscle degeneration, inguinal hernia, retinal degeneration, diabetic retinopathy, macular degeneration, inguinal hernia, ocular inflammation, bone resorption diseases, osteoporosis, osteopetrosis, graft vs. host reaction, allograft rejections, sepsis, endotoxemia, toxic shock syndrome, tuberculosis, usual interstitial and cryptogenic organizing pneumonia, bacterial meningitis, systemic cachexia, cachexia secondary to infection or malignancy, cachexia secondary to acquired immune deficiency syndrome (AIDS), malaria, leprosy, leishmaniasis, Lyme disease, glomerulonephritis, glomerulosclerosis, renal fibrosis, liver fibrosis, pancrealitis, hepatitis, endometriosis, pain, e.g., that associated with inflammation and/or trauma, inflammatory diseases of the skin, e.g., dermatitis, dermatosis, skin ulcers, psoriasis, eczema, systemic vasculitis, vascular dementia, thrombosis, atherosclerosis, restenosis, reperfusion injury, plaque calcification, myocarditis, aneurysm, stroke, pulmonary hypertension, left ventricular remodeling, and heart failure. It will be appreciated by those skilled in the art that reference herein to treatment extends to prophylaxis as well as the treatment of established conditions.

Compounds disclosed herein may be prepared, for example, by techniques well known in the organic synthesis and familiar to a practitioner ordinarily skilled in art of this invention. In addition, the processes described herein may enable the synthesis of the compounds of the present invention. However, these may not be the only means by which the compounds described in the invention may be synthesized. Further, the various synthetic steps described herein may be performed in alternate sequences in order to furnish the desired compounds.

converted to a compound of Formula VI (wherein E is an alkyl group such as methyl, ethyl, and the like), which can then be hydrogenated to form compounds of Formulae VIIa and VIIb. Compounds of Formulae VIIa and VIIb can be reduced to form compounds of Formulae VIIIa and VIIIb.

Silylation of a compound of Formula II to form a compound of Formula III can be carried out with silylating reagents such as, for example, tert-butyldimethylchlorosilane, triphenylchlorosilane, t-butyldiphenylchlorosilane in the presence of a base, for example, imidazole or triethylamine in an organic solvent, for example, dimethyl formamide, dimethylsulphoxide or acetonitrile.

Acetonation of a compound of Formula III to form a compound of Formula IV can be carried out with excess acetone as a solvent, in the presence of a mild acid catalyst, for example, anhydrous copper (II) sulphate and camphorsulphonic acid, anhydrous zinc chloride and a small amount of phosphoric acid, or anhydrous ferric chloride. Alternately, one may utilize trans-acetonation with dimethoxypropane in the presence of acid catalysts such as p-toluenesulfonic acid, sulfuric acid, or montmorillonite-K.

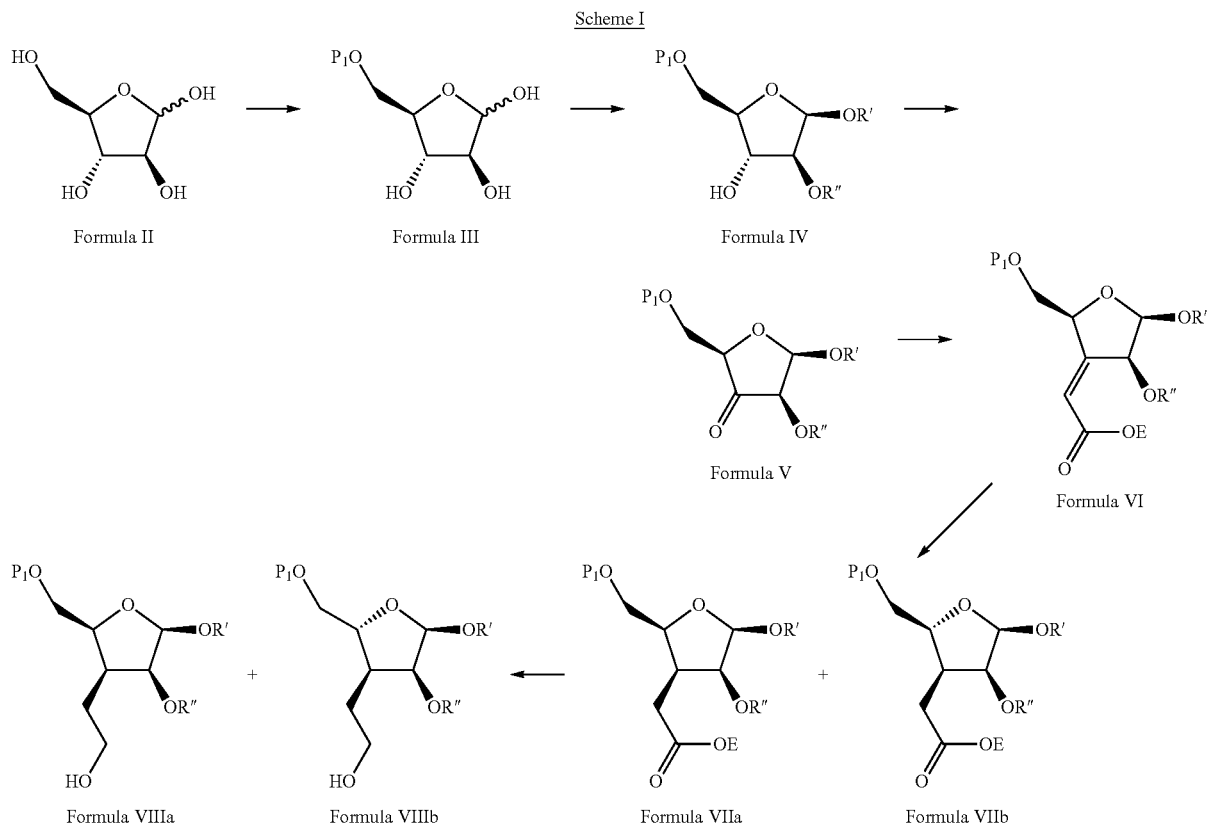

Scheme I

Compounds of Formulae VIIIa and VIIIb can be prepared by following, for example, synthetic routes as depicted in Scheme I. Thus, a compound of Formula II can be converted to a compound of Formula III (wherein $P_1$ is a silyl protecting group for example, tert-butyldimethylsilane, tert-butyldiphenylsilane, or triisopropylsilane), which can then be converted to a compound of Formula IV (wherein $P_1$ is defined as above and R' and R" together form an acetal protecting group, for example, isopropylidene or cyclohexylidene acetal). The compound of Formula IV can be oxidized to form a compound of Formula V. The compound of Formula V can then be The compound of Formula IV can be oxidized to form a compound of Formula V, for example, by using Swern oxidation (dimethylsulphoxide and oxalyl chloride) or Corey-Kim oxidation (N-chlorosuccinimide and dimethylsulphide) in the presence of a base, for example, triethylamine, diisopropylethylamine in a solvent, for example, dichloromethane or toluene. Alternatively, the compound of Formula IV can be oxidized to a compound of Formula V in, for example, dichloromethane or chloroform with an oxidizing agent, such as Dess-Martin reagent, pyridinium chlorochromate (PCC), or pyridinium dichromate (PDC). Oxidation of the compound of Formula IV to form a compound of Formula V can also be carried out catalytically using, for example, 2,2,6,6-tetramethylpiperidine N-oxyl (TEMPO) and the 4-substituted derivatives thereof, including, for example, 4-methoxy-TEMPO, 4-ethoxy-TEMPO, 4-acetoxy-TEMPO, 4-acetamino-TEMPO, 4-hydroxy-TEMPO, 4-benzoyloxy-TEMPO, 4-amino-TEMPO, N,N-dimethylamino-TEMPO, or 4-oxo-TEMPO as a catalyst, in the presence of a co-catalyst, for example, potassium bromide or sodium bromide, with an oxidant, for example, sodium hypochlorite, potassium hypochlorite, calcium hypochlorite, sodium hypobromite, or potassium hypobromite in a solvent, for example, methylene chloride, chloroform, ethyl acetate, butyl acetate, acetonitrile, tetrahydrofuran, toluene, acetone, diethyl ether, methyl tert-butyl ether, pentane, hexane, or mixtures of such solvents.

The compound of Formula V can be converted to a compound of Formula VI, for example, via a Horner-Wadsworth-Emmons reaction, thus a compound of Formula V can be reacted with phosphonate carbanions produced in situ by treating trimethylphosphonoacetate or triethylphosphonoacetate with a base, for example, sodium hydride, potassium hydride, potassium tert-butoxide, sodium tert-butoxide, potassium carbonate, triethylamine in an organic solvent, for example, tetrahydrofuran or dimethoxyethane to give a compound of Formula VI. Alternately, the Wittig reaction can be carried out using the preformed Wittig reagent such as (carboethoxymethylene)-triphenylphosphorane.

Hydrogenation of a compound of Formula VI to form compounds of Formulae VIIa and VIIb can be carried with palladium on carbon in the presence of hydrogen, in a suitable solvent, for example, methanol, ethanol, propanol, tetrahydrofuran, ethyl acetate, or mixtures thereof.

Compounds of Formulae VIIa and VIIb can be reduced to give compounds of Formula VIIIa and VIIIb in the presence of a reducing agent, for example, lithium aluminum hydride, lithium triethyl borohydride, or sodium borohydride, in the presence of an additive, for example, lithium chloride or aluminum chloride, in an organic solvent, for example, tetrahydrofuran, diethylether, or diglyme.

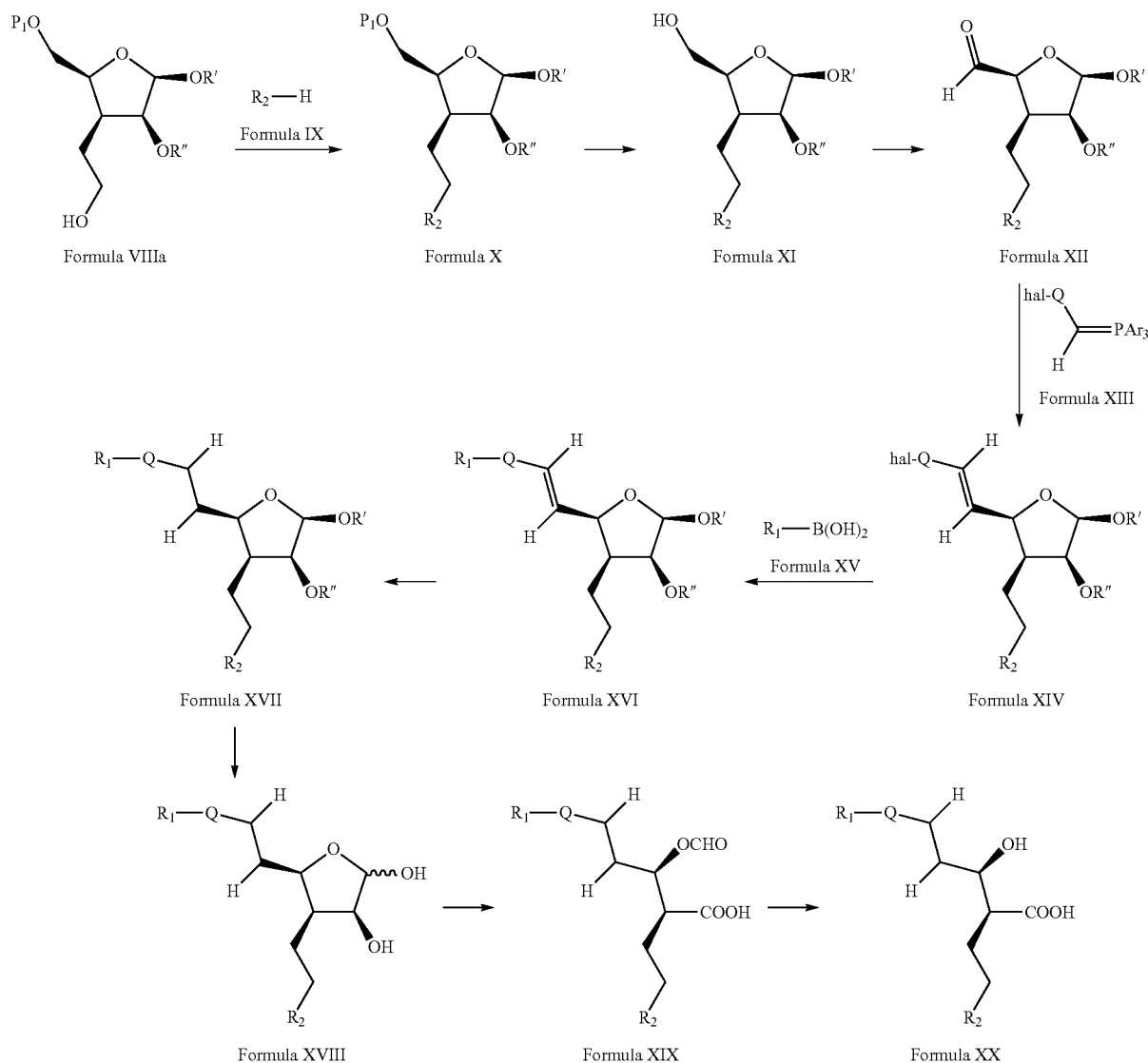

Scheme II

Compounds of Formula XX can be prepared, for example, by following synthetic routes as depicted in Scheme II. Thus, a compound of Formula VIIIa (wherein $P_1$, R', and R" are same as defined earlier), can react with a compound of Formula IX (wherein $R_2$ is an N-containing heterocyclyl or heteroaryl) to give a compound of Formula X. The compound of Formula X can undergo deprotection to form a compound of Formula XI which, on oxidation, can give a compound of Formula XII. The compound of Formula XII on reaction with a compound of Formula XIII (wherein Q is same as defined earlier, hal is Cl, Br, or I and Ar is phenyl) can form a compound of Formula XIV. The compound of Formula XIV can then react with a compound of Formula XV (wherein $R_1$ is same as defined earlier) to form a compound of Formula XVI which can then be hydrogenated to form a compound of Formula XVII. The compound of Formula XVII can undergo deprotection to form a compound of Formula XVIII which can then be oxidatively cleaved to form a compound of Formula XIX. The compound of Formula XIX can be deformylated to form a compound of Formula XX.

The reaction of a compound of Formula VIIIa with a compound of Formula IX to give a compound of Formula X can be carried out using triphenylphosphine or tributylphosphine and diethyl azodicarboxylate, diisoproyl azodicarboxylate, or 1,1'-azodicarbonyldipiperidine in an organic solvent, for example, tetrahydrofuran, dimethylformamide, or toluene.

The compound of Formula X can be deprotected to form a compound of Formula XI with deprotecting agents, for example, tetrabutylammonium fluoride or potassium fluoride in an organic solvent, for example, tetrahydrofuran, dimethylformamide, diethyl ether, or dioxane, optionally in the presence of crown ethers such as, for example, 18-crown-6. The oxidation of a compound of Formula XI to give a compound of Formula XII can be carried out similarly to the oxidation of a compound of Formula IV to form a compound of Formula V.

The compound of Formula XII can be converted to a compound of Formula XIV by reacting with a compound of Formula XIII (Wittig reagent, i.e., an ylide, prepared by reacting a phosphonium salt, in turn prepared from triphenylphosphine and alkyl halide, in a solvent, for example, tetrahydrofuran, dimethyl sulphoxide, or diethyl ether, with a strong base, for example, n-butyllithium, sodium hydride, or potassium tert-butoxide).

The reaction of a compound of Formula XIV with a compound of Formula XV can be carried out in the presence of a metal catalyst, for example, tetrakis(triphenylphosphine) palladium (0), tetrakis(tricyclohexylphosphine) palladium (0), tetrakis(tri-tert-butylphosphine) palladium (0), or palladium acetate and triphenylphosphine in the presence of a base, for example, potassium carbonate or cesium carbonate, in an organic solvent, for example, toluene, dimethyl sulphoxide, dimethylformamide, tetrahydrofuran, dioxane, or diethyl ether.

Hydrogenation of a compound of Formula XVI to form a compound of Formula XVII can be carried out similarly to hydrogenation of a compound of Formula VI to compounds of Formulae VIIa and VIIb.

The compound of Formula XVII can be deprotected to form a compound of Formula XVIII with perchloric acid, acetic acid, or hydrochloric acid in solvent(s), for example, acetonitrile, water, tetrahydrofuran, or mixtures thereof.

Conversion of a compound of Formula XVIII to form a compound of Formula XIX can be carried out by diol cleavage in the presence of, for example, sodium metaperiodate, lead tetraacetate, pyridinium chlorochromate, or manganese dioxide, in co-solvents, for example, tert-butanol-water, methanol-tetrahydrofuran, or tert-butanol-tetrahydrofuran, followed by oxidation with, for example, potassium permanganate or with a mixture of sodium dihydrogen phosphate, sodium chlorite, and hydrogen peroxide.

The compound of Formula XIX can be deformylated to form a compound of Formula XX in the presence of a base for example, potassium carbonate, sodium carbonate, or triethylamine in a solvent, for example, methanol, tetrahydrofuran, or mixtures thereof.

Scheme III

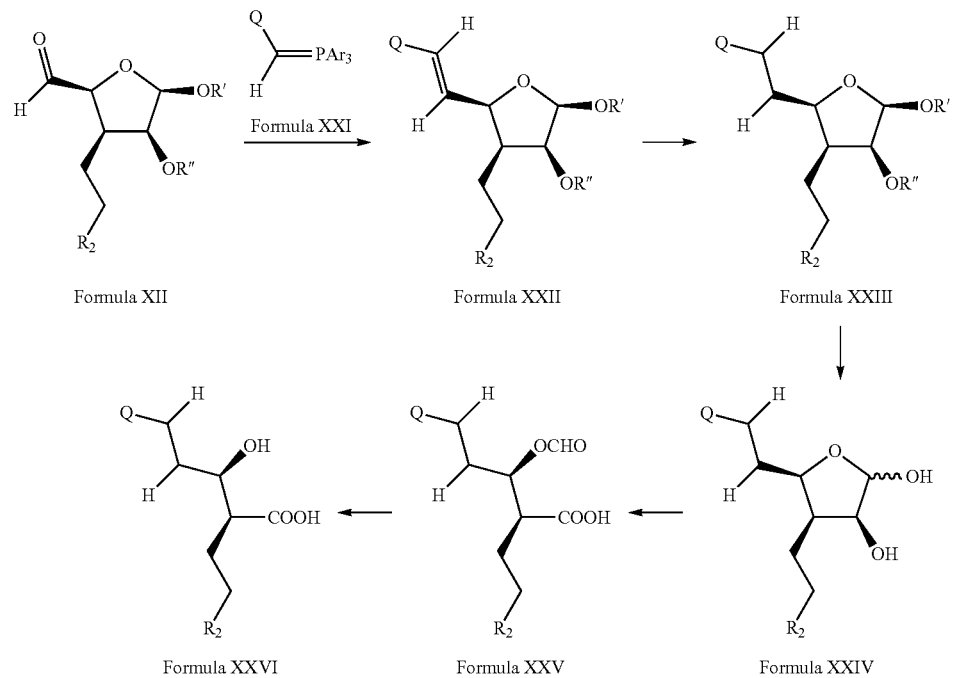

Compounds of Formula XXVI can be prepared by following synthetic routes, for example, as depicted in Scheme III. Thus, a compound of Formula XII can react with a compound of Formula XXI (wherein Q is same as defined earlier and Ar is phenyl) to form a compound of Formula XXII (wherein $R_2$ is an N-containing heterocyclyl or heteroaryl), which can further be hydrogenated to form a compound of Formula XXIII. The compound of Formula XXIII can be deprotected to form a compound of Formula XXIV, which can then be oxidatively cleaved to give a compound of Formula XXV. The compound of Formula XXV can then be deformylated to form a compound of Formula XXVI.

The reaction of a compound of Formula XII with a compound of Formula XXI to form a compound of Formula XXII can be carried out similarly to reaction of a compound of Formula XII to a compound of Formula XIV. Hydrogenation of a compound of Formula XXII to give a compound of Formula XXIII can be carried out under similar conditions as that of hydrogenation of a compound of Formula VI to compounds of Formulae VIIa and VIIb.

Deprotection of a compound of Formula XXIII to give a compound of Formula XXIV can be carried out similarly to deprotection of a compound of Formula XVII to a compound of Formula XVIII. The oxidative cleavage of a compound of Formula XXIV to form a compound of Formula XXV can be carried out under similar condition as that of cleavage of a compound of Formula XVIII to a compound of Formula XIX.

Deformylation of a compound of Formula XXV to form a compound of Formula XXVI can be carried out similarly to deformylation of a compound of Formula XIX to give a compound of Formula XX.

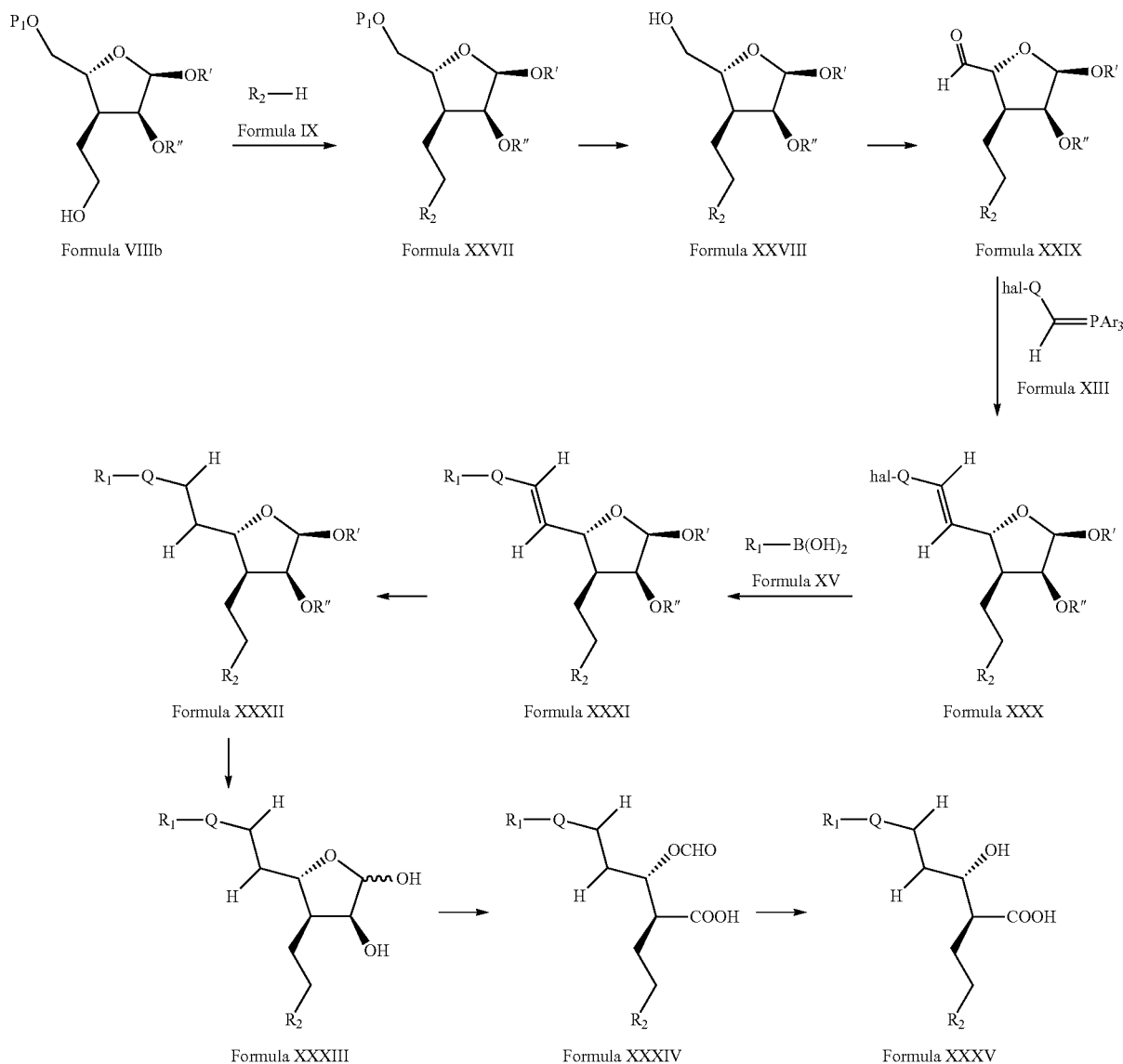

Compounds of Formula XXXV can be prepared by, for example, following synthetic routes as depicted in Scheme IV. Thus, a compound of Formula VIIIb (wherein $P_1$, R', and R" are the same as defined earlier), can react with a compound of Formula IX (wherein $R_2$ is an N-containing heterocyclyl or heteroaryl) to give a compound of Formula XXVII. The compound of Formula XXVII can be deprotected to form a compound of Formula)(XVIII, which on oxidation can give a compound of Formula XXIX. The compound of Formula XXIX on reaction with a compound of Formula XIII can form a compound of Formula XXX which can then react with a compound of Formula XV (wherein $R_1$ is same as defined earlier) to form a compound of Formula XXXI. The compound of Formula XXXI can then be hydrogenated to form a compound of Formula XXXII which can then undergo deprotection to form a compound of Formula XXXIII. The compound of Formula XXXIII can be oxidatively cleaved to form a compound of Formula XXXIV. The compound of Formula XXXIV can then be deformylated to form a compound of Formula XXXV.

The reaction of a compound of Formula VIIIb with a compound of Formula IX to give a compound of Formula XXVII can be carried out similarly to the reaction of a compound of Formula VIIIa to form a compound of Formula X.

Deprotection of a compound of Formula XXVII to give a compound of Formula XXVIII can be carried out similarly to the deprotection of a compound of Formula X to form a compound of Formula XI.

Oxidation of a compound of Formula XXVIII to give a compound of Formula XXIX can be carried out similarly to the oxidation of a compound of Formula IV to form a compound of Formula V.

The reaction of a compound of Formula XXIX with a compound of Formula XIII to form a compound of Formula XXX can be carried out under similar condition as that of reaction of a compound of Formula XII to form a compound of Formula XIV.

Coupling of a compound of Formula XXX with a compound of Formula XV to form a compound of Formula XXXI can be carried out similarly to the coupling of a compound of Formula XIV to form a compound of Formula XVI.

Hydrogenation of a compound of Formula XXXI to form a compound of Formula XXXII can be carried out similarly to hydrogenation of a compound of Formula VI to form compounds of Formulae VIIa and VIIb. The compound of Formula XXXII can be deprotected to form a compound of Formula XXXIII under similar conditions as that of deprotection of a compound of Formula XVII to form a compound of Formula XVIII.

Oxidative cleavage of a compound of Formula XXXIII to form a compound of Formula XXXIV can be carried out similarly to cleavage of a compound of Formula XVIII to give a compound of Formula XIX.

Deformylation of a compound of Formula XXXIV to form a compound of Formula XXXV can be carried out under similar conditions as that of the deformylation of a compound of Formula XIX to form a compound of Formula XX.

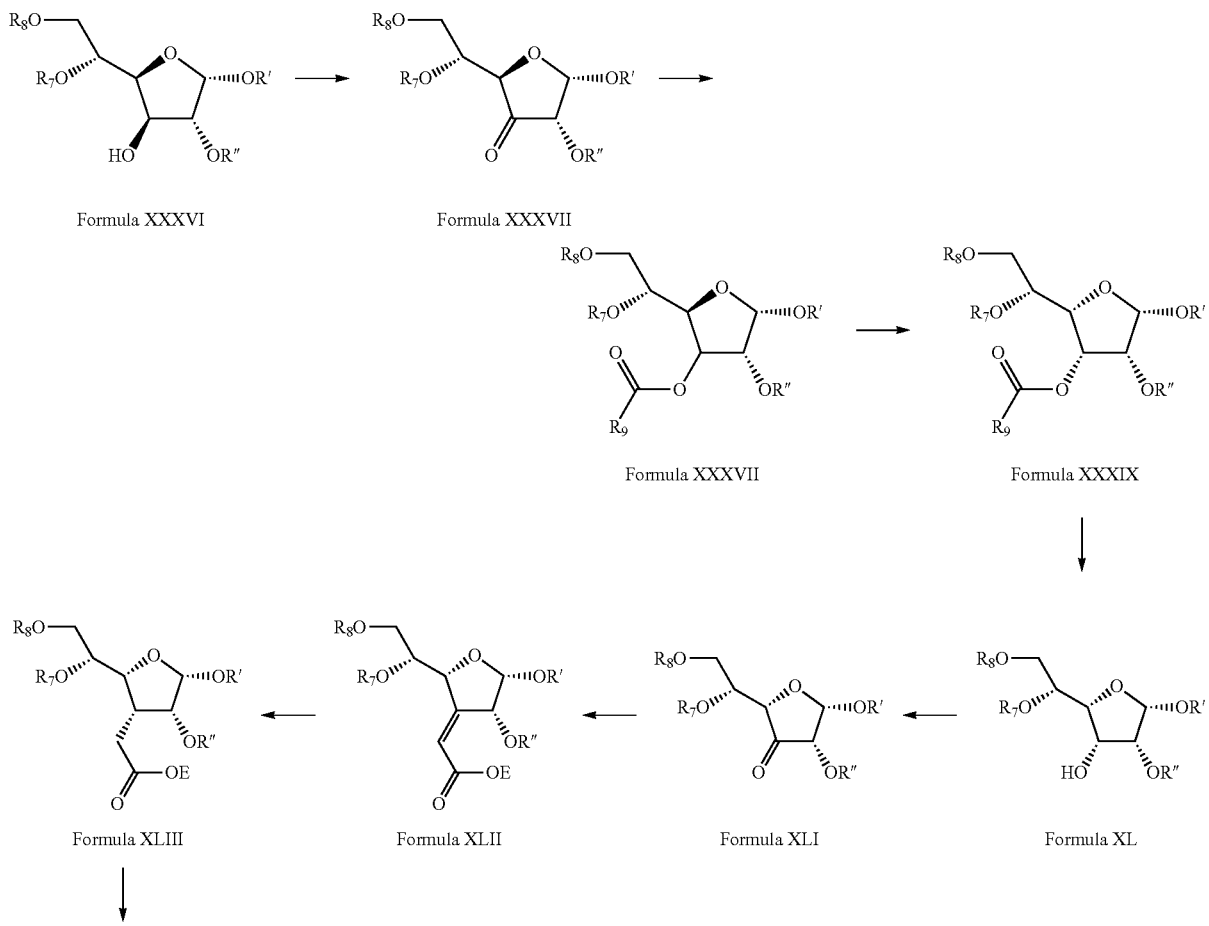

Scheme V

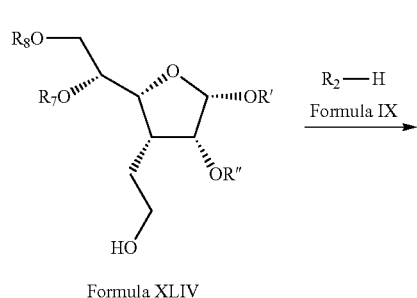

Formula XLIV

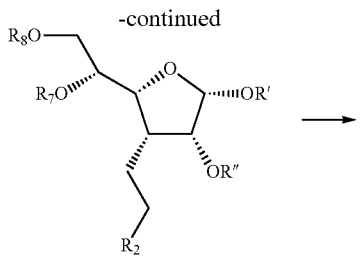

Formula XLV

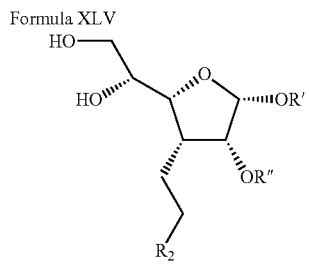

Formula XLVI

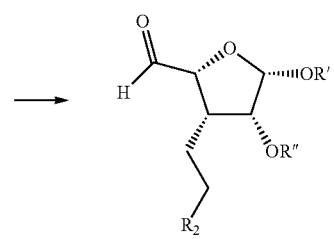

Formula XLVII

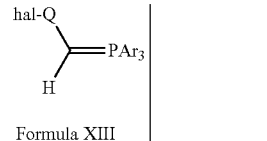

Formula XIII

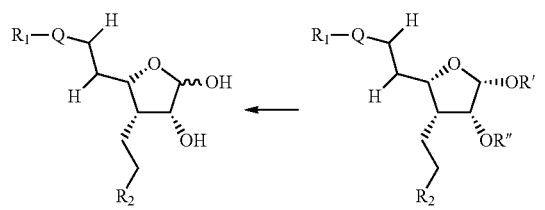

Formula LI     Formula L     Formula XLIX     Formula XLVIII

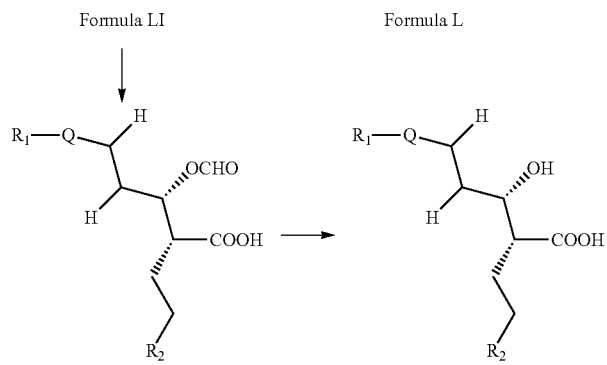

Formula LII     Formula LIII

Compounds of Formula LIII can be prepared, for example, by following synthetic routes as depicted in Scheme V. Thus, a compound of Formula XXXVI (wherein $R_7$ and $R_8$ together form a acetal protecting group, for example, isopropylidene acetal, and R' and R" are the same as described earlier) can be oxidized to form a compound of Formula XXXVII which can then be converted to form a compound of Formula XXXVIII (wherein $R_9$ is alkyl or aryl). The compound of Formula XXXVIII can be hydrogenated to give a compound of Formula XXXIX which can then be hydrolyzed to give a compound of Formula XL. The compound of Formula XL can be oxidized to give a compound of Formula XLI which can then be converted to form a compound of Formula XLII. The compound of Formula XLII can be hydrogenated to form a compound of Formula XLIII which can then be reduced to form a compound of Formula XLIV. The compound of Formula XLIV can then be reacted with a compound of Formula IX (wherein $R_2$ is an N-containing heterocyclyl or heteroaryl) to afford a compound of Formula XLV which can then be deprotected to form a compound of Formula XLVI. The compound of Formula XLVI can be oxidized to form a compound of Formula XLVII which can then react with a compound of Formula XIII to form a compound of Formula XLVIII. The compound of Formula XLVIII can then be reacted with a compound of Formula XV (wherein $R_1$ is same as defined earlier) to give a compound of Formula XLIX which can then be hydrogenated to form a compound of Formula L. The compound of Formula L is deprotected to form a compound of Formula LI which can then be oxidatively cleaved to form a compound of Formula LII. The compound of Formula LII is then deformylated to form a compound of Formula LIII.

Oxidation of a compound of Formula)(XXVI to form a compound of Formula XXXVII can be carried out under similar condition as that of oxidation of a compound of Formula IV to form a compound of Formula V. The compound of Formula XXXVII can be converted to a compound of Formula XXXVIII in the presence of, for example, acetic anhydride or benzoic anhydride in presence of base, such as, for example, pyridine, triethylamine, or morpholine.

The compound of Formula XXXVIII can be hydrogenated to form a compound of Formula XXXIX similarly to the hydrogenation of a compound of Formula VI to give compounds of Formulae VIIa and VIIb. The hydrolysis of a compound of Formula XXXIX to form a compound of Formula XL can be carried out with a base, for example, sodium hydroxide, potassium hydroxide, sodium carbonate, potassium carbonate, or sodium methoxide in the presence of a solvent, for example, methanol, ethanol, or isopropanol. The compound of Formula XL can be oxidized to form a compound of Formula XLI similarly to the oxidation of a compound of Formula IV to form a compound of Formula V.

Conversion of a compound of Formula XLI to form a compound of Formula XLII can be carried out under similar condition as that of conversion of a compound of Formula V to form a compound of Formula VI. The compound of Formula XLII can be hydrogenated to form a compound of Formula XLIII similarly to the hydrogenation of a compound of Formula VI to compounds of Formulae VIIa and VIIb. The reduction of a compound of Formula XLIII to form a compound of Formula XLIV can be carried out under similar condition as that of reduction of compounds of Formulae VIIa and VIIb to form compounds of Formulae VIIIa and VIIIb. The reaction of a compound of Formula XLIV with a compound of Formula IX to form a compound of Formula XLV can be carried out similarly to the reaction of a compound of Formula VIIIa to form a compound of Formula X.

Selective acetonide deprotection of a compound of Formula XLV to form a compound of Formula XLVI can be carried out with perchloric acid in a solvent, for example, tetrahydrofuran or diethyl ether or trifluoroacetic acid in dichloromethane. Oxidation of a compound of Formula XLVI to form a compound of Formula XLVII can be carried out with, for example, sodium metaperiodate, lead tetraacetate, pyridinium chlorochromate, or manganese dioxide in a solvent, for example, acetone, methanol, ethanol, or tert-butanol.

The reaction of a compound of Formula XLVII with a compound of Formula XIII to form a compound of Formula XLVIII can be carried out similarly to the reaction of a compound of Formula XII to form a compound of Formula XIV. Coupling of a compound of Formula XLVIII with a compound of Formula XV to form a compound of Formula XLIX can be carried out similarly to the coupling of a compound of Formula XIV to form a compound of Formula XVI. The compound of Formula XLIX can be hydrogenated to form a compound of Formula L under similar conditions to the hydrogenation of a compound of Formula VI to compounds of Formulae VIIa and VIIb. Deprotection of a compound of Formula L to give a compound of Formula LI can be carried out under similar conditions to the deprotection of a compound of Formula XVII to form a compound of Formula XVIII.

The oxidative cleavage of a compound of Formula LI to form a compound of Formula LII can be done similarly to the cleavage of a compound of Formula XVIII to form a compound of Formula XIX. The compound of Formula LII can be deformylated to a compound of Formula LIII under similar conditions as that of deformylation of a compound of Formula XIX to form a compound of Formula XX.

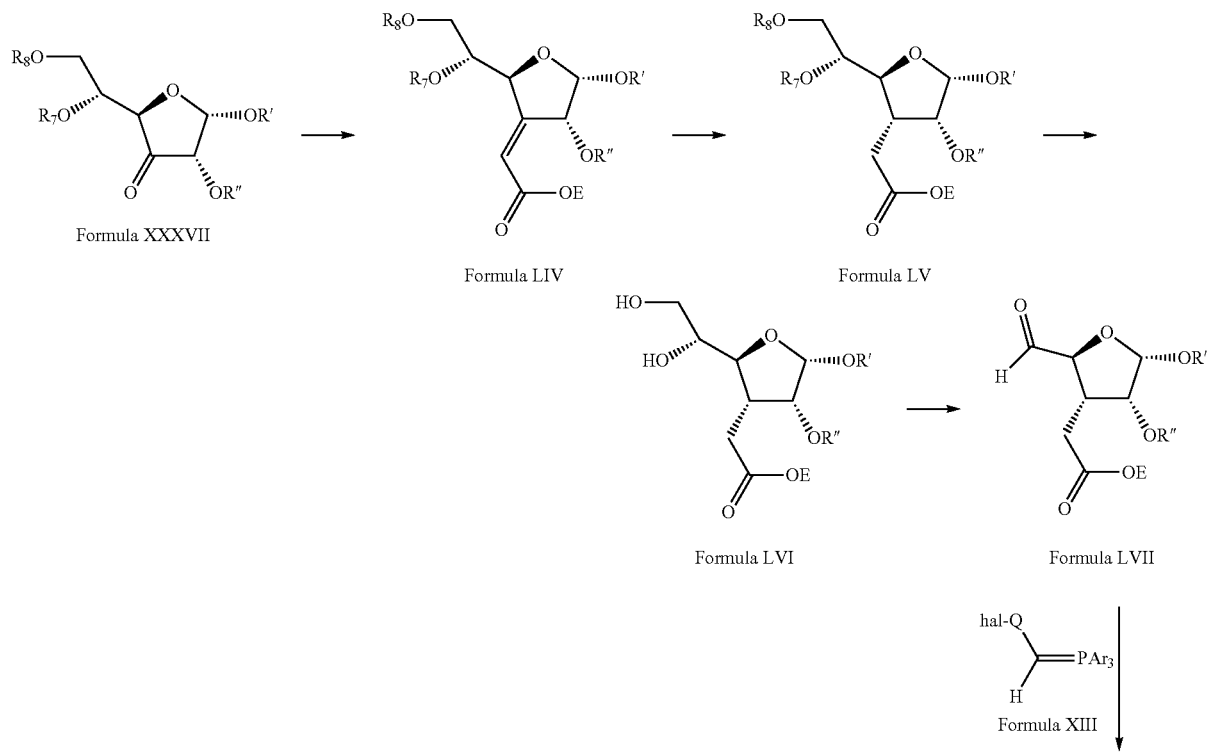

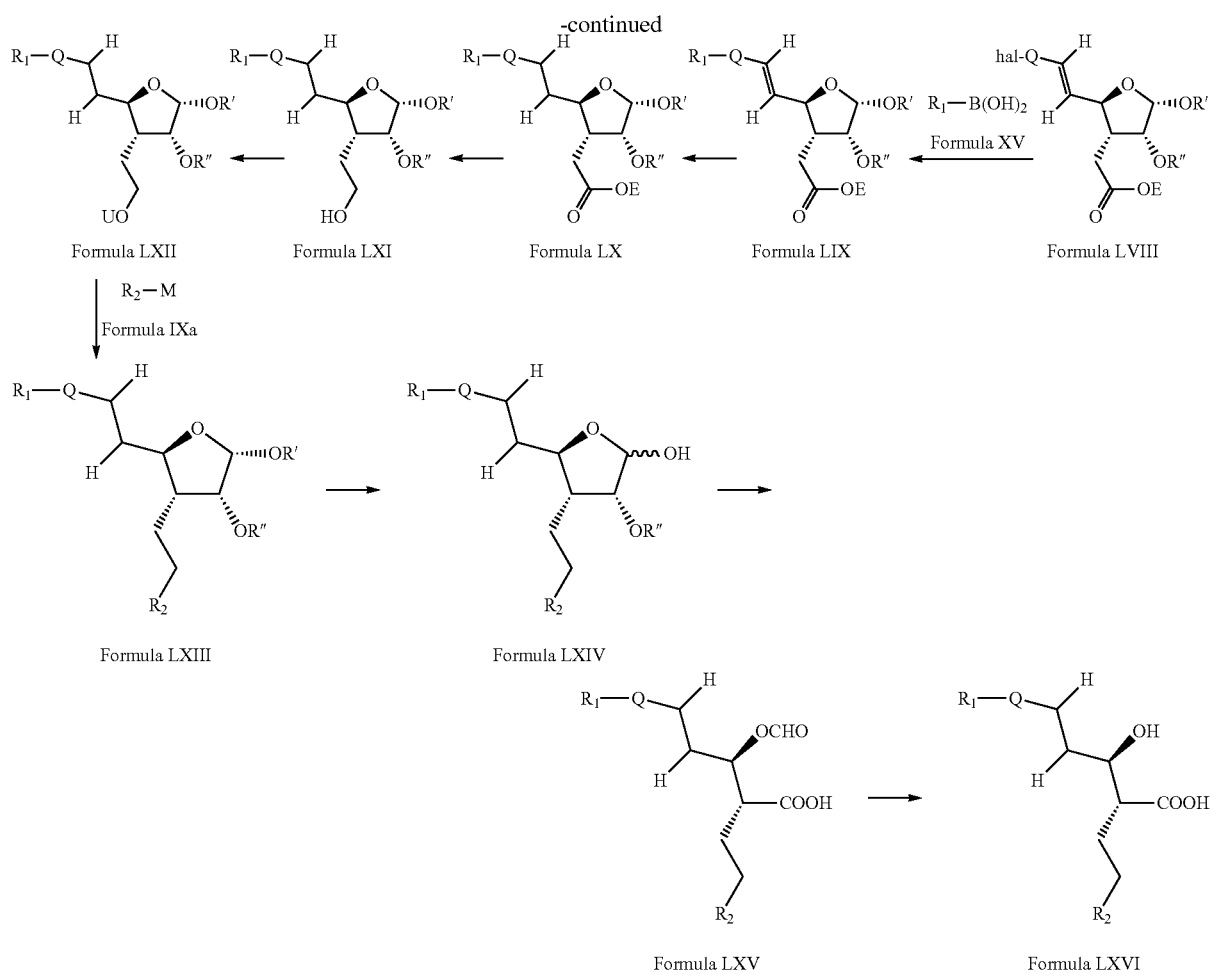

Compounds of Formula LXVI can be prepared, for example, by following synthetic routes as depicted in Scheme VI. Thus, a compound of Formula XXXVII (wherein $R_7$, $R_8$, R', and R" are same as described earlier) can be converted to form a compound of Formula LIV which can then be hydrogenated to form a compound of Formula LV. The compound of Formula LV can be selectively deprotected to form a compound of Formula LVI which on oxidation, can form a compound of Formula LVII. The compound of Formula LVII can be reacted with a compound of Formula XIII to form a compound of Formula LVIII which can then be coupled with a compound of Formula XV (wherein $R_1$ is same as defined earlier) to give a compound of Formula LIX. The compound of Formula LIX can be hydrogenated to form a compound of Formula LX which can then be reduced to form a compound of Formula LXI. The compound of Formula LXI can be activated to form a compound of Formula LXII (wherein U is an O-activating group, for example, mesyl, tosyl, or triflate), which can then be reacted with a compound of Formula IXa (wherein $R_2$ is an N-containing heterocyclyl or heteroaryl and M is a metal, for example, potassium, lithium, or sodium) to form a compound of Formula LXIII. The compound of Formula LXIII can then be deprotected to form a compound of Formula LXIV which can be oxidatively cleaved to form a compound of Formula LXV. The compound of Formula LXV can be deformylated to form a compound of Formula LXVI.

The compound of Formula XXXVII can be converted to form a compound of Formula LIV under similar conditions as that of conversion of a compound of Formula V to form a compound of Formula VI. Hydrogenation of a compound of Formula LIV to form a compound of Formula LV can be carried out similarly to the hydrogenation of a compound of Formula VI to form compounds of Formulae VIIa and VIIb.

The compound of Formula LV can be selectively deprotected to form a compound of Formula LVI under similar conditions as that of the deprotection of a compound of Formula XLV to give a compound of Formula XLVI. The compound of Formula LVI can be oxidized to form a compound of Formula LVII similarly to the oxidation of a compound of Formula XLVI to form a compound of Formula XLVII.

The reaction of a compound of Formula LVII with a compound of Formula XIII to form a compound of Formula LVIII can be carried out under similar conditions to the reaction of a compound of Formula XII to form a compound of Formula XIV. The compound of Formula LVIII can be coupled with a compound of Formula XV to give a compound of Formula LIX under similar conditions as that of the coupling of a compound of Formula XIV to form a compound of Formula XVI. Hydrogenation of a compound of Formula LIX to form a compound of Formula LX can be carried out under similar conditions as that of hydrogenation of a compound of Formula VI to form compounds of Formulae VIIa and VIIb.

The compound of Formula LX can be reduced to form a compound of Formula LXI under similar conditions as that of reduction of compounds of Formulae VIIa and VIIb to form compounds of Formulae VIIIa and VIIIb.

A compound of Formula LXI can be activated to form a compound of Formula LXII in a solvent, for example, dichloromethane, toluene, or dichloroethane, using a base, for example, triethylamine, diisopropylamine, or N-methylmorpholine, using a suitable sulphonyl chloride, for example, methanesulphonyl chloride or p-toluene sulphonyl chloride. The reaction of a compound of Formula LXII with a compound of Formula IXa to yield a compound of Formula LXIII can be carried out in an organic solvent, for example, tetrahydrofuran, dimethyl sulphoxide, dimethylformamide, acetonitrile, dioxane, or dimethylacetamide. Alternatively, the reaction of a compound of Formula LXII with a compound of Formula IX to yield a compound of Formula LXIII can be carried out in the presence of a base, for example, sodium hydride, potassium tert-butoxide, sodium (m) ethoxide in an organic solvent, for example, tetrahydrofuran, dimethyl sulphoxide, dimethylformamide, acetonitrile, dioxane, or dimethylacetamide. Alternatively, a compound of Formula LXI can be converted to a compound of Formula LXIII following similar protocols as that of the reaction of a compound of Formula VIIIa with a compound of Formula IX to give a compound of Formula X.

The compound of Formula LXIII can be deprotected to form a compound of Formula LXIV similarly to the deprotection of a compound of Formula XVII to form a compound of Formula XVIII.

The oxidative cleavage of a compound of Formula LXIV to give a compound of Formula LXV can be done similarly to the cleavage of a compound of Formula XVIII to form a compound of Formula XIX. The compound of Formula LXV can be deformylated to form a compound of Formula LXVI under similar condition as that of deformylation of a compound of Formula XIX to form a compound of Formula XX.

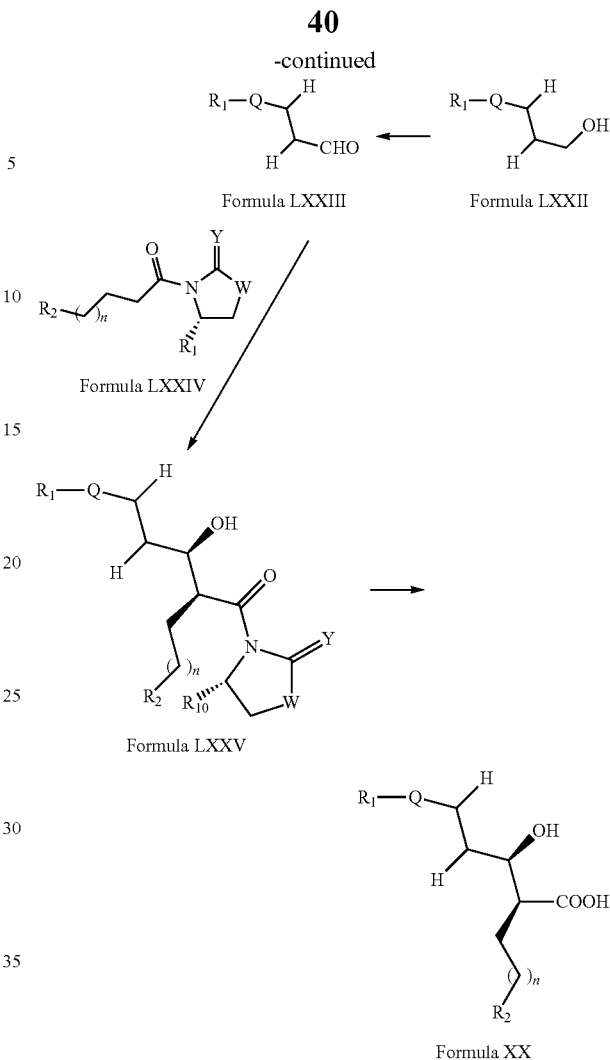

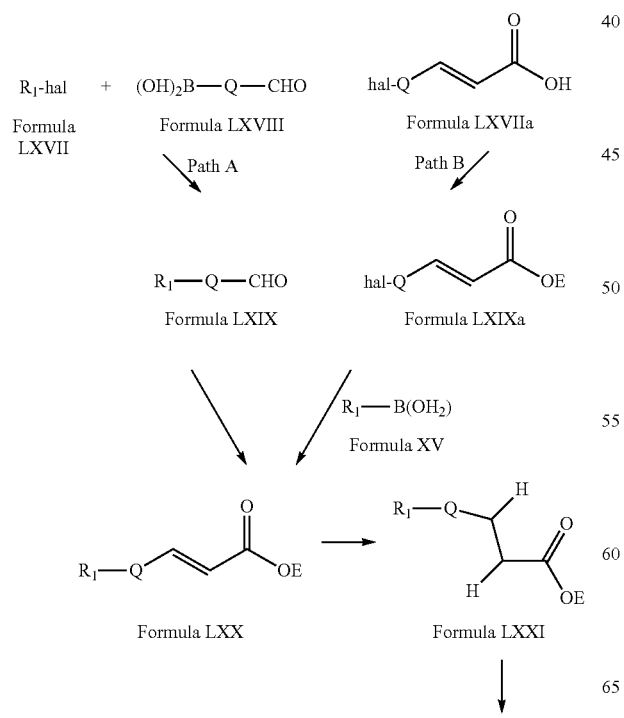

Scheme VII

Compounds of Formula XX can also be prepared, for example, by following alternate synthetic routes as depicted in Scheme VII. Thus, a compound of Formula LXVII can be coupled with a compound of Formula LXVIII to form a compound of Formula LXIX (wherein $R_1$ and Q are same as defined earlier), which can then be converted to a compound of Formula LXX (Path A) (wherein E is same as defined earlier). Alternately, the compound of Formula LXVIIa can undergo esterification to give a compound of Formula LXIXa, which can be coupled with the compound of Formula XV to form the compound of Formula LXX (Path B) (wherein E is same as defined earlier). The compound of Formula LXX can be hydrogenated to form the compound of Formula LXXI, which can then be reduced to form a compound of Formula LXXII. The compound of Formula LXXII can be oxidized to form a compound of Formula LXXIII, which can then react with a compound of Formula LXXIV (wherein, when $R_2$ is N-containing heterocyclyl or heteroaryl, Y and W can be oxygen or sulphur, $R_{10}$ can be alkyl, aryl, or aralkyl, and n is as defined earlier) to form a compound of Formula LXXV. The compound of Formula LXXII can be further hydrolysed to form a compound of Formula XX.

Coupling of a compound of Formula LXVII with a compound of Formula LXVIII to form a compound of Formula LXIX can be carried out similarly to the coupling of a compound of Formula XIV to form a compound of Formula XVI.

Conversion of a compound of Formula LXIX to form a compound of Formula LXX can be carried out under similar conditions to the conversion of a compound of Formula V to form a compound of Formula VI. Esterification of compound of Formula LXVIIIa to gives a compound of Formula LXIXa can be carried out in a solvent, for example, methanol, ethanol, tert-butanol, or benzyl alcohol with a halogenating agent, for example, thionyl chloride or oxalyl chloride. Coupling of a compound of Formula LXIXa with a compound of Formula XV to form a compound of Formula LXX can be carried out similarly to the coupling of a compound of Formula XIV to form a compound of Formula XVI.

The compound of Formula LXX can be hydrogenated to form a compound of Formula LXXI similarly to the hydrogenation of a compound of Formula VI to form compounds of Formulae VIIa and VIIb. The reduction of a compound of Formula LXXI to form a compound of Formula LXXII can be carried out under similar conditions as that of reduction of compounds of Formulae VIIa and VIIb to form compounds of Formulae VIIIa and VIIIb. The compound of Formula LXXII can be oxidized to form a compound of Formula LXXIII similarly to the oxidation of a compound of Formula IV to form a compound of Formula V.

The asymmetric aldol addition of a compound of Formula LXXIII with a compound of Formula LXXIV to form a compound of Formula LXXIV can be carried out by generating the enolates with titanium chloride, dibutyl boron triflate, dialkyl boron chloride, or tin(II) triflate, in the presence of a base, for example, diisopropylethylamine, tetramethylethelenediamine, tributylamine, N-ethylpiperidine, 1,4-diazabicyclo[2.2.2]octane, 1,8-Diazabicyclo[5.4.0]undec-7-ene, tetramethylpropylenediamine, or (−) sparteine, in a solvent, for example, dichloromethane or diethyl ether.

Hydrolysis of a compound of Formula LXXIV to form a compound of Formula XX can be carried out with hydrogen peroxide and lithium hydroxide, in the presence of a solvent, for example, tetrahydrofuran, water, or mixtures thereof.

Compound Nos. 1 to 81; 86-88; 90-95; 97-119; 121-142; 144-203; 211-213; and 226-232 were prepared following Schemes I and II. Compound Nos. 82 to 85 and 204 were prepared following Schemes I, II, and III. Compound Nos. 143 and 208 were prepared following Scheme IV. Compound Nos. 120 and 205-207 were prepared following Scheme V. Compound Nos. 89 and 96 were prepared following Scheme VI. Compound Nos. 86; 209-210; and 214-225 were prepared following Scheme VII.

In the above schemes, where specific bases, acids, solvents, condensing agents, reducing agents, deprotecting agents, hydrolyzing agents, metal catalysts, etc., are mentioned, it is to be understood that other acids, bases, solvents, condensing agents, reducing agents, deprotecting agents, hydrolyzing agents, metal catalysts, etc., known to those skilled in the art may also be used. Similarly, the reaction temperature and duration of the reactions may be adjusted according to the requirements that arise during the process.

The following examples are set forth to demonstrate general synthetic procedures for the preparation of representative compounds of the present invention. The examples are provided to illustrate a particular aspect of the disclosure and do not limit the scope of the present invention.

EXAMPLES

Synthesis of Starting Materials

Synthesis of 6-methyl-1,2,3-benzotriazin-4(3H)-one

The title compound was prepared following the procedure outlined in *J. Med. Chem.*, 35(14), 2626-2630 (1992).

The following analogues of 6-methyl-1,2,3-benzotriazin-4(3H)-one were prepared analogously:
8-methyl-1,2,3-benzotriazin-4(3H)-one;
7-methyl-1,2,3-benzotriazin-4(3H)-one;
6-methyl-1,2,3-benzotriazin-4(3H)-one;
8-methoxy-1,2,3-benzotriazin-4(3H)-one;
6-methoxy-1,2,3-benzotriazin-4(3H)-one;
8-chloro-1,2,3-benzotriazin-4(3H)-one;
7-chloro-1,2,3-benzotriazin-4(3H)-one;
6-chloro-1,2,3-benzotriazin-4(3H)-one;
5-chloro-1,2,3-benzotriazin-4(3H)-one;
6,7-difluoro-1,2,3-benzotriazin-4(3H)-one;
8-fluoro-1,2,3-benzotriazin-4(3H)-one;
5-fluoro-1,2,3-benzotriazin-4(3H)-one;
6-fluoro-1,2,3-benzotriazin-4(3H)-one;
5-(6-methoxypyridin-3-yl)-1,2,3-benzotriazin-4(3H)-one;
7-(6-methoxypyridin-3-yl)-1,2,3-benzotriazin-4(3H)-one; and
7-(trifluoromethyl)-1,2,3-benzotriazin-4(3H)-one.

Synthesis of 5-tert-butyl-1H-isoindole-1,3(2H)-dione

The title compound was prepared following the procedure outlined in *Can. J. Chem.*, Vol. 63, 121-128 (1985).
Mass (m/z): 204.12 (M$^+$+1)
The following analogues of 5-tert-butyl-1H-isoindole-1,3(2H)-dione were prepared analogously:
4-fluoro-1H-isoindole-1,3(2H)-dione; and
5-chloro-1H-isoindole-1,3(2H)-dione.

Synthesis of (4-bromobenzyl)(triphenyl)phosphonium bromide

A mixture of 1-bromo-4-(bromomethyl)benzene (5 g) and triphenylphosphine (5.24 g) in xylene (20 mL) were heated to reflux for 18 hours. The reaction mixture was cooled, filtered, washed with hexane, and dried under vacuum to afford the title compound (8 g).
Mass (m/z): 433.9 (M$^+$+1)
The following Wittig salts were prepared analogously:
[(4-bromo-2-thienyl)methyl]triphenyl phosphonium bromide;
[(6-bromopyridin-3-yl)methyl](triphenyl)phosphonium bromide;
(4-bromo-2-fluorobenzyl)(triphenyl)phosphonium bromide;
4-tert-butylbenzyl(triphenyl)phosphonium bromide;
triphenyl[4-(trifluoromethyl)benzyl]phosphonium bromide;
benzyl(triphenyl)phosphonium bromide;
(4-bromo-3-fluorobenzyl)(triphenyl)phosphonium bromide;
(4-bromo-2-fluorobenzyl)(triphenyl)phosphonium bromide; and
(4-chloro-3-fluorobenzyl)(triphenyl)phosphonium bromide.

Synthesis of 4-(4-oxo-1,2,3-benzotriazin-3(4H)-yl)butanoic acid

Step a: Synthesis of ethyl 4-(4-oxo-1,2,3-benzotriazin-3(4H)-yl)butanoate

In a dry round bottom flask, 1,2,3-benzotriazin-4(3H)-one (50 g), ethyl 4-bromobutanoate (86.2 g) and potassium carbonate (141 g) were taken and dissolved in dimethylformamide (350 mL) and heated to 60° C. to 70° C. for 3 to 4 hours. After cooling to room temperature, water was added to the reaction mixture and extracted with ethyl acetate. The combined organic layer was washed with water and brine and dried over anhydrous sodium sulfate. Solvents were evaporated under reduced pressure and the crude product was purified by silica gel flash column chromatography over silica gel using 20% ethylacetate in hexane as eluant to afford the title compound (68 g).

Step b: Synthesis of 4-(4-oxo-1,2,3-benzotriazin-3(4H)-yl)butanoic acid

To a stirred solution of compound obtained from step a above (40 g), in a solvent mixture of tetrahydrofuran/methanol/water (3:1:1, 400 mL), lithium hydroxide monohydrate (6.43 g) was added at 0° C. under a nitrogen atmosphere. The reaction mixture was stirred at 0° C. until completion of hydrolysis. The solvents were evaporated, diluted with water, and extracted with ethyl acetate. The aqueous layers were acidified with saturated aqueous sodium hydrogen sulfate solution and extracted with ethyl acetate. The combined layers were washed with water and brine and dried over anhydrous sodium sulfate. The solvents were evaporated under reduced pressure to afford the title compound (28 g).

The following analogue of 4-(4-oxo-1,2,3-benzotriazin-3(4H)-yl)butanoic acid was prepared analogously:
3-(4-oxo-1,2,3-benzotriazin-3(4H)-yl)propanoic acid.

Synthesis of 3-{4-[(4S)-4-benzyl-2-oxo-1,3-thiazolidin-3-yl]-4-oxobutyl}-1,2,3-benzotriazin-4(3H)-one

Step a: Synthesis of (2S)-2-amino-3-phenylpropan-1-ol (Ref: *J. Org. Chem.*, 58, 3568-3571 (1993)).

To a suspension of sodium borohydride (16.5 g) in dry tetrahydrofuran (600 mL), (L)-phenylalanine (30 g) was added at one portion. The flask was cooled to 0° C. under nitrogen atmosphere. Iodine (46.18 g) solution in tetrahydrofuran (150 mL) was added slowly in drop-wise manner over 40 minutes, resulting in vigorous evolution of $H_2$. After the complete addition of iodine, the reaction mixture was heated to reflux for 18 hours and cooled to room temperature. The reaction mixture was quenched with methanol until the reaction mixture became clear. Further, the solution was stirred for 30 minutes at room temperature. The solvents were removed by rotary evaporation to obtain a white paste which was dissolved by 20% aqueous potassium hydroxide (450 mL). The solution was stirred for 4 hours and then dichloromethane was added. The organic layers were separated and the aqueous layer was extracted with dichloromethane. The combined organic layers were washed with brine and dried over anhydrous sodium sulfate. The solvents were evaporated under reduced pressure to afford 32.5 g of (L)-phenylaninol as a viscous liquid. The crude product was used as such for the next step.

Step b: Synthesis of (4S)-4-benzyl-1,3-thiazolidine-2-thione (Ref: *J. Org. Chem.*, 60(20), 6604-6607 (1995)).

To a solution of the compound obtained in step a above (32.5 g) in 1N aqueous potassium hydroxide (1 L), carbon disulphide (68 mL, 5.0 equivalence) was added and the reaction mixture was refluxed for 16 hours. After cooling to room temperature, the aqueous solution was extracted with dichloromethane. The organic layer was washed with brine, dried over anhydrous sodium sulfate, and concentrated under reduced pressure. The crude product was purified by silica gel flash column chromatography using 15% ethyl acetate in hexane to get the title compound (22.5 g).

Step c: Synthesis of (4S)-4-benzyl-1,3-thiazolidin-2-one

To a solution of (4S)-4-benzyl-1,3-thiazolidine-2-thione (38 g) in dichloromethane (350 mL) cooled to 0° C., propylene oxide (12.7 mL) and trifluoroacetic acid (14 mL) were added. After stirring the reaction mixture for 2 hours, the solvents were evaporated under reduced pressure to obtain a residue which was purified by column chromatography over silica gel using 20% ethyl acetate in hexane as eluent to afford the title compound (0.9 g).

Mass (m/z): 194.18

Step d: Synthesis of 3-{4-[(4S)-4-benzyl-2-oxo-1,3-thiazolidin-3-yl]-4-oxobutyl}-1,2,3-benzotriazin-4(3H)-one To a solution of the compound obtained from step c above (2.1 g) in dichloromethane (25 mL) cooled to 0° C., 4-dimethylaminopridine (0.334 g) and triethylamine (5.7 mL) were added. After stirring the reaction mixture for 10 minutes, 1-(3-dimethylaminopropyl)-3-ethylcarbodimide hydrochloride (3.9 g) and 4-(4-oxo-1,2,3-benzotriazin-3(4H)-yl)butanoic acid (3 g) were added, and the reaction mixture was stirred at room temperature for 14 hours. Dichloromethane and water were added to the reaction mixture. The organic layer was separated, washed with water and brine solution, and dried over anhydrous sodium sulphate. The solvent was evaporated under reduced pressure to obtain a residue which was purified by column chromatography over silica gel using 25% ethyl acetate in hexane as eluant to afford the title compound (4.4 g). Mass (m/z): 409.16

The following analogue of 3-{4-[(4S)-4-benzyl-2-oxo-1,3-thiazolidin-3-yl]-4-oxobutyl}-1,2,3-benzotriazin-4(3H)-one was prepared analogously:
3-{3-[(4S)-4-benzyl-2-oxo-1,3-thiazolidin-3-yl]-3-oxopropyl}-1,2,3-benzotriazin-4(3H)-one

Example 1

Synthesis of (2S,3R)-3-hydroxy-2-[2-(4-oxo-1,2,3-benzotriazin-3(4H)-yl)ethyl]-5-(4-pyrimidin-5-ylphenyl)pentanoic acid (Compound No. 1)

Step a: Synthesis of 5-O-[tert-butyl(diphenyl)silyl]-D-arabinofuranose

D-Arabinose (200 g) and imidazole (199 g) were placed in a three-neck round bottom flask and connected to high vacuum for 30 minutes. The vacuum was released under nitrogen atmosphere and dimethylformamide (1.8 L) was added to the above mixture at room temperature followed by drop-wise addition of t-butyldiphenylchlorosilane (443 mL) for 10 minutes under a nitrogen atmosphere. The resulting mixture was stirred for 16 hours at the same temperature. Dimethylformamide was evaporated under reduced pressure. The residue was taken up in ethyl acetate and washed with water. The organic layer was dried over anhydrous sodium sulphate. The solvent was evaporated under reduced pressure to obtain a crude residue which was purified by column chromatography over silica gel using 80% ethyl acetate in hexane as eluant to afford the title compound (273 g).

Mass (m/z): 389.37 (M$^+$+1)

Step b: Synthesis of 5-O-[tert-butyl(diphenyl)silyl]-1,2-O-isopropylidene-β-D-arabinofuranose To the solution of the compound obtained from step a above (273 g) in acetone (2.5 L), DL-camphorsulphonic acid (16 g) and anhydrous copper sulphate (346 g) were charged under a nitrogen atmosphere at room temperature. The reaction mixture was stirred for 16 hours at the same temperature. A saturated solution of sodium bicarbonate (2 L) was added drop-wise until a basic pH was attained, and the reaction mixture was further stirred for 2 hours at the same temperature. The resulting mixture was filtered using a Buchner funnel, and the residue was washed with acetone. The filtrate was concentrated, dissolved in ethyl acetate, and washed with water. The organic layer was dried over anhydrous sodium sulphate, filtered, and evaporated under reduced pressure to furnish the title compound (295 g).

Mass (m/z): 429.41 (M$^+$+1)

Step c: Synthesis of 5-O-[tert-butyl(diphenyl)silyl]-1,2-O-isopropylidene-β-D-threo-pentofuranos-3-ulose Oxalyl chloride (145 ml) and dichloromethane (1 L) were taken in a three neck round bottom flask and cooled to −75° C. under a nitrogen atmosphere. Dimethylsulfoxide (212 mL) was added drop-wise to the above solution maintaining the reaction temperature at −70° C. The reaction mixture was stirred for 30 minutes at the same temperature, then a solution of the compound obtained from step b above (285 g) in dichloromethane (1 L), was added slowly to the above mixture, maintaining the reaction temperature −70° C. After 20 minutes of the above addition, triethylamine (560 mL) was added drop-wise at the same temperature. Saturated solution of ammonium chloride in water (1.5 L) was then added after 30 minutes and the reaction temperature was allowed to rise to room temperature. The reaction mixture was extracted with dichloromethane. Organic extracts were dried over anhydrous sodium sulphate, filtered, and evaporated under reduced pressure to afford the title compound (285 g).

Step d: Synthesis of 5-O-[tert-butyl(diphenyl)silyl]-3-deoxy-3-(2-ethoxy-2-oxoethylidene)-1,2-O-isopropylidene-β-D-arabinofuranose To a suspension of sodium hydride (29.4 g, 60% in oil) in tetrahydrofuran (1 L) at 0° C., triethyl phosphonoacetate (200 mL) was charged. After 20 minutes, a solution of the compound obtained from step c above (285 g) in tetrahydrofuran (2 L) was added drop-wise and the reaction mixture was stirred for 1 hour at the same temperature. A saturated solution of ammonium chloride in water (1.5 L) was added to the reaction mixture. The resulting mixture was extracted with ethyl acetate. Combined extracts were dried over anhydrous sodium sulphate and evaporated under reduced pressure to yield a residue which was purified by column chromatography over silica gel using 15% ethyl acetate in hexane as eluent to afford the title compound (275 g).

Mass (m/z): 497.43 (M$^+$+1)

Step e: Synthesis of 5-O-[tert-butyl(diphenyl)silyl]-3-deoxy-3-(2-ethoxy-2-oxoethyl)-1,2-O-isopropylidene-β-D-lyxofuranose and 5-O-[tert-butyl(diphenyl)silyl]-3-deoxy-3-(2-ethoxy-2-oxoethyl)-1,2-O-isopropylidene-α-L-ribofuranose 10% Palladium on charcoal (100 g) was added to the solution of the compound obtained from step d above (275 g) in tetrahydrofuran (2 L) and methanol (1 L) at room temperature and hydrogen was supplied at 50 psi (Paar apparatus) for 2 hours. The reaction mixture was filtered through a celite pad and the residue was washed with ethyl acetate. The filtrate was concentrated to afford a mixture of 5-O-[tert-butyl (diphenyl)silyl]-3-deoxy-3-(2-ethoxy-2-oxoethyl)-1,2-O-isopropylidene-β-D-lyxofuranose and 5-O-[tert-butyl(diphenyl)silyl]-3-deoxy-3-(2-ethoxy-2-oxoethyl)-1,2-O-isopropylidene-α-L-ribofuranose (275 g).

Mass (m/z): 499.42 (M$^+$+1)

Step f: Synthesis of 5-O-[tert-butyl(diphenyl)silyl]-3-deoxy-3-(2-hydroxyethyl)-1,2-O-isopropylidene-β-D-lyxofuranose and 5-O-[tert-butyl(diphenyl)silyl]-3-deoxy-3-(2-hydroxyethyl)-1,2-O-isopropylidene-α-L-ribofuranose To a suspension of lithium aluminum hydride (48 g) in tetrahydrofuran (1 L), a solution of the compound obtained from step e above (275 g) in tetrahydrofuran (1.5 L) was added at −50° C. The resulting mixture was allowed to attain 0° C. The reaction mixture was stirred for 30 minutes at the same temperature and again cooled to −50° C. Ethyl acetate (2 L) was added slowly while maintaining −50° C. An aqueous solution of ammonium chloride (100 g) in water (2.5 L) was added at the same temperature. The reaction mixture was slowly allowed to warm to room temperature, and the reaction mixture was stirred for 12 hours at the same temperature. The reaction mixture was then filtered through a celite pad and the residue was washed with ethyl acetate. The organic layer was dried over anhydrous sodium sulphate, filtered, concentrated under reduced pressure, and the residue thus obtained was purified by column chromatography over silica gel using 50% ethyl acetate in hexane as eluant to afford the 5-O-[tert-butyl (diphenyl)silyl]-3-deoxy-3-(2-hydroxyethyl)-1,2-O-isopropylidene-β-D-lyxofuranose (130 g) and 5-O-[tert-butyl (diphenyl)silyl]-3-deoxy-3-(2-hydroxyethyl)-1,2-O-isopropylidene-α-L-ribofuranose (40.0 g).

Mass (m/z): 457.39 (M$^+$+1)

Step g: Synthesis of 5-O-[tert-butyl(diphenyl)silyl]-3-deoxy-1,2-O-isopropylidene-3-[2-(4-oxo-1,2,3-benzotriazin-3(4H)-yl)ethyl]-β-D-lyxofuranose 5-O-[tert-butyl(diphenyl)silyl]-3-deoxy-3-(2-hydroxyethyl)-1,2-O-isopropylidene-β-D-lyxofuranose (35 g), triphenylphosphine (30.8 g) and 1,2,3-benzotriazin-4(3H)-one (12.6 g) were dried in high vacuum in a round bottom flask for 10 minutes. Then the vacuum was released under a nitrogen atmosphere and tetrahydrofuran (70 mL) was added to the above reaction mixture. The reaction mixture was cooled to 0° C. and diisopropyl azodicarboxylate (17 mL) was added slowly. The reaction mixture was stirred for 30 minutes at the same temperature, and then quenched with water and extracted with ethyl acetate. The organic layer was washed with water and brine solution, dried over anhydrous sodium sulphate, and concentrated to obtain a residue which was purified by column chromatography over silica gel using 30% ethyl acetate in hexane as eluant to afford the title compound (50 g).

Mass (m/z): 586.05 (M$^+$+1)

Step h: Synthesis of 3-deoxy-1,2-O-isopropylidene-3-[2-(4-oxo-1,2,3-benzotriazin-3(4H)-yl)ethyl]-β-D-lyxofuranose To a solution of the compound obtained from step g above (50 g) in dry tetrahydrofuran (400 mL) at 0° C., tetra-butyl ammonium fluoride (170 mL) was added. The resulting mixture was initially stirred at 0° C. for 1 hour, and then at room temperature for 4 hours. The reaction mixture was cooled to 0° C., quenched with saturated ammonium chloride, and extracted with ethyl acetate. The organic layer was washed with water and brine, dried over anhydrous sodium sulphate and concentrated. The residue thus obtained was purified by column chromatography over silica gel using 80% ethyl acetate in hexane as eluant to furnish the title compound (22 g).

Mass (m/z): 369.98 (M$^+$+23)

Step i: Synthesis of (5S)-3-deoxy-4,5-O-isopropylidene-3-[2-(4-oxo-1,2,3-benzotriazin-3(4H)-yl)ethyl]-D-arabino-pentodialdo-5,2-furanose Oxalyl chloride (13.7 mL) and dichloromethane (300 mL) were taken in a three neck round bottom flask and cooled to −78° C. Dimethylsulfoxide (20.2 mL) was added drop-wise to the reaction mixture. The reaction mixture was warmed to −35° C. for 5 to 10 minutes and again cooled to −78° C. A solution of the compound obtained from step h above (22 g) in dichloromethane (200 mL) was added slowly while maintaining the same temperature. The reaction mixture was stirred for 45 minutes until the reaction temperature reached −35° C. The reaction mixture was again cooled to −78° C. and triethylamine (53 mL) was added. The reaction mixture was stirred for an additional 30 minutes, and the temperature was allowed to reach −35° C. The reaction mixture was quenched with a saturated solution of ammonium chloride and extracted with dichloromethane. The combined organic layers were washed with water and brine solution, dried over anhydrous sodium sulphate, and concentrated to furnish the title compound (22 g).

Step j: Synthesis of 3-(2-{(3aS,5R,6S,6aS)-5-[(E)-2-(4-bromophenyl)vinyl]-2,2-dimethyltetrahydrofuro[2,3-d][1,3]dioxol-6-yl}ethyl)-1,2,3-benzotriazin-4(3H)-one To the suspension of sodium hydride (3.3 g, 60% in oil) in tetrahydrofuran (50 mL) cooled to 0° C., (4-bromobenzyl)triphenylphosphonium bromide (48.8 g) in tetrahydrofuran (100 mL) was added. A solution of the compound obtained from step i above (22 g) in tetrahydrofuran (100 mL) was added drop-wise after 20 minutes, and the reaction mixture was stirred for 1 hour at the same temperature. The reaction mixture was quenched with water and extracted with ethyl acetate. The organic layer was washed with water and brine solution and dried over anhydrous sodium sulphate. The solvent was evaporated under reduced pressure and the residue thus obtained was purified by column chromatography using 30% ethyl acetate in hexane as eluant to furnish the title compound (24.5 g).

Mass (m/z): 498.84 (M$^+$+1)

Step k: Synthesis of 3-(2-{(3aS,5R,6S,6aS)-2,2-dimethyl-5-[(E)-2-(4-pyrimidin-5-ylphenyl)vinyl]tetrahydrofuro[2,3-d][1,3]dioxol-6-yl}ethyl)-1,2,3-benzotriazin-4(3H)-one A mixture of the compound obtained from step j above (0.35 g), pyrimidin-5-ylboronic acid (0.174 g), tetrakistriphenylphosphinepalladium (0) (0.081 g), and potassium carbonate (0.291 g) was dried under high vacuum for 10 minutes and dry dimethylformamide (5 mL) was added at room temperature. The reaction mixture was heated at 120° C. for 2 hours, and then quenched with water and extracted with ethyl acetate. The organic layer was washed with water and brine solution and dried over anhydrous sodium sulphate. The solvent was evaporated under the reduced pressure to obtain a residue which was purified by column chromatography over silica gel using 40% ethyl acetate in hexane as eluant to afford the title compound (0.3 g).

Mass (m/z): 498.0 (M$^+$+1)

Step l: Synthesis of 3-(2-{(3aS,5R,6S,6aS)-2,2-dimethyl-5-[2-(4-pyrimidin-5-ylphenyl)ethyl]tetrahydrofuro[2,3-d][1,3]dioxol-6-yl}ethyl)-1,2,3-benzotriazin-4(3H)-one To the solution of the compound obtained from step k above (0.3 g) in a solvent mixture of tetrahydrofuran: methanol (10 mL, 1:1), 10% palladium on charcoal (0.15 g) was added at room temperature and the reaction mixture was hydrogenated with hydrogen at 35 psi for 4 hours in a Paar apparatus. The reaction mixture was filtered through a celite pad and the residue was washed with methanol. The filtrate was concentrated to afford the title compound (0.3 g).

Step m: Synthesis of 3-(2-{(2R,3R,4S,5R)-4,5-dihydroxy-2-[2-(4-pyrimidin-5-ylphenyl)ethyl]tetrahydrofuran-3-yl}ethyl)-1,2,3-benzotriazin-4(3H)-one Perchloric acid (0.2 mL) was added to a solution of the compound obtained from step l above (0.3 g) in acetonitrile (4 mL) and water (0.2 mL) at room temperature. The reaction mixture was heated to 55° C. for 30 minutes. The reaction mixture was then quenched using sodium bicarbonate solution. The solvents were evaporated under reduced pressure. The residue thus obtained was taken up in ethyl acetate and water. The organic layer was separated and washed with water and brine solution and dried over anhydrous sodium sulphate. The solvent was concentrated under reduced pressure to yield the title compound (0.25 g).

Step n: Synthesis of (2S,3R)-3-(formyloxy)-2-[2-(4-oxo-1,2,3-benzotriazin-3(4H)-yl)ethyl]-5-(4-pyrimidin-5-ylphenyl)pentanoic acid To a solution of the compound obtained from step m above (0.25 g) in tert-butanol: tetrahydrofuran (5 mL:5 mL) at 0° C., a solution of sodium metaperiodate (0.465 g in 5 mL of water) was added. The reaction mixture was stirred for 2 hours at the same temperature and potassium permanganate (0.017 g) was added at 0° C. After stirring the reaction mixture for an additional 6 hours at room temperature, the reaction mixture was evaporated on a rotary evaporator. The residue was taken into water and extracted with ethyl acetate. The organic layer was washed with water and brine solution and dried over anhydrous sodium sulphate. The solvent was evaporated under the reduced pressure to afford the title compound (0.25 g).

Step o: Synthesis of (2S,3R)-3-hydroxy-2-[2-(4-oxo-1,2,3-benzotriazin-3(4H)-yl)ethyl]-5-(4-pyrimidin-5-ylphenyl)pentanoic acid Potassium carbonate (0.081 g) was added to a solution of the compound obtained from step n above (0.25 g) in methanol (5 mL) and tetrahydrofuran (5 mL) at 0° C. The reaction mixture was stirred at room temperature for 3 hours. Solvents were evaporated and the residue was taken into water and ethyl acetate. The organic layer was washed with water and brine solution and dried over anhydrous sodium sulphate. The solvent was evaporated under reduced pressure to obtain a residue which was purified by column chromatography over silica gel using 60% ethyl acetate in hexane as eluant to afford the title compound (0.030 g).

Mass (m/z): 446.0 (M$^+$+1).
$^1$HNMR (CD$_3$OD): δ 9.09 (s, 1H), 9.03 (s, 1H), 8.30 (d, 1H, J=8 Hz), 8.14 (d, 1H, J=8 Hz), 8.05-8.03 (m, 1H), 7.89-7.87 (m, 1H), 7.61 (d, 2H, J=8 Hz), 7.53-7.59 (m, 1H), 7.35 (d, 2H, J=8 Hz), 4.57-4.52 (m, 2H), 3.79-3.77 (m, 1H), 2.89-2.87 (m, 1H), 2.69-2.67 (m, 1H), 2.47-2.46 (m, 1H), 2.29-2.25 (m, 2H), 1.82-1.77 (m, 2H).

Example 1A

Synthesis of (2S,3R)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 86)

Step a: Synthesis of 3-(2-{(3aS,5R,6S,6aS)-5-[(E)-2-(4-bromophenyl)ethenyl]-2,2-dimethyltetrahydrofuro[2,3-d][1,3]dioxol-6-yl}ethyl)-1,2,3-benzotriazin-4(3H)-one To the suspension of potassium t-butoxide (3.3 g, 60% in oil) in dimethyl sulfoxide (50 mL) cooled to 0° C., 4-bromobenzyl triphenyl-phosphonium bromide (48.8 g) in dimethyl sulfoxide (100 mL) was added. After 20 minutes, the compound obtained from step i of Example 1 above (22 g) was added in dimethyl sulfoxide (100 mL) drop-wise, and the reaction mixture was stirred for 1 hour at the same temperature. The reaction mixture was quenched with water and extracted with ethyl acetate. The organic layer was washed with water and brine solution and dried over anhydrous sodium sulphate. The solvent was evaporated under reduced pressure. Purification was performed on a silica gel column by using 30% ethyl acetate in hexane as eluent to get the title compound (24.5 g).

Step b: Synthesis of 3-{2-[(3aS,5R,6S,6aS)-5-{(E)-2-[4-(6-methoxypyridin-3-yl)phenyl]ethenyl}-2,2-dimethyltetrahydrofuro[2,3-d][1,3]dioxol-6-yl]ethyl}-1,2,3-benzotriazin-4(3H)-one A mixture of the compound obtained from step a above (12 g), 2-methoxy-5-pyridine boronic acid (7.4 g), tetrakistriphenylphosphinepalladium (0) (2.8 g), and potassium carbonate (10 g) was dried under high vacuum for 10 minutes, and dry dimethylformamide (60 ml) was added at room temperature. The reaction mixture was heated at 120° C. for 2 hours, and then quenched with water and extracted with ethyl acetate. The organic layer was washed with water and brine solution and dried over anhydrous sodium sulphate. The solvent was evaporated under reduced pressure to obtain a residue which was purified by column chromatography over silica gel using 40% ethyl acetate in hexane as eluant to afford the title compound (8.5 g).

Step c: Synthesis of 3-{2-[(3aS,5R,6S,6aS)-5-{2-[4-(6-methoxypyridin-3-yl)phenyl]ethyl}-2,2-dimethyltetrahydrofuro[2,3-d][1,3]dioxol-6-yl]ethyl}-1,2,3-benzotriazin-4(3H)-one To the solution of the compound obtained from step b above (8.5 g) in a solvent mixture of tetrahydrofuran:methanol (60 mL:40 mL), 10% palladium on charcoal (4 g) was added at room temperature, and the reaction mixture was hydrogenated with hydrogen at 35 psi for 4 hours in a Paar apparatus. The reaction mixture was filtered through a celite pad and the residue was washed with methanol. The filtrate was concentrated to afford the title compound (8.1 g).

Step d: Synthesis of 3-{2-[(2R,3R,4S,5R)-4,5-dihydroxy-2-{2-[4-(6-methoxypyridin-3-yl)phenyl]ethyl}tetrahydrofuran-3-yl]ethyl}-1,2,3-benzotriazin-4(3H)-one Perchloric acid (4.8 mL) was added to a solution of the compound obtained from step c above (8.1 g) in acetonitrile (50 mL) and water (8 mL) at room temperature. The reaction mixture was heated to 55° C. for 30 minutes. The reaction mixture was then quenched using sodium bicarbonate solution. The solvents were evaporated under reduced pressure. The residue thus obtained was taken up in ethyl acetate and water. The organic layer was separated, washed with water and brine solution, and dried over anhydrous sodium sulphate. The solvent was concentrated under reduced pressure to yield the title compound (8 g).

Step e: Synthesis of (2S,3R)-3-(formyloxy)-5-[4-(6-methoxypyridin-3-yl)phenyl]-2-[2-(4-oxo-1,2,3-benzotriazin-3(4H)-yl)ethyl]pentanoic acid To a solution of the compound obtained from step d above (8 g) in tert-butanol:tetrahydrofuran (40 mL:40 mL) at 0° C., a solution of sodium metaperiodate (14 g in 40 mL of water) was added. The reaction mixture was stirred for 2 hours at the same temperature, and potassium permangnate (518 mg) was added at 0° C. After stirring the reaction mixture for an additional 6 hours at room temperature, the reaction mixture was evaporated on a rotary evaporator. The residue was taken into water and extracted with ethyl acetate. The organic layer was washed with water and brine solution and dried over anhydrous sodium sulphate. The solvent was evaporated under the reduced pressure, to afford the title compound (8 g).

Step f: Synthesis of (2S,3R)-3-hydroxy-5-[4-(6-methoxypyridin-3-yl)phenyl]-2-[2-(4-oxo-1,2,3-benzotriazin-3(4H)-yl)ethyl]pentanoic acid Potassium carbonate (2.3 g) was added to a solution of the compound obtained from step e above (8 g) in methanol (40 mL) and tetrahydrofuran (30 mL) at 0° C. The reaction mixture was stirred at room temperature for 3 hours. The solvents were evaporated, and the residue was taken into water and ethyl acetate. The organic layer was washed with water and brine solution and dried over anhydrous sodium sulphate. The solvent was evaporated under reduced pressure to obtain a residue which was purified by column chromatography over silica gel using 60% ethyl acetate in hexane as eluant to afford the title compound (3 g).

Mass (m/z): 474.87 (M$^+$+1); $^1$H NMR (400 MHz, MeOD): δ 8.32-8.30 (2H, m), 8.16-8.14 (1H, m), 8.04-8.03 (1H, m), 7.92-7.88 (2H, m), 7.46 (2H, d, J=8 Hz), 7.24 (2H, m, J=8 Hz), 6.86 (1H, d, J=8 Hz), 4.57-4.53 (2H, m), 3.93 (3H, s), 3.78-3.83 (1H, m), 2.83-2.80 (1H, m), 2.63-2.60 (1H, m), 2.52-2.49 (1H, m), 2.32-2.28 (2H, m), 1.80-1.76 (2H, m).

Example 1B

Synthesis of (2S,3R)-3-hydroxy-5-[4-(6-hydroxypyridin-3-yl)phenyl]-2-[2-(4-oxo-1,2,3-benzotriazin-3(4H)-yl)ethyl]pentanoic acid (Compound No. 226)

To a solution of the compound obtained from Example 1A above (0.2 g) in dry toluene (5 mL), cooled to 78° C., boron tribromide (0.5 mL) was added and the contents were stirred at room temperature for 4 hours. Ethyl acetate and water were added to the reaction mixture. The organic layer was separated, washed with water and brine, and dried over anhydrous sodium sulfate. The solvent was evaporated to obtain a residue which was purified by preparatory thin layer chromatography (2 mm thickness) using 15% methanol in dichloromethane as eluent to get the title compound (60 mg).

Mass (m/z): 461.23 (M$^+$+1); $^1$HNMR (CD$_3$OD): 8.30 (d, 1H, J=8 Hz), 8.15 (d, 1H, J=8 Hz), 8.06-8.01 (m, 2H), 7.88 (t, 1H, J=8 Hz), 7.79-7.76 (m, 1H), 7.43 (d, 2H, J=12 Hz), 7.25 (d, 2H, J=12 Hz), 6.75 (d, 1H, J=12 Hz), 4.58-4.51 (m, 2H), 3.82-3.76 (m, 1H), 2.88-2.78 (m, 1H), 2.66-2.57 (m, 1H), 2.54-2.47 (m, 1H), 2.33-2.25 (m, 2H), 1.84-1.70 (m, 2H).

Example 1C

Synthesis of (2S,3R)-3-(acetyloxy)-5-[4-(6-methoxypyridin-3-yl)phenyl]-2-[2-(4-oxo-1,2,3-benzotriazin-3(4H)-yl)ethyl]pentanoic acid (Compound No. 229)

Diisopropyl azodicarboxylate (63 mg) was added to a solution of the compound obtained from Example 1A above (100 mg), tri-n-butylphosphine (93 mg), and acetic acid (1 mL) in dry tetrahydrofuran (3 mL) at 0° C. The reaction mixture was stirred for 1 hour and concentrated. The residue was taken in ethyl acetate, and washed with water and brine. The organic layer was concentrated to get an oily residue which was purified on preparative thin layer chromatography (2 mm thickness) using 10% methanol in dichloromethane to get the title compound (80 mg).

Mass (m/z): 517.06 (M$^+$+1); $^1$HNMR: δ 8.37 (m, 2H), 8.15 (d, 1H, J=8 Hz), 7.97-7.93 (m, 1H), 7.82-7.80 (m, 1H), 7.41 (d, 2H, J=8 Hz), 7.20 (d, 2H, J=8 Hz), 6.83 (d, 1H, J=8 Hz), 5.28-5.27 (m, 1H), 4.56-4.58 (m, 2H), 4.01 (s, 3H), 2.85-2.80 (m, 1H), 2.55-2.75 (m, 2H), 2.31-2.29 (m, 2H), 2.25-2.10 (m, 2H), 2.063 (s, 3H).

Example 1D

Synthesis of (2S,3R)-2-[2-(1,3-dioxo-1,3-dihydro-2H-isoindol-2-yl)ethyl]-3-hydroxy-5-[4-(6-methoxypyridin-3-yl)phenyl]pentanoic acid (Compound No. 88)

Step a: Synthesis of 5-O-[tert-butyl(diphenyl)silyl]-3-deoxy-3-[2-(1,3-dioxo-1,3-dihydro-2H-isoindol-2-yl)ethyl]-1,2-O-(1-methylethylidene)-β-D-lyxofuranose 5-O-[tert-butyl(diphenyl)silyl]-3-deoxy-3-(2-hydroxyethyl)-1,2-O-isopropylidene-β-D-lyxofuranose (14 g), triphenylphosphine (12 g), and phthalimide (5 g) were dried in a high vacuum in a round bottom flask for 10 minutes. Then the vacuum was released under a nitrogen atmosphere, and tetrahydrofuran (100 mL) was added to the above reaction mixture. The reaction mixture was cooled to 0° C. and diethyl azodicarboxylate (7.8 mL) was added slowly. The reaction mixture was stirred for 30 minutes at the same temperature, and then quenched with water and extracted with ethyl acetate. The organic layer was washed with water and brine solution, dried over anhydrous sodium sulphate, and concentrated to obtain a residue which was purified by column chromatography over silica gel using 30% ethyl acetate in hexane as eluant to afford the title compound (11 g).

Step b: Synthesis of 3-deoxy-3-[2-(1,3-dioxo-1,3-dihydro-2H-isoindol-2-yl)ethyl]-1,2-O-(1-methylethylidene)-β-D-lyxofuranose To a solution of the compound obtained from step a above (11 g) in dry tetrahydrofuran (50 mL) at 0° C., tetra-butyl ammonium fluoride (41.36 mL) was added. The resulting mixture was initially stirred at 0° C. for 1 hour, and then at room temperature for 4 hours. The reaction mixture was cooled to 0° C., quenched with saturated ammonium chloride, and extracted with ethyl acetate. The organic layer was washed with water and brine, dried over anhydrous sodium sulphate, and concentrated. The residue thus obtained was purified by column chromatography over silica gel using 80% ethyl acetate in hexane as eluant to furnish the title compound (5 g).

Step c: Synthesis of (5S)-3-deoxy-3-[2-(1,3-dioxo-1,3-dihydro-2H-isoindol-2-yl)ethyl]-4,5-O-(1-methylethylidene)-D-arabino-pentodialdo-5,2-furanose Oxalyl chloride (4.5 mL) and dichloromethane (20 mL) were taken in a three neck round bottom flask and cooled to −78° C. Dimethylsulfoxide (6.6 mL) was added drop-wise to the reaction mixture. The reaction mixture was warmed to −35° C. for 5 to 10 minutes and again cooled to −78° C. A solution of the compound obtained from step b above (7.2 g) in dichloromethane (20 mL) was added slowly while maintaining the same temperature. The reaction mixture was stirred for 45 minutes until the reaction temperature reached −35° C. The reaction mixture was again cooled to −78° C. and triethylamine (17.3 mL) was added. The reaction mixture was stirred for an additional 30 minutes, and the temperature was allowed to reach −35° C. The reaction mixture was quenched with saturated solution of ammonium chloride, and extracted with dichloromethane. The combined organic layers were washed with water and brine solution, dried over anhydrous sodium sulphate, and concentrated to furnish the title compound (7.3 g).

Step d: Synthesis of 2-(2-{(3aS,5R,6S,6aS)-5-[(E)-2-(4-bromophenyl)ethenyl]-2,2-dimethyltetrahydrofuro[2,3-d][1,3]dioxol-6-yl}ethyl)-1H-isoindole-1,3(2H)-dione To a suspension of potassium t-butoxide (2.3 g) in dimethyl sulfoxide (30 ml) cooled to 0° C., (4-bromobenzyl)triphenylphosphonium bromide (12.2 g) in dimethyl sulfoxide (20 mL) was added. After 20 minutes, a solution of compound obtained from step c above (4.1 g) in dimethyl sulfoxide (10 mL) was added drop-wise, and the reaction mixture was stirred for 1 hour at the same temperature. The reaction mixture was quenched with water, and extracted with ethyl acetate. The organic layer was washed with water and brine solution and dried over anhydrous sodium sulphate. The solvent was evaporated under reduced pressure. Purification was performed on silica gel column by using 40% ethyl acetate in hexane as eluant to furnish the title compound (4 g).

Step e: Synthesis of 2-{2-[(3aS,5R,6S,6aS)-5-{(E)-2-[4-(6-methoxypyridin-3-yl)phenyl]ethenyl}-2,2-dimethyltetrahydrofuro[2,3-d][1,3]dioxol-6-yl]ethyl}-1H-isoindole-1,3(2H)-dione A mixture of the compound obtained from step d above (1 g), 2-methoxy-5-pyridine boronic acid (0.614 g), tetrakistriphenylphosphinepalladium (0) (0.115 g), and potassium carbonate (0.832 g) was dried under high vacuum for 10 minutes, and dry dimethylformamide (8 mL) was added at room temperature. The reaction mixture was heated at 120° C. for 2 hours, and then quenched with water and extracted with ethyl acetate. The organic layer was washed with water and brine solution, and dried over anhydrous sodium sulphate. The solvent was evaporated under reduced pressure to obtain a residue which was purified by column chromatography over silica gel using 30% ethyl acetate in hexane as eluant to afford the title compound (0.62 g).

Step f: Synthesis of 2-{2-[(3aS,5R,6S,6aS)-5-{2-[4-(6-methoxypyridin-3-yl)phenyl]ethyl}-2,2-dimethyltetrahydrofuro[2,3-d][1,3]dioxol-6-yl]ethyl}-1H-isoindole-1,3(2H)-dione To a solution of the compound obtained from step e above (0.6 g) in methanol (10 mL), 10% palladium on charcoal (0.05 g) was added at room temperature and the reaction mixture was hydrogenated with hydrogen at 35 psi for 4 hours in a Paar apparatus. The reaction mixture was filtered through a celite pad and the residue was washed with methanol. The filtrate was concentrated to afford the title compound (0.56 g).

Step g: Synthesis of 2-{2-[(2R,3R,4S,5R)-4,5-dihydroxy-2-{2-[4-(6-methoxypyridin-3-yl)phenyl]ethyl}tetrahydrofuran-3-yl]ethyl}-1H-isoindole-1,3(2H)-dione Perchloric acid (0.4 mL) was added to a solution of the compound obtained from step f above (0.5 g) in acetonitrile (4 mL) and water (0.8 mL) at room temperature. The reaction mixture was heated to 55° C. for 30 minutes. The reaction mixture was then quenched using sodium bicarbonate solution. The solvents were evaporated under reduced pressure. The residue thus obtained was taken up in ethyl acetate and water. The organic layer was separated, washed with water and brine solution, and dried over anhydrous sodium sulphate. The solvent was concentrated under reduced pressure to yield the title compound (0.51 g).

Step h: Synthesis of (1R,2S)-4-(1,3-dioxo-1,3-dihydro-2H-isoindol-2-yl)-2-formyl-1-{2-[4-(6-methoxypyridin-3-yl)phenyl]ethyl}butyl formate To a solution of the compound obtained from step g above (0.56 g) in methanol (4 mL) at 0° C., a solution of sodium metaperiodate (0.736 g in 1 mL of water) was added. The reaction mixture was stirred for 2 hours at the same temperature. After stirring the reaction mixture for an additional 1 hour at room temperature, the reaction mixture was evaporated on a rotary evaporator. The residue was taken into water and extracted with ethyl acetate. The organic layer was washed with water and brine solution, and dried over anhydrous sodium sulphate. The solvent was evaporated under reduced pressure to obtain the title compound (0.54 g).

Step i: Synthesis of (2S,3R)-2-[2-(1,3-dioxo-1,3-dihydro-2H-isoindol-2-yl)ethyl]-3-(formyloxy)-5-[4-(6-methoxypyridin-3-yl)phenyl]pentanoic acid The compound obtained in step h (0.54 g) was taken in acetonitrile (6 mL) and water (1 mL). To this solution, sodium dihydrogen phosphate (0.054 g) was added. The reaction mixture was cooled to 0° C. and hydrogen peroxide (1 mL) and sodium chlorite (0.208 g) were added. After stirring the reaction mixture for an additional 1 hour, the solvents were evaporated on a rotary evaporator; the residue was taken into water and extracted with ethyl acetate. The organic layer was washed with water and brine solution, and dried over anhydrous sodium sulphate. The solvent was evaporated under reduced pressure to get the title compound (0.5 g).

Step j: Synthesis of (2S,3R)-2-[2-(1,3-dioxo-1,3-dihydro-2H-isoindol-2-yl)ethyl]-3-hydroxy-5-[4-(6-methoxypyridin-3-yl)phenyl]pentanoic acid Potassium carbonate (0.165 g) was added to a solution of the compound obtained from step i above (0.4 g) in methanol (6 mL) at 0° C. The reaction mixture was stirred at room temperature for 3 hours. The solvents were evaporated, and the residue was taken into water and ethyl acetate. The organic layer was washed with water and brine solution, and dried over anhydrous sodium sulphate. The solvent was evaporated under reduced pressure to obtain a residue which was purified with preparatory TLC using 7% methanol in ethyl acetate as eluent to get the title compound (0.13 gm).

Mass (m/z): 474.88 (M$^+$+1); $^1$HNMR (CDCl$_3$):— δ 8.35 (s, 1H), 7.83-7.81 (m, 2H), 7.77-7.69 (m, 3H), 7.42 (d, 2H, J=3 Hz), 7.25 (d, 2H, J=6 Hz), 6.80 (d, 1H, J=6 Hz), 3.97 (s, 3H), 3.87-3.78 (m, 3H), 2.89 (m, 1H), 2.69 (m, 1H), 2.57 (m, 1H), 2.15-1.98 (m, 2H), 1.84-1.79 (m, 2H).

Example 1E

Synthesis of (2S,3R)-5-(2',4'-difluorobiphenyl-4-yl)-2-[2-(1,3-dioxo-1,3-dihydro-2H-isoindol-2-yl)ethyl]-3-hydroxypentanoic acid (Compound No. 97)

Step a: Synthesis of 2-(2-{(3aS,5R,6S,6aS)-5-[(E)-2-(3',5'-difluorobiphenyl-4-yl)ethenyl]-2,2-dimethyltetrahydrofuro[2,3-d][1,3]dioxol-6-yl}ethyl)-1H-isoindole-1,3(2H)-dione A mixture of the compound obtained from step d of Example 1D above (0.2 g), 3,5-difluorophenyl boronic acid (0.135 g), tetrakistriphenylphosphinepalladium (0) (0.023 g), and potassium carbonate (0.2 g) was dried under high vacuum for 10 minutes and dry dimethylformamide (3 mL) was added at room temperature. The reaction mixture was heated at 120° C. for 2 hours, and then quenched with water and extracted with ethyl acetate. The organic layer was washed with water and brine solution, and dried over anhydrous sodium sulphate. The solvent was evaporated under reduced pressure to obtain a residue which was purified by column chromatography over silica gel using 30% ethyl acetate in hexane as eluant to afford the title compound (0.205 g).

Step b: Synthesis of 2-(2-{(3aS,5R,6S,6aS)-5-[2-(3', 5'-difluorobiphenyl-4-yl)ethyl]-2,2-dimethyltetrahydrofuro[2,3-d][1,3]dioxol-6-yl}ethyl)-1H-isoindole-1,3(2H)-dione To the solution of the compound obtained from step a above (0.2 g) in tetrahydrofuran (10 mL), 10% palladium on charcoal (0.1 g) was added at room temperature, and the reaction mixture was hydrogenated with hydrogen at 35 psi for 4 hours in a Paar apparatus. The reaction mixture was filtered through a celite pad, and the residue was washed with methanol. The filtrate was concentrated to afford the title compound (0.2 g).

Step c: Synthesis of 2-(2-{(2R,3R,4S,5R)-2-[2-(3',5'-difluorobiphenyl-4-yl)ethyl]-4,5-dihydroxytetrahydrofuran-3-yl}ethyl)-1H-isoindole-1,3(2H)-dione Perchloric acid (0.3 mL) was added to a solution of the compound obtained from step b above (0.2 g) in acetonitrile (6 mL) and water (2 mL) at room temperature. The reaction mixture was heated to 55° C. for 30 minutes. The reaction mixture was then quenched using sodium bicarbonate solution. The solvents were evaporated under reduced pressure. The residue thus obtained was taken up in ethyl acetate and water. The organic layer was separated and washed with water and brine solution, and dried over anhydrous sodium sulphate. The solvent was concentrated under reduced pressure to yield the title compound (0.15 g).

Step d: Synthesis of (1R,2S)-1-[2-(3',5'-difluorobiphenyl-4-yl)ethyl]-4-(1,3-dioxo-1,3-dihydro-2H-isoindol-2-yl)-2-formylbutyl formate To a solution of the compound obtained from step c above (0.15 g) in methanol (6 mL) at 0° C., a solution of sodium metaperiodate (0.15 g in 1 mL of water) was added. The reaction mixture was stirred for 2 hours at the same temperature. After stirring the reaction mixture for an additional 1 hour at room temperature, the reaction mixture was evaporated on a rotary evaporator. The residue was taken into water and extracted with ethyl acetate. The organic layer was washed with water and brine solution, and dried over anhydrous sodium sulphate. The solvent was evaporated under reduced pressure to obtain the title compound (0.12 g).

Step e: Synthesis of (2S,3R)-5-(3',5'-difluorobiphenyl-4-yl)-2-[2-(1,3-dioxo-1,3-dihydro-2H-isoindol-2-yl)ethyl]-3-(formyloxy)pentanoic acid The compound obtained from step d above (0.12 g) was taken in acetonitrile (6 mL) and water (1 mL). To this solution, sodium dihydrogen phosphate (0.05 g) was added. The reaction mixture was cooled to 0° C., and hydrogen peroxide (0.5 mL) and sodium chlorite (0.15 g) were added. After stirring the reaction mixture for an additional 1 hour, the solvents were evaporated on a rotary evaporator and the residue was taken into water and extracted with ethyl acetate. The organic layer was washed with water and brine solution, and dried over anhydrous sodium sulphate. The solvent was evaporated under reduced pressure, to get the title compound (0.12 g).

Step f: Synthesis of (2S,3R)-5-(3',5'-difluorobiphenyl-4-yl)-2-[2-(1,3-dioxo-1,3-dihydro-2H-isoindol-2-yl)ethyl]-3-hydroxypentanoic acid Potassium carbonate (0.06 g) was added to a solution of the compound obtained from step e above (0.12 g) in methanol (10 mL) at 0° C. The reaction mixture was stirred at room temperature for 3 hours. The solvents were evaporated, and the residue was taken into water and ethyl acetate. The organic layer was washed with water and brine solution, and dried over anhydrous sodium sulphate. The solvent was evaporated under reduced pressure to obtain a residue which was purified with preparatory thin layer chromatography using 10% methanol in ethyl acetate as eluent to get the title compound (0.025 gm).

Mass (m/z): 480.13 (M$^+$+1); $^1$HNMR (CD$_3$OD): δ 7.48-7.76 (m, 4H), 7.47-7.37 (m, 3H), 7.25-7.23 (d, 2H), 7.03-6.98 (m, 2H), 3.78-3.72 (m, 3H), 2.85-2.81 (m 1H), 2.65-2.63 (m, 1H), 2.42-2.40 (m, 1H), 2.10-2.05 (m, 2H), 1.79-1.75 (m, 2H).

Example 2

Synthesis of (2S,3R)-3-hydroxy-2-[2-(4-oxo-1,2,3-benzotriazin-3(4H)-yl)ethyl]-5-phenylpentanoic acid (Compound No. 82)

Step a: Synthesis of 3-{2-[(3aS,5R,6S,6aS)-2,2-dimethyl-5-(2-phenylethyl)tetrahydrofuro[2,3-d][1,3]dioxol-6-yl]ethyl}-1,2,3-benzotriazin-4(3H)-one To the solution of the compound obtained from step j of Example 1 (0.3 g) in a solvent mixture of tetrahydrofuran:methanol (10 mL:10 mL) palladium/carbon (0.2 g, 10%) was added at room temperature, and the reaction mixture was hydrogenated at 35 psi for 4 hours in a Paar apparatus. The reaction mixture was filtered through a celite pad and the residue was washed with methanol. The filtrate was concentrated to afford the title compound (0.3 g).

Mass (m/z): 421 (M$^+$)

Step b: Synthesis of 3-{2-[(2R,3R,4S,5R)-4,5-dihydroxy-2-(2-phenylethyl)tetrahydrofuran-3-yl]ethyl}-1,2,3-benzotriazin-4(3H)-one Perchloric acid (0.2 mL) was added to a solution of the compound obtained from step a above (0.3 g) in acetonitrile (4 mL) and water (0.3 mL) at room temperature. The reaction mixture was heated to 55° C. for 30 minutes. The reaction mixture was then quenched using a sodium bicarbonate solution. The solvents were evaporated at reduced pressure. The residue thus obtained was taken up in ethyl acetate and water. The organic layer was separated, washed with water and brine solution, and dried over anhydrous sodium sulphate. The solvent was concentrated under reduced pressure to yield the title compound (0.3 g).

Step c: Synthesis of (2S,3R)-3-(formyloxy)-2-[2-(4-oxo-1,2,3-benzotriazin-3(4H)-yl)ethyl]-5-phenylpentanoic acid To a solution of the compound obtained from step b above (0.3 g) in tert-butanol:tetrahydrofuran (3 mL:3 mL) at 0° C., a solution of sodium metaperiodate (0.673 g in 3 mL of water) was added. The reaction mixture was stirred for 2 hours at the same temperature and potassium permanganate (0.025 g) was added at 0° C. After stirring the reaction mixture for an additional 6 hours at room temperature, the reaction mixture was evaporated and the residue was taken into water and extracted with ethyl acetate. The organic layer was washed with water and brine solution, and dried over anhydrous sodium sulphate. The solvent was evaporated under reduced pressure, to afford the title compound (0.3 g).

Step d: Synthesis of (2S,3R)-3-hydroxy-2-[2-(4-oxo-1,2,3-benzotriazin-3(4H)-yl)ethyl]-5-phenylpentanoic acid Potassium carbonate (0.11 g) was added to a solution of the compound obtained from step c above (0.3 g) in methanol (4 mL) and tetrahydrofuran (4 mL) at 0° C. The reaction mixture was stirred at room temperature for 3 hours. The solvents were evaporated, and the residue was taken into water and ethyl acetate. The organic layer was washed with water and brine solution, and dried over anhydrous sodium sulphate. The solvent was evaporated under reduced pressure to obtain a residue which was purified by column chromatography over silica gel using 10% methanol in dichloromethane as eluant to afford the title compound (0.020 g).

Mass (m/z): 368.0 (M$^+$+1); $^1$HNMR (CD$_3$OD): δ 8.31 (d, 1H, J=8 Hz), 8.15 (d, 1H, J=8 Hz), 8.06-8.02 (m, 1H), 7.91-7.89 (m, 2H), 7.62 (d, 2H, J=8 Hz), 7.36 (d, 1H, J=8 Hz), 7.21-7.07 (m, 1H), 4.57-4.52 (m, 2H), 3.78-3.76 (m, 1H), 2.76-2.75 (m, 1H), 2.57-2.49 (m, 2H), 2.29-2.27 (m, 2H), 1.74-1.71 (m, 2H).

Example 3

Synthesis of (2S,3R)-2-[2-(1,3-dioxo-1,3-dihydro-2H-isoindol-2-yl)ethyl]-3-hydroxy-5-[4(trifluoromethyl)phenyl]pentanoic acid (Compound No. 84)

Step a: Synthesis of 5-O-[tert-butyl(diphenyl)silyl]-3-deoxy-3-[2-(1,3-dioxo-1,3-dihydro-2H-isoindol-2-yl)ethyl]-1,2-O-isopropylidene-β-D-lyxofuranose A mixture of the compound obtained from step f of Example 1 (0.14 g), triphenylphosphine (0.080 g), and pthalimide (0.045 g) was taken in a round bottom flask and dried in high vacuum for 10 minutes. The vacuum was released under a nitrogen atmosphere and tetrahydrofuran (5 mL) was added to the reaction mixture. The reaction mixture was cooled to 0° C. and diethyl azodicarboxylate (0.1 mL) was added slowly. The reaction mixture was stirred for 30 minutes at the same temperature, and then quenched with water and extracted with ethyl acetate. The organic layer was washed with water and brine solution, dried over anhydrous sodium sulphate, and concentrated. The residue thus obtained was purified by column chromatography over silica gel using 30% ethyl acetate in hexane as eluant to afford the title compound (0.11 g).

Mass (m/z): 608 (M$^+$+23)

Step b: Synthesis of 3-deoxy-3-[2-(1,3-dioxo-1,3-dihydro-2H-isoindol-2-yl)ethyl]-1,2-O-isopropylidene-β-D-lyxofuranose To a solution of the compound obtained from step a above (0.060 g) in dry tetrahydrofuran (2 mL) at 0° C., tetra-butyl ammonium fluoride (0.2 mL) was added. The resulting mixture was initially stirred at 0° C. for 1 hour, and then at room temperature for 4 hours. The reaction mixture was cooled to 0° C., quenched with saturated ammonium chloride, and extracted with ethyl acetate. The organic layer was washed with water and brine, dried over anhydrous sodium sulphate, and concentrated. The residue thus obtained was purified by column chromatography over silica gel using 60% ethyl acetate in hexane as eluant to furnish the title compound (0.4 g).

Step c: Synthesis of (5S)-3-deoxy-3-[2-(1,3-dioxo-1,3-dihydro-2H-isoindol-2-yl)ethyl]-4,5-O-isopropylidene-D-arabino-pentodialdo-5,2-furanose In a three-neck round bottom flask, oxalyl chloride (0.6 mL) and dichloromethane (20 mL) were placed and cooled to –78° C. Dimethylsulfoxide (1 mL) was added drop-wise to the reaction mixture. The reaction mixture was warmed to –35° C. for 5 to 10 minutes, and again cooled to –78° C. A solution of the compound obtained from step b above (1 g) in dichloromethane (5 mL) was added slowly while maintaining the same temperature. The reaction mixture was stirred for 45 minutes until the reaction temperature reached –35° C. The reaction mixture was again cooled to –78° C., and triethylamine (2.4 mL) was added. The reaction mixture was stirred for an additional 30 minutes and the temperature was allowed to reach –35° C. The reaction mixture was quenched with a saturated solution of ammonium chloride, and extracted with dichloromethane. The combined organic layer was washed with water and brine solution, dried over anhydrous sodium sulphate, and concentrated to furnish the title compound (1.0 g).

Step d: Synthesis of 2-{2-[(3aS,5R,6S,6aS)-2,2-dimethyl-5-{(E)-2-[4-(trifluoromethyl) phenyl] vinyl}tetrahydrofuro[2,3-d][1,3]dioxol-6-yl]ethyl}-1H-isoindole-1,3(2H)-dione To a suspension of triphenyl[4-(trifluoromethyl)benzyl] phosphonium bromide (0.795 g) in dimethylsulphoxide (5 mL), potassium tert-butoxide (0.292 g) was added. A solution of the compound obtained from step c above (0.5 g) in tetrahydrofuran (7 mL) was added drop-wise after 20 minutes, and the reaction mixture was stirred for 1 hour at the same temperature. The reaction mixture was quenched with water, and extracted with ethyl acetate. The organic layer was washed with water and brine solution and dried over anhydrous sodium sulphate. The solvent was evaporated under reduced pressure and the residue thus obtained was purified by column chromatography using 30% ethyl acetate in hexane as eluant to furnish the title compound (0.25 g).

Mass (m/z): 487 (M$^+$)

Step e: Synthesis of 2-{2-[(3aS,5R,6S,6aS)-2,2-dimethyl-5-{2-[4-(trifluoromethyl)phenyl] ethyl}tetrahydrofuro[2,3-d][1,3]dioxol-6-yl]ethyl}-1H-isoindole-1,3(2H)-dione 10% Palladium on charcoal (0.2 g) was added to the solution of compound obtained from step d above (0.25 g) in ethyl acetate (20 mL) at room temperature, and the reaction mixture was hydrogenated at 50 psi for 4 hours in a Paar apparatus. The reaction mixture was filtered through a celite pad, and the residue was washed with methanol. The filtrate was concentrated to afford the title compound (0.225 g).

Step f: Synthesis of 2-{2-[(2R,3R,4S,5R)-4,5-dihydroxy-2-{2-[4-(trifluoromethyl)phenyl] ethyl}tetrahydrofuran-3-yl]ethyl}-1H-isoindole-1,3 (2H)-dione Perchloric acid (0.2 mL) was added to a solution of the compound obtained from step e above (0.225 g) in acetonitrile (4 mL), water (1 mL), and tetrahydrofuran (0.5 mL) at room temperature. The reaction mixture was heated to 55° C. for 30 minutes. The reaction mixture was then quenched using a sodium bicarbonate solution. The solvents were evaporated at reduced pressure. The residue thus obtained was taken in ethyl acetate and water. The organic layer was separated, washed with water and brine solution, and dried over anhydrous sodium sulphate. The solvent was concentrated under reduced pressure to yield the title compound (0.22 g).

Step g: Synthesis of (1R,2S)-4-(1,3-dioxo-1,3-dihydro-2H-isoindol-2-yl)-2-formyl-1-{2-[4-(trifluoromethyl)phenyl]ethyl}butyl formate A solution of sodium metaperiodate (0.313 g in 1 mL of water) was added to a solution of the compound obtained from step f above (0.22 g) in methanol:tetrahydrofuran (3 mL:1 mL) at 0° C. The reaction mixture was stirred for 2 hours at same temperature. After stirring the reaction mixture for an additional 6 hours at room temperature, the reaction mixture was evaporated on a rotary evaporator, and the residue was taken into water and extracted with ethyl acetate. The organic layer was washed with water and brine solution, and dried over anhydrous sodium sulphate. The solvent was evaporated under reduced pressure to afford the title compound (0.22 g).

Step h: Synthesis of (2S,3R)-2-[2-(1,3-dioxo-1,3-dihydro-2H-isoindol-2-yl)ethyl]-3-(formyloxy)-5-[4-(trifluoromethyl)phenyl]pentanoic acid To a solution of the compound obtained from step g above (0.22 g) in a solvent mixture of acetonitrile:water (3 mL:1 mL) at 0° C., sodium dihydrogenphosphate (0.021 g), sodium chlorite (0.081 g) and hydrogen peroxide (1 mL, 30% in water) were added. The reaction mixture was stirred for 2 hours at room temperature. The solvents were evaporated under reduced pressure to obtain a residue. Ethyl acetate and water were added to the resulting residue. The organic layer was separated, washed with water and brine, and dried over anhydrous sodium sulphate. The solvent was evaporated under reduced pressure to afford the title compound (0.2 g).

Step i: Synthesis of (2S,3R)-2-[2-(1,3-dioxo-1,3-dihydro-2H-isoindol-2-yl)ethyl]-3-hydroxy-5-[4-(trifluoromethyl)phenyl]pentanoic acid Potassium carbonate (0.178 g) was added to a solution of the compound obtained from step h above (0.2 g) in methanol (7 mL) at 0° C. The reaction mixture was stirred at room temperature for 3 hours. The solvents were evaporated, and the residue was taken into water and ethyl acetate. The organic layer was washed with water and brine solution, and dried over anhydrous sodium sulphate. The solvent was evaporated under reduced pressure to obtain a residue which was purified by column chromatography over silica gel using 10% methanol in dichloromethane as eluant to afford the title compound (0.090 g).

Mass (m/z): 458.0 (M$^+$+23)

$^1$HNMR (CD$_3$OD): δ 7.83 (q, 2H, J=3.1 Hz), 7.71 (t, 2H, J=3.2 Hz), 7.51 (d, 2H, J=7.6 Hz), 7.28 (d, 2H, J=7.9 Hz), 3.95-3.76 (m, 3H), 2.93-2.55 (m, 3H), 2.14-1.75 (m, 4H).

Example 4

Synthesis of (2R,3R)-5-(4'-chlorobiphenyl-4-yl)-2-[2-(1,3-dioxo-1,3-dihydro-2H-isoindol-2-yl)ethyl]-3-hydroxypentanoic acid (Compound No. 89)

Step a: Synthesis of 1,2:5,6-Di-O-isopropyliden-α-D-ribo-3-hexulo-furanose

Oxalyl chloride (25.16 mL) and dichloromethane (200 mL) were taken in a three-neck round bottom flask and cooled to −75° C. under a nitrogen atmosphere. Then dimethylsulfoxide (27.3 mL) was added drop-wise slowly maintaining the temperature at −70° C. The reaction mixture was stirred for 30 minutes at the same temperature, and then diacetone-α-D-glucose (50 g) in dichloromethane (500 mL) was charged slowly, maintaining the temperature at −70° C. After 20 minutes, triethylamine (80 mL) was added drop-wise to the above mixture at the same temperature. A saturated solution of ammonium chloride in water (500 mL) was charged to the reaction mixture after 30 minutes, and the temperature was allowed to rise to room temperature. The reaction mixture was extracted with dichloromethane. The organic layer was dried over anhydrous sodium sulphate. The solvent was evaporated under reduced pressure to afford the title compound (45 g).

Step b: Synthesis of 1,2:5,6-Di-O-isopropylidene-3-deoxy-3-(2-ethoxy-2-oxoethylidene)-α-D-ribo-hexo-furanose To a suspension of sodium hydride (0.155 g, 60% in oil) in tetrahydrofuran (5 mL), triethyl phosphonoacetate (1.55 mL) was charged at 0° C. After 20 minutes, a solution of the compound obtained from step a above (1 g) in tetrahydrofuran (3 mL) was added drop-wise and the reaction mixture was stirred for 1 hour at the same temperature. A saturated solution of ammonium chloride was added to the reaction mixture. The resulting mixture was extracted with ethyl acetate. The combined extracts were dried over anhydrous sodium sulphate, and evaporated under reduced pressure to yield a residue which was purified by column chromatography over silica gel using 30% ethyl acetate in hexane as eluant to afford the title compound (1.3 g).

Mass (m/z): 351.1 (M$^+$+23)

Step c: Synthesis of 1,2:5,6-Di-O-isopropylidene-3-deoxy-3-(2-ethoxy-2-oxoethyl)-α-D-allofuranose 10% Palladium on charcoal (0.05 g) was added to the solution of the compound obtained from step b above (0.15 g) in ethyl acetate (10 mL) at room temperature, and hydrogen was supplied at 50 psi for 4 hours. The reaction mixture was filtered through a celite pad and the residue was washed with ethyl acetate. The filtrate was concentrated to afford the title compound (0.12 g).

Mass (m/z): 353.2 (M$^+$+1).

Step d: Synthesis of 3-deoxy-3-(2-ethoxy-2-oxoethyl)-1,2-O-isopropylidene-α-D-allofuranose 30% Perchloric acid (4 mL) was added to a solution of the compound obtained from step c above (2.0 g) in tetrahydrofuran (20 mL) at −5° C. to 0° C. The reaction mixture was stirred for 5 hours at −5° C. to 0° C. and then quenched with a saturated solution of sodium bicarbonate (20 mL). The solvents were evaporated, and ethyl acetate and water were added to the resulting residue. The organic layer was separated, washed with brine, dried over anhydrous sodium sulphate, and concentrated to afford the title compound (1.5 g).

Mass (m/z): 313.2 (M$^+$+1)

Step e: Synthesis of 3-deoxy-3-(2-ethoxy-2-oxoethyl)-1,2-O-isopropylidene-α-D-ribo-pentodialdo-1,4-furanose To a solution of the compound obtained from step d above (1.5 g) in methanol (15 mL), an aqueous solution of sodium periodate (1.65 g in 10 mL of water) was added at 0° C. The reaction mixture was stirred for 3 hours and brought from 0° C. to room temperature. The solvents were evaporated. Ethyl acetate and water were added to the residue. The organic layer was separated, washed with brine, dried over anhydrous sodium sulphate, and concentrated to afford the title compound (0.9 g).

Mass (m/z): 259.2 (M$^+$+1)

Step f: Synthesis of ethyl {(3aR,5R,6R,6aR)-5-[(E)-2-(4-bromophenyl)vinyl]-2,2-dimethyltetrahydrofuro[2,3-d][1,3]dioxol-6-yl}acetate To a suspension of (4-bromobenzyl)triphenylphosphonium bromide (2.67 g) in dimethylsulphoxide (15 mL), potassium tert-butoxide (0.508 g) was added at 0° C. After stirring the reaction mixture for 30 minutes at room temperature, a solution of the compound obtained from step e above (0.9 g) in tetrahydrofuran (5 mL) was added drop-wise at 0° C. The reaction mixture was stirred for 2 hours and brought from 0° C. to room temperature, and quenched with ice cold water. The solvents were evaporated, and ethyl acetate and water were added to resulting residue. The organic layer was separated, washed with water and brine solution, and dried over anhydrous sodium sulphate. The solvent was evaporated under reduced pressure, and the residue thus obtained was purified by column chromatography using 10% ethyl acetate in hexane as eluant to furnish the title compound (1.0 g).

Mass (m/z): 413.3 (M$^+$+1)

Step g: Synthesis of ethyl {(3aR,5R,6R,6aR)-5-[(E)-2-(4'-chlorobiphenyl-4-yl)vinyl]-2,2-dimethyltetrahydrofuro[2,3-d][1,3]dioxol-6-yl}acetate A mixture of the compound obtained from step f above (1.0 g) (4-chlorophenyl)boronic acid (0.76 g), tetrakis(triphenylphosphine)palladium (0) (0.14 g), and potassium carbonate (1.0 g) in dry dimethylformamide (10 mL) was heated at 110° C. for 4 hours. Ethyl acetate and water were added to the reaction mixture. The organic layer was separated, washed with water and brine solution, and dried over anhydrous sodium sulphate. The solvent was evaporated under reduced pressure to obtain a residue which was purified by column chromatography over silica gel using 12% ethyl acetate in hexane as eluant to afford the title compound (0.9 g).

Mass (m/z): 465.2 (M$^+$+23)

Step h: Synthesis of ethyl {(3aR,5R,6R,6aR)-5-[2-(4'-chlorobiphenyl-4-yl)ethyl]-2,2-dimethyltetrahydrofuro[2,3-d][1,3]dioxol-6-yl}acetate To a solution of the compound obtained from step g above (0.8 g) in ethyl acetate (15 mL), 10% palladium on charcoal (0.25 g) was added at room temperature. The system was evacuated with hydrogen and the reaction mixture was stirred for 4 hours at room temperature under a hydrogen atmosphere. The reaction mixture was filtered through a celite pad, and concentrated to afford the title compound (0.75 g).

Mass (m/z): 415.4 (M$^+$−28)

Step i: Synthesis of 2-{(3aR,5R,6R,6aR)-5-[2-(4'-chlorobiphenyl-4-yl)ethyl]-2,2-dimethyltetrahydrofuro[2,3-d][1,3]dioxol-6-yl}ethanol To a solution of the compound obtained from step h above (0.75 g) in tetrahydrofuran (15 mL), lithium aluminum hydride (0.096 g) was added at 0° C. The resulting mixture was stirred for 3 hours at same temperature, and a saturated solution of ammonium chloride was then added. The reaction mixture was then filtered through silica gel (100 to 200 mesh) and concentrated. Ethyl acetate and water were added to the resulting residue. The organic layer was separated, washed with water and brine, dried over anhydrous sodium sulphate, filtered, and concentrated under reduced pressure to afford the title compound (0.65 g).

Mass (m/z): 425.2 (M$^+$+23)

Step j: Synthesis of 2-{(3aR,5R,6R,6aR)-5-[2-(4'-chlorobiphenyl-4-yl)ethyl]-2,2-dimethyltetrahydrofuro[2,3-d][1,3]dioxol-6-yl}ethyl methanesulfonate Triethylamine (0.43 ml) and methanesulfonyl chloride (0.21 mL) were added to a solution of the compound obtained from step i above (0.6 g) in dichloromethane (15 mL) at 0° C. The reaction mixture was stirred at room temperature for 2 hours. Dichloromethane and water were added to reaction mixture. The organic layer was separated, washed with water, dried, and concentrated under reduced pressure to furnish the title compound (0.6 g).

Step k: Synthesis of 2-(2-{(3aR,5R,6R,6aR)-5-[2-(4'-chlorobiphenyl-4-yl)ethyl]-2,2-dimethyltetrahydrofuro[2,3-d][1,3]dioxol-6-yl}ethyl)-1H-isoindole-1,3(2H)-dione Potassium phthalimide (0.051 g) was added in one portion to a stirred solution of the compound obtained from step j above (0.12 g) in dimethylformamide (5 mL) at room temperature under a nitrogen atmosphere. The resulting solution was heated at 50° C. for about 14 hours and then cooled to room temperature. Ethyl acetate and water were added to the reaction mixture. The organic layer was separated, washed with water and brine, and dried over anhydrous sodium sulphate. The organic phase was evaporated to dryness under reduced pressure. The residue thus obtained was purified by column chromatography using 30% ethyl acetate in hexane as eluant to furnish the title compound (0.1 g).

Mass (m/z): 549.5 (M$^+$+NH$_4^+$)

Step l: Synthesis of 2-(2-{(2R,3S,4R,5S)-2-[2-(4'-chlorobiphenyl-4-yl)ethyl]-4,5-dihydroxytetrahydrofuran-3-yl}ethyl)-1H-isoindole-1,3(2H)-dione Trifluoroacetic acid (1 mL) and water (0.5 mL) were added to the compound obtained from step k above (0.04 g). The reaction mixture was stirred at room temperature for 2 hours. The solvents were evaporated at reduced pressure. The residue thus obtained was taken in ethyl acetate and water. The organic layer was separated, washed with water and brine solution, and dried over anhydrous sodium sulphate. The solvent was concentrated under reduced pressure to yield the title compound (0.028 g).

Step m: Synthesis of (2R,3R)-5-(4'-chlorobiphenyl-4-yl)-2-[2-(1,3-dioxo-1,3-dihydro-2H-isoindol-2-yl)ethyl]-3-(formyloxy)pentanoic acid To a solution of the compound obtained from step 1 above (0.028 g) in a tert-butanol:water (2:3; 1.3 mL), sodium metaperiodate (0.051 g) was added at room temperature. The reaction mixture was stirred for 2 hours at the same temperature, and potassium permanganate (0.001 g) was added at 0° C. After stirring the reaction mixture for an additional 6 hours at room temperature, the reaction mixture was evaporated on a rotary evaporator, and the residue was taken into water and extracted with ethyl acetate. The organic layer was washed with water and brine solution, and dried over anhydrous sodium sulphate. The solvent was evaporated under the reduced pressure to afford the title compound (0.025 g).

Step n: Synthesis of (2R,3R)-5-(4'-chlorobiphenyl-4-yl)-2-[2-(1,3-dioxo-1,3-dihydro-2H-isoindol-2-yl)ethyl]-3-hydroxypentanoic acid Potassium carbonate (0.007 g) was added to a solution of the compound obtained from step m above (0.025 g) in methanol (1 mL) at 0° C. The reaction mixture was stirred at room temperature for 3 hours. The solvents were evaporated and the residue was taken into water and ethyl acetate. The organic layer was washed with water and brine solution, and dried over anhydrous sodium sulphate. The solvent was evaporated under reduced pressure to obtain a residue which was purified by column chromatography over silica gel using 10% methanol in dichloromethane as eluant to afford the title compound (0.014 g).

Mass (m/z): 478.2 (M$^+$+1)
$^1$HNMR (CD$_3$OD): δ 7.83 (q, 2H, J=4 Hz), 7.77 (q, 2H, J=4 Hz), 7.56 (d, 2H, J=8 Hz), 7.48 (d, 2H, J=8 Hz), 7.40 (d, 2H, J=8 Hz), 7.26 (d, 1H, J=8 Hz), 3.83-3.70 (m, 3H), 2.85-2.49 (m, 3H), 1.92-1.70 (m, 4H).

Example 5

Synthesis of (2R,3S)-2-[2-(1,3-dioxo-1,3-dihydro-2H-isoindol-2-yl)ethyl]-5-3'-fluoro-4'-methylbiphenyl-4-yl)-3-hydroxypentanoic acid (Compound No. 205)

Step a: Synthesis of 3-O-Acetyl-1,2:5,6-di-O-isopropylidene-α-D-erythrohexofuran-3-enose Acetic anhydride (65.77 mL) was added to a solution of the compound obtained from step a of Example 4 (45 g) in pyridine (500 mL) and the reaction mixture was heated at 60° C. for overnight. The reaction mixture was then concentrated to obtain a residue. Ethyl acetate and water were added to the residue. The organic layer was separated and washed with dilute hydrochloric acid, water, and brine. The solvent was evaporated under reduced pressure and the residue thus obtained was purified by silica gel column chromatography using 8% ethyl acetate in hexane as eluant to furnish the title compound (21 g).

Mass (m/z): 301.19 (M$^+$+1)

Step b: Synthesis of 3-O-acetyl-1,2:5,6-di-O-isopropylidene-α-D-gulofuranose

To a solution of the compound obtained from step a above (26 g) in ethyl acetate (250 mL), 10% palladium on charcoal (6 g) was added and the reaction mixture was shaken under hydrogen atmosphere at 60 psi for 4 hours on Paar apparatus. The reaction mixture was filtered through a celite bed. The solvents were evaporated to obtain a crude residue which was purified using column chromatography over silica gel using 15% ethyl acetate in hexane as eluant to furnish the title compound (17 g).

Mass (m/z): 324.97 (M$^+$+Na)

Step c: Synthesis of 1,2:5,6-di-O-isopropylidene-α-D-gulofuranose

Sodium methoxide (12.5 g) was added to a solution of the compound obtained from step b above (64 g) in methanol (10 mL). The reaction mixture was stirred for 3 hours at 0° C. The reaction mixture was then concentrated. The residue thus obtained was purified by column chromatography over silica gel using 30% ethyl acetate in hexane as eluant to afford the title compound (31 g).

Mass (m/z): 261.26 (M$^+$+1)

Step d: Synthesis of 1,2:5,6-di-O-isopropylidene-α-D-xylo-hexofuranos-3-ulose

Sodium hypochlorite (225 mL, 4% solution) was added drop-wise to a solution of the compound obtained from step c above (30 g), followed by the addition of 2,2,6,6-tetramethylpiperidine N-oxyl (0.18 g), potassium bromide (10.62 g), and sodium acetate (14.19 g) in ethyl acetate (300 mL) and water (100 mL). After 20 minutes, triethylamine (3.3 mL) was added drop-wise to the above mixture at the same temperature. The reaction mixture was extracted with ethyl acetate after 30 minutes. The organic layer was dried over anhydrous sodium sulphate. The solvent was evaporated under reduced pressure to afford the title compound (10.4 g).

Step e: Synthesis of 1,2:5,6-Di-O-isopropylidene-3-deoxy-3-(2-ethoxy-2-oxoethylidene)-α-D-xylo-hexofuranose To the solution of the compound obtained from step d above (10.5 g) in tetrahydrofuran, carboethoxymethylene triphenyl-phosphorane (27 g) was added. The reaction mixture was refluxed for 2 hours and concentrated to afford crude compound, which was purified by column chromatography over silica gel using 8% ethyl acetate in hexane as eluant to yield the title compound (5.0 g).

Mass (m/z): 350.28 (M$^+$+Na)

Step f: Synthesis of 1,2:5,6-Di-O-isopropylidene-3-deoxy-3-(2-ethoxy-2-oxoethyl)-α-D-gulofuranose 10% Palladium on charcoal (3 g) was added to a solution of the compound obtained from step e above (12 g) in methanol (50 mL) and the reaction mixture was stirred under hydrogen atmosphere at room temperature for 4 hours. The reaction mixture was filtered through a celite pad and the residue was washed using ethyl acetate. The filtrate was concentrated to furnish the title compound (12 g).

Mass (m/z): 330.9 (M$^+$+1).

Step g: Synthesis of 1,2:5,6-Di-O-isopropylidene-3-deoxy-3-(2-hydroxyethyl)-α-D-gulofuranose To a suspension of lithium aluminum hydride (2.37 g) in tetrahydrofuran (120 mL), a solution of the compound obtained from step f above (12 g) in tetrahydrofuran (100 mL) was added at −50° C. The reaction mixture was allowed to attain the temperature 0° C. and the mixture was stirred for 30 minutes at 0° C. The reaction mixture was quenched using an aqueous solution of ammonium chloride (25 mL). The reaction mixture was slowly allowed to attain room temperature and was further stirred for 12 hours at same temperature. The reaction mixture was filtered through a celite pad, and the residue was washed with ethyl acetate. The organic layer was dried over anhydrous sodium sulphate. The solvent was evaporated under reduced pressure to afford the title compound (8.5 g).

Step h: Synthesis of 1,2:5,6-Di-O-isopropylidene-3-deoxy-3-[2-(1,3-dioxo-1,3-dihydro-2H-isoindol-2-yl)ethyl]-α-D-gulofuranose A mixture of the compound obtained from step g above (8.5 g), triphenyl phosphine (21.83 g), and phthalimide (6.73 g) were taken in a round bottom flask and dried in high vacuum for 10 minutes. Then the vacuum was released under a nitrogen atmosphere and tetrahydrofuran (100 mL) was added to the reaction mixture. The reaction mixture was cooled to 0° C. and diisopropyl azodicarboxylate (12.625 g) was added slowly. The reaction mixture was stirred for 30 minutes at the same temperature and then quenched with water and extracted with ethyl acetate. The organic layer was washed with water and brine solution, dried over anhydrous sodium sulphate, and concentrated. The residue thus obtained was purified by column chromatography over silica gel using 40% ethyl acetate in hexane as eluant to afford the title compound (8.5 g).

Step i: Synthesis of 3-deoxy-3-[2-(1,3-dioxo-1,3-dihydro-2H-isoindol-2-yl)ethyl]-1,2-O-(isopropylidene)-α-D-gulofuranose 30% Perchloric acid (8.15 mL) was added to a solution of the compound obtained from step h above (0.8 g) in tetrahydrofuran (200 mL). The reaction mixture was stirred for 2 hours at 0° C. to 5° C. and then quenched with a saturated solution of sodium hydrogen carbonate. Ethyl acetate and water were added to the resulting mixture. The organic layer was separated, washed with brine, dried over anhydrous sodium sulphate, and concentrated. The residue thus obtained was purified by column chromatography over silica gel using 60% ethyl acetate in hexane to afford the title compound (5.5 g).
Mass (m/z): 377.24 (M$^+$+1)

Step j: Synthesis of (5R)-3-deoxy-3-[2-(1,3-dioxo-1,3-dihydro-2H-isoindol-2-yl)ethyl]-4,5-O-(1-methylethylidene)-L-arabino-pentodialdo-5,2-furanose To a solution of the compound obtained from step i above (5.5 g) in acetone (100 mL), an aqueous solution of sodium periodate (9.33 g in 100 mL) was added at 0° C. The reaction mixture was stirred for 2 hours, then filtered and concentrated. The residue thus obtained was taken in distilled water and extracted with ethyl acetate. The organic layer was dried over sodium sulphate and concentrated to afford the title compound (5.2 g).

Step k: Synthesis of 2-(2-{(3aR,5S,6R,6aR)-5-[(E)-2-(4-bromophenyl)ethenyl]-2,2-dimethyltetrahydrofuro[2,3-d][1,3]dioxol-6-yl}ethyl)-1H-isoindole-1,3(2H)-dione A solution of (4-bromobenzyl)triphenylphosphonium bromide (13.3 g) in dimethyl sulphoxide (10 mL) was added drop-wise to a suspension of sodium hydride (1 g of 50% suspension) in dimethyl sulphoxide (20 mL) at 0° C. After 20 minutes, a solution of the compound obtained from step j above (6 g) in dimethylsulphoxide (100 mL) was added drop-wise and the reaction mixture was stirred for 1 hour at the same temperature. The reaction mixture was quenched with water and extracted with ethyl acetate. The organic layer was washed with water and brine solution and dried over anhydrous sodium sulphate. The solvent was evaporated under reduced pressure to obtain a residue which was purified by column chromatography over silica gel using 40% ethyl acetate in hexane to furnish the title compound (5.5 g).
Mass (m/z): 499.10 (M$^+$+1)

Step l: Synthesis of 2-(2-{(3aR,5S,6R,6aR)-5-[(E)-2-(3'-fluoro-4'-methylbiphenyl-4-yl)ethenyl]-2,2-dimethyltetrahydrofuro[2,3-d][1,3]dioxol-6-yl}ethyl)-1H-isoindole-1,3(2H)-dione A mixture of the compound obtained from step k above (0.5 g), 3-fluoro-4-methylphenylboronic acid (0.314 g), tetrakistriphenylphosphinepalladium (0) (0.057 g), and potassium carbonate (0.414 g) was dried under high vacuum for 10 minutes. The vacuum was released under nitrogen atmosphere and dry dimethylformamide (5 mL) was added at room temperature. The reaction mixture was heated at 120° C. for 2 hours, and then quenched with water and extracted with ethyl acetate. The organic layer was washed with water and brine solution, and dried over anhydrous sodium sulphate. The solvent was evaporated under reduced pressure to obtain a residue which was purified by column chromatography over silica gel using 30% ethyl acetate in hexane as eluant to afford the title compound (0.37 g).
Mass (m/z): 527.23 (M$^+$+1)

Step m: Synthesis of 2-(2-{(3aR,5S,6R,6aR)-5-[2-(3'-fluoro-4'-methylbiphenyl-4-yl)ethyl]-2,2-dimethyltetrahydrofuro[2,3-d][1,3]dioxol-6-yl}ethyl)-1H-isoindole-1,3(2H)-dione 10% Palladium on charcoal (100 g) was added to a solution of the compound obtained from step l above (0.37 g) in ethyl acetate (10 mL) at room temperature and the reaction mixture was hydrogenated at 35 psi for 1 hour in a Paar apparatus. The reaction mixture was filtered through a celite pad and the residue was washed with methanol. The filtrate was concentrated to afford the title compound (0.28 g).

Step n: Synthesis of 2-(2-{(2S,3S,4R,5S)-2-[2-(3'-fluoro-4'-methylbiphenyl-4-yl)ethyl]-4,5-dihydroxytetrahydrofuran-3-yl}ethyl)-1H-isoindole-1,3(2H)-dione To a solution of the compound obtained from step m above (0.28 g) in acetonitrile (20 mL) and water (2 mL), 30% perchloric acid (0.4 mL) was added at room temperature. The reaction mixture was heated to 55° C. for 30 minutes. The reaction mixture was then quenched using a sodium bicarbonate solution. The solvents were evaporated at reduced pressure. The residue thus obtained was taken in ethyl acetate and water. The organic layer was separated, washed with water and brine solution, and dried over anhydrous sodium sulphate. The solvent was concentrated under reduced pressure to yield the title compound (0.418 g) as crude mass which was used further without any purification and characterization.

Step o: Synthesis of (2R,3S)-2-[2-(1,3-dioxo-1,3-dihydro-2H-isoindol-2-yl)ethyl]-5-(3'-fluoro-4'-methylbiphenyl-4-yl)-3-(formyloxy)pentanoic acid A solution of sodium metaperiodate (0.489 g in 5 mL of water) was added to a solution of the compound, obtained from step n above (0.4 g), in a tert-butanol:tetrahydrofuran (5 mL:5 mL) at 0° C. The reaction mixture was stirred for 2 hours at the same temperature and potassium permanganate (0.033 g) was added at 0° C. After stirring the reaction mixture for an additional 6 hours at room temperature, the reaction mixture was evaporated on a rotary evaporator, and the residue was taken into water and extracted with ethyl acetate. The organic layer was washed with water and brine solution and dried over anhydrous sodium sulphate. The solvent was evaporated under reduced pressure to afford the title compound (0.31 g) as crude mass which was used further without any purification and characterization.

Step p: Synthesis of (2R,3S)-2-[2-(1,3-dioxo-1,3-dihydro-2H-isoindol-2-yl)ethyl]-5-(3'-fluoro-4'-methylbiphenyl-4-yl)-3-hydroxypentanoic acid To a solution of the compound obtained from step o above (0.31 g) in methanol (5 mL), potassium carbonate (0.094 g) was added at 0° C. The reaction mixture was stirred at room temperature for 3 hours. The reaction mixture was diluted with ethyl acetate (50 mL), acidified with sodium hydrogen sulphate, and washed with water (20 mL). The organic layer was dried over anhydrous sodium sulphate and concentrated under reduced pressure to obtain a residue which was purified by preparative thin layer chromatography using 10% methanol in dichloromethane as eluant to afford the title compound (0.020 g).

Mass (m/z): 476.07 (M$^+$+1)

$^1$HNMR (CD$_3$OD): δ 7.72-7.64 (m, 4H), 7.36-7.34 (m, 2H), 7.18-7.10 (m, 5H), 3.68-3.61 (m, 3H), 2.75-2.71 (m, 1H), 2.55-2.49 (s, 1H), 2.32-2.30 (m, 1H), 2.16 (s, 3H), 1.99-1.94 (m, 2H), 1.70-1.62 (m, 2H).

Example 6

Synthesis of (2S,3S)-3-hydroxy-5-(4'-methoxybiphenyl-4-yl)-2-[2-(4-oxo-1,2,3-benzotriazin-3(4H)-yl)ethyl]pentanoic acid (Compound No. 208)

Step a: Synthesis of 5-O-[tert-butyl(diphenyl)silyl]-3-deoxy-1,2-O-isopropylidene-3-[2-(4-oxo-1,2,3-benzotriazin-3(4H)-yl)ethyl]-α-L-ribofuranose A mixture of the compound obtained from step f of Example 1 (20 g), triphenyl phosphine (17.6 g), and 1,2,3-benzotriazin-4(3H)-one (7.2 g) was dried in high vacuum in a round bottom flask for 10 minutes. The vacuum was released under a nitrogen atmosphere and tetrahydrofuran (200 mL) was added to the above reaction mixture. The reaction mixture was cooled to 0° C. and diisopropyl azodicarboxylate (9.8 mL) was added slowly. The reaction mixture was stirred for 30 minutes at the same temperature, and then quenched with water and extracted with ethyl acetate. The organic layer was washed with water and brine solution, and dried over anhydrous sodium sulphate, and concentrated to obtain a residue which was purified by column chromatography over silica gel using 30% ethyl acetate in hexane as eluant to afford the title compound (22 g).

Mass (m/z): 586.24 (M$^+$+1).

Step b: Synthesis of 3-deoxy-1,2-O-isopropylidene-3-[2-(4-oxo-1,2,3-benzotriazin-3(4H)-yl)ethyl]-α-L-ribofuranose To a solution of the compound obtained from step a above (22 g) in dry tetrahydrofuran (200 mL) at 0° C., 1 M solution of tetra-butylammonium fluoride (75 mL) was added. The resulting mixture was stirred at 0° C. for 1 hour and then at room temperature for 4 hours. The reaction mixture was cooled to 0° C., quenched with saturated ammonium chloride and extracted with ethyl acetate. The organic layer was washed with water and brine, dried over anhydrous sodium sulphate, and concentrated. The residue thus obtained was purified by column chromatography over silica gel using 50% ethyl acetate in hexane as eluant to furnish the title compound (6.5 g).

Mass (m/z): 348.25 (M$^+$+1)

Step c: Synthesis of (5S)-3-deoxy-4,5-O-isopropylidene-3-[2-(4-oxo-1,2,3-benzotriazin-3(4H)-yl)ethyl]-D-ribo-pentodialdo-5,2-furanose To a solution of the compound obtained from step b above (6.5 g) in dry dichloromethane (100 mL) cooled to 0° C., Dess-Martin periodinane reagent (11.1 g) was added. The reaction mixture was allowed to stir for 2 hours. The reaction mixture was quenched with sodium thiosulphate and sodium hydrogen carbonate. Dichloromethane was added to the reaction mixture. The organic layer was separated, washed with water and brine solution, dried over sodium sulphate, and evaporated to afford the title compound. (6.5 g)

Step d: Synthesis of 3-(2-{(3aS,5S,6S,6aS)-5-[(E)-2-(4-bromophenyl)vinyl]-2,2-dimethyltetrahydrofuro[2,3-d][1,3]dioxol-6-yl}ethyl)-1,2,3-benzotriazin-4(3H)-one To a suspension of sodium hydride (0.979 g, 60% in oil) in dimethyl sulphoxide (60 mL) cooled to 0° C., (4-bromobenzyl)triphenylphosphonium bromide (14.5 g) was added. The compound obtained from step c above (6.5 g) in tetrahydrofuran (60 mL) was added drop-wise after 20 minutes, and the reaction mixture was stirred for 1 hour at the same temperature. The reaction mixture was quenched with water and extracted with ethyl acetate. The organic layer was washed with water and brine solution, and dried over anhydrous sodium sulphate. The solvent was evaporated under reduced pressure and the residue thus obtained was purified by column chromatography using 40% ethyl acetate in hexane as eluant to furnish the title compound (4 g).

Mass (m/z): 498.19 (M$^+$+1)

Step e: Synthesis of 3-(2-{(3aS,5S,6S,6aS)-5-[(E)-2-(4'-methoxybiphenyl-4-yl)vinyl]-2,2-dimethyltetrahydrofuro[2,3-d][1,3]dioxol-6-yl}ethyl)-1,2,3-benzotriazin-4(3H)-one A mixture of the compound obtained from step d above (1 g), 4-methoxyphenyl boronic acid (0.61 g), tetrakistriphenylphosphine palladium (0) (0.232 g), and potassium carbonate (0.832 g) was dried under high vacuum for 10 minutes and dry dimethylformamide (20 mL) was added at room temperature. The reaction mixture was heated at 120° C. for 2 hours, and then quenched with water and extracted with ethyl acetate. The organic layer was washed with water and brine solution, and dried over anhydrous sodium sulphate. The solvent was evaporated under reduced pressure to obtain a residue which was purified by column chromatography over silica gel using 50% ethyl acetate in hexane as eluant to afford the title compound (0.62 g).

Mass (m/z): 526.41 (M$^+$+1)

Step f: Synthesis of 3-(2-{(3aS,5S,6S,6aS)-5-[2-(4'-methoxybiphenyl-4-yl)ethyl]-2,2-dimethyltetrahydrofuro[2,3-d][1,3]dioxol-6-yl}ethyl)-1,2,3-benzotriazin-4(3H)-one To a solution of the compound obtained from step e above (0.62 g) in a solvent mixture of ethyl acetate (20 mL), 10% palladium on charcoal (0.3 g) was added at room temperature, and the reaction mixture was hydrogenated at 35 psi for 4 hours in a Paar apparatus. The reaction mixture was filtered through a celite pad and the residue was washed with methanol. The filtrate was concentrated to afford the title compound (0.6 g).

Step g: Synthesis of 3-(2-{(2S,3R,4S,5R)-4,5-dihydroxy-2-[2-(4'-methoxybiphenyl-4-yl)ethyl]tetrahydrofuran-3-yl}ethyl)-1,2,3-benzotriazin-4(3H)-one Perchloric acid (0.2 mL) was added to a solution of the compound obtained from step f above (0.6 g) in acetonitrile (50 mL) and water (10 mL) at room temperature. The reaction mixture was heated to 55° C. for 30 minutes. The reaction mixture was then quenched using a sodium hydrogen carbonate solution. The solvents were evaporated at reduced pressure. The residue thus obtained was taken in ethyl acetate and water. The organic layer was separated, washed with water and brine solution, and dried over anhydrous sodium sulphate. The solvent was concentrated under reduced pressure to yield the title compound (0.6 g).

Step h: Synthesis of (2S,3S)-3-(formyloxy)-2-[2-(4-oxo-1,2,3-benzotriazin-3(4H)-yl)ethyl]-5-(4-pyrimidin-5-ylphenyl)pentanoic acid To a solution of the compound obtained from step g above (0.6 g) in a tert-butanol:tetrahydrofuran (7 mL:7 mL), a solution of sodium metaperiodate (0.973 g in 7 mL of water) was added at 0° C. The reaction mixture was stirred for 2 hours at the same temperature and potassium permanganate (0.036 g) was added at 0° C. After stirring the reaction mixture for an additional 6 hours at room temperature, the reaction mixture was evaporated and the residue was taken into water and extracted with ethyl acetate. The organic layer was washed with water and brine solution and dried over anhydrous sodium sulphate. The solvent was evaporated under reduced pressure to afford the title compound (0.5 g).

Step i: Synthesis of (2S,3S)-3-hydroxy-5-(4'-methoxybiphenyl-4-yl)-2-[2-(4-oxo-1,2,3-benzotriazin-3(4H)-yl)ethyl]pentanoic acid Potassium carbonate (0.151 g) was added to a solution of the compound obtained from step h above (0.5 g) in methanol (5 mL) and tetrahydrofuran (5 mL) at 0° C. The reaction mixture was stirred at room temperature for 3 hours. The solvents were evaporated and the residue was taken into water and ethyl acetate. The organic layer was washed with water and brine solution, and dried over anhydrous sodium sulphate. The solvent was evaporated under reduced pressure to obtain a residue which was purified by preparative thin layer chromatography using 10% methanol in dichloromethane as eluent to afford the title compound (0.008 g).

Mass (m/z): 474.31 (M$^+$+1);
$^1$HNMR (CD$_3$OD): δ 8.32-7.87 (m, 5H), 7.50-7.42 (m, 4H), 7.24-7.20 (m, 2H), 6.97-6.94 (m, 1H), 4.60-4.50 (m, 2H), 3.81 (s, 3H), 3.59 (br t, 1H), 3.0-1.8 (m, 7H).

Example 7

Synthesis of (2S,3R)-3-hydroxy-5-[4-(5-methylpyridin-2-yl)phenyl]-2-[2-(4-oxo-1,2,3-benzotriazin-3(4H)-yl)ethyl]pentanoic acid (Compound No. 209)

Step a: Synthesis of 4-(5-methylpyridin-2-yl)benzaldehyde

A mixture of 2-bromo-5-methylpyridine (2 g), (4-formylphenyl)boronic acid (3.5 g), tetrakis(triphenylphosphine)palladium(0) (0.672 g), and potassium carbonate (4.8 g) was dried under high vacuum for 10 minutes and dry dimethylformamide (15 mL) was added at room temperature. The reaction mixture was heated at 110° C. for 6 hours, and then quenched with water and extracted with ethyl acetate. The organic layer was washed with water and brine solution, and dried over anhydrous sodium sulphate. The solvent was evaporated under reduced pressure to obtain a residue which was purified by column chromatography over silica gel using 20% ethyl acetate in hexane as eluant to afford the title compound (2.8 g).

Mass (m/z): 198.20

Step b: Synthesis of ethyl (2E)-3-[4-(5-methylpyridin-2-yl)phenyl]prop-2-enoate To a suspension of sodium hydride (0.682 g, 60% in oil.) in tetrahydrofuran (20 mL), triethyl phosphonoacetate (3.82 g) was charged at 0° C. After 15 minutes, a solution of the compound obtained from step a above (2.8 g) in tetrahydrofuran (5 mL) was added drop-wise, and the reaction mixture was stirred for 30 minutes at room temperature. A saturated solution of ammonium chloride in water was added to the reaction mixture. The solvent was evaporated and the resulting mixture was extracted with ethyl acetate. The combined extracts were dried over anhydrous sodium sulphate and evaporated under reduced pressure to yield a residue which was purified by column chromatography over silica gel using 15% ethyl acetate in hexane as eluant to afford the title compound (1.8 g).

Step c: Synthesis of ethyl 3-[4-(5-methylpyridin-2-yl)phenyl]propanoate

10% Palladium on charcoal (0.8 g) was added to a solution of the compound obtained from step b above (1.8 g) in tetrahydrofuran (15 mL) at room temperature, and hydrogen was supplied at 50 psi in a Paar apparatus for 4 hours. The reaction mixture was filtered through a celite pad and concentrated to afford the title compound (1.8 g).

Step d: Synthesis of 3-[4-(5-methylpyridin-2-yl)phenyl]propan-1-ol

To a suspension of lithium aluminum hydride (0.424 g) in tetrahydrofuran (20 mL), a solution of the compound obtained from step c above (2 g) in tetrahydrofuran (10 mL) was added at −20° C. The reaction mixture was stirred for 2 hours at 30° C. and a saturated solution of sodium sulphate was added at the same temperature. The reaction mixture was then filtered through a celite pad and the residue was washed with ethyl acetate. The organic layer was dried over anhydrous sodium sulphate, filtered, and concentrated under reduced pressure. The residue thus obtained was purified by column chromatography over silica gel using 50% ethyl acetate in hexane as eluant to afford the title compound (1.2 g).

Step e: Synthesis of 3-[4-(5-methylpyridin-2-yl)phenyl]propanal

To a stirred solution of the compound obtained from step d above (1.4 g) in dichloromethane (20 mL), 2,2,6,6-tetramethylpiperidine N-oxyl (9.6 mg) and potassium bromide (73.4 mg) were added at 0° C. under nitrogen atmosphere. Sodium hypochlorite (13.7 mL, 4% solution) was added at pH 8-9 (maintained by adding aqueous sodium bicarbonate solution). The reaction was stirred for 20 minutes at 0° C. The organic layer was separated and the aqueous layer was extracted with dichloromethane. The combined organic layers were washed with saturated aqueous sodium bicarbonate solution, water, and brine. The organic layer was dried over anhydrous sodium sulphate, filtered, and concentrated under reduced pressure to afford the title compound (0.9 g).

Step f: Synthesis of 3-{(3S,4R)-3-{[(4S)-4-benzyl-2-oxo-1,3-thiazolidin-3-yl]carbonyl}-4-hydroxy-6-[4-(5-methylpyridin-2-yl)phenyl]hexyl}-1,2,3-benzotriazin-4(3H)-one In a flame-dried flask, 3-{4-[(4S)-4-benzyl-2-oxo-1,3-thiazolidin-3-yl]-4-oxobutyl}-1,2,3-benzotriazin-4(3H)-one (1.18 g) was taken up in dichloromethane (10 mL) and cooled to 0° C. Titanium tetrachloride (3.4 mL) in dichloromethane (6 mL) was added drop-wise and the reaction mixture was stirred for 10 to 15 minutes. (−)-Sparteine (1.7 g) was added slowly to the reaction mixture and stirred at 0° C. for 45 minutes. A solution of the compound obtained from step e above (0.65 g) in dichloromethane (10 mL) was added slowly and stirring was continued at 0° C. After 3 hours, the reaction was quenched with the drop-wise addition of a saturated ammonium chloride solution, and dichloromethane was added. The organic layer was separated and the aqueous layer was extracted with dichloromethane. The organic layer was washed with brine, dried over anhydrous sodium sulphate, and concentrated under reduced pressure. The crude product thus obtained was purified by silica gel flash column chromatography using 30% ethyl acetate in hexane as eluant to afford the aldol adduct (0.56 g).

Step g: Synthesis of (2S,3R)-3-hydroxy-5-[4-(5-methylpyridin-2-yl)phenyl]-2-[2-(4-oxo-1,2,3-benzotriazin-3(4H)-yl)ethyl]pentanoic acid To a stirred solution of the compound obtained from step f above (0.2 g) in tetrahydrofuran:water (3:1, 10 mL), aqueous hydrogen peroxide solution (30%, 0.16 mL) was added at 0° C. followed by the addition of lithium hydroxide monohydrate (0.02 g) in water (5 mL). The reaction mixture was stirred at 0° C. for 30 minutes. The reaction mixture was concentrated, and the residue was extracted with ethyl acetate. The aqueous layer was acidified with sodium hydrogen sulphate and extracted with ethyl acetate. The combined layers were washed with water and brine, and dried over anhydrous sodium sulphate. The solvents were evaporated under reduced pressure and the crude residue was purified by silica gel flash column chromatography using 3% methanol in dichloromethane as eluant to afford the title compound (0.035 g).

Mass (m/z): 459.21 (M$^+$+1);
$^1$HNMR (CD$_3$OD): δ 8.40 (s, 1H), 8.30 (d, 1H, J=7.88 Hz), 8.15 (d, 1H, J=8 Hz), 8.05-7.70 (m, 6H), 7.27 (d, 2H, J=7.6 Hz), 4.40-4.0 (m, 2H), 3.80-3.60 (m, 1H), 2.80-2.40 (m, 5H), 2.38 (s, 3H), 1.80-1.60 (m, 2H).

Example 7A

Synthesis of (2S,3R)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 86)

Step a: Synthesis of methyl (2E)-3-(4-bromophenyl)prop-2-enoate

To a stirred solution of 4-bromocinnamic acid (16 g) in methanol (150 mL), thionyl chloride (30 mL) was added at 0° C. The reaction mixture was warmed to room temperature and refluxed for 3 hours. After cooling to room temperature, the solvents were evaporated to dryness. The crude compound obtained was used as such for the next step.

Step b: Synthesis of methyl (2E)-3-[4-(6-methoxypyridin-3-yl)phenyl]prop-2-enoate The compound obtained from step a above (7.5 g), pyridine-2-methoxy-5-boronic acid (9.48 g), tetrakis(triphenylphosphine)palladium(0) (1.79 g), and potassium carbonate (12.83 g) were taken in dimethylformamide (60 mL) under nitrogen atmosphere. The reaction mixture was refluxed under nitrogen atmosphere for 6 hours. After cooling to room temperature, water was added and the reaction mixture was extracted with ethyl acetate. The combined organic layers were washed with water and brine, dried over anhydrous sodium sulfate, and the solvents were evaporated under reduced pressure. The crude product was purified by silica gel flash column chromatography using 20% to 30% ethyl acetate in hexane to get the title compound (8.09 g).

Step c: Synthesis of methyl 3-[4-(6-methoxypyridin-3-yl)phenyl]propanoate

To a solution of compound obtained from step b above (8.1 g) in a mixture of ethyl acetate/methanol/tetrahydrofuran (~300 mL), 10% Palladium on charcoal (1.6 g) was added and stirred under hydrogen atmosphere at 30 psi in a Paar apparatus for 2.5 hours. The reaction mixture was filtered through a celite pad, washed with ethyl acetate, and the filtrate was concentrated under reduced pressure to obtain the title compound as a white solid which was used as such for the next step.

Step d: Synthesis of 3-[4-(6-methoxypyridin-3-yl)phenyl]propanoic acid

To a stirred solution of lithium aluminum hydride (2.28 g) in tetrahydrofuran (120 mL), the compound obtained from step c above (8 g) in tetrahydrofuran (50 mL) was added at 0° C. The reaction mixture was stirred at 0° C. for 3 hours. The reaction mixture was quenched carefully with saturated ammonium chloride solution, filtered through celite, and washed with ethyl acetate. The organic layers were separated, washed with brine, and dried over anhydrous sodium sulfate, and solvents were evaporated under reduced pressure. The crude product was purified by silica gel flash column chromatography using 20% to 30% ethyl acetate in hexane to get the title compound as a white crystalline solid (5.1 g).

Step e: Synthesis of 3-[4-(6-methoxypyridin-3-yl)phenyl]propanal

To a stirred solution of the compound obtained from step d above (9.0 g) in dichloromethane (90 ml), 2,2,6,6-tetramethylpiperidine N-oxyl (58.77 mg) and potassium bromide (447.57 mg) were added at 0° C. under nitrogen atmosphere. A 4% aqueous sodium hypochlorite (3.497 g) was added at pH 8-9 (maintained by adding saturated aqueous sodium bicarbonate solution). The reaction was stirred for 20 minutes at 0° C. Then, the organic layer was separated and the aqueous layer was extracted with dichloromethane. The combined organic layers were washed with saturated aqueous sodium bicarbonate solution, water, and brine. Finally, the organic layers were dried over anhydrous sodium sulfate and concentrated under reduced pressure to afford the title compound (8.1 g) which was used as such in the next step.

Step f: Synthesis of 3-{(3S,4S)-3-{[(4S)-4-benzyl-2-oxo-1,3-thiazolidin-3-yl]carbonyl}-4-hydroxy-6-[4-(5-methoxypyridin-2-yl)phenyl]hexyl}-1,2,3-benzotriazin-4(3H)-one In a flame-dried flask, 3-{4-[(4S)-4-benzyl-2-oxo-1,3-thiazolidin-3-yl]-4-oxobutyl}-1,2,3-benzotriazin-4(3H)-one (2.0 g) was taken up in dichloromethane (10 mL) and cooled to 0° C. Titanium tetrachloride (0.619 mL) in dichloromethane (6 mL) was added drop-wise and the reaction mixture was stirred for 10-15 minutes. (−)-Sparteine (2.7 mL) was added slowly to the reaction mixture and stirred at 0° C. for 45 minutes. A solution of the compound obtained from step e above (1.34 g) in dichloromethane (10 mL) was added slowly and stirring was continued at 0° C. After 3 hours, the reaction was quenched with the drop-wise addition of saturated ammonium chloride solution, and dichloromethane was added. The organic layer was separated and the aqueous layer was extracted with dichloromethane. The organic layer was washed with brine, dried over anhydrous sodium sulphate, and concentrated under reduced pressure. The crude product thus obtained was purified by silica gel flash column chromatography using 30% ethyl acetate in hexane as eluent to afford the aldol adduct (1.21 g).

Step g: Synthesis of (2S,3R)-3-hydroxy-5-[4-(5-methoxypyridin-2-yl)phenyl]-2-[2-(4-oxo-1,2,3-benzotriazin-3(4H)-yl)ethyl]pentanoic acid To a stirred solution of the compound obtained from step f above (1.21 g) in tetrahydrofuran:water (3:1, 15 mL), aqueous hydrogen peroxide solution (30%, 1.02 mL) was added at 0° C., followed by addition of lithium hydroxide monohydrate (114.5 mg) in water (5 mL). The reaction mixture was stirred at 0° C. until the completion of the hydrolysis. The reaction mixture was concentrated and the residue was extracted with ethyl acetate. The aqueous layer was acidified with sodium hydrogen sulphate and extracted with ethyl acetate. The combined layers were washed with water and brine, and dried over anhydrous sodium sulphate. The solvents were evaporated under reduced pressure and the crude residue was purified by silica gel flash column chromatography using 3% methanol in dichloromethane as eluant to afford the title compound (0.61 g).

Mass (m/z): 474.87 (M$^+$+1);
$^1$H NMR (400 MHz, MeOD): δ 8.32-8.30 (2H, m), 8.16-8.14 (1H, m), 8.04-8.03 (1H, m), 7.92-7.88 (2H, m), 7.46 (2H, d, J=8 Hz), 7.24 (2H, m, J=8 Hz), 6.86 (1H, d, J=8 Hz), 4.57-4.53 (2H, m), 3.93 (3H, s), 3.78-3.83 (1H, m), 2.83-2.80 (1H, m), 2.63-2.60 (1H, m), 2.52-2.49 (1H, m), 2.32-2.28 (2H, m), 1.80-1.76 (2H, m).

Example 7B

Synthesis of (2S,3R)-5-(2',4'-difluorobiphenyl-4-yl)-3-hydroxy-2-[(4-oxo-1,2,3-benzotriazin-3(4H)-yl)methyl]pentanoic acid (Compound No. 216)

Step a: Synthesis of methyl (2E)-3-(4-bromophenyl)prop-2-enoate

To a stirred solution of 4-bromocinnamic acid (16 g) in methanol (150 mL), thionyl chloride (30 mL) was added at 0° C. The reaction mixture was warmed to room temperature and refluxed for 3 hours. After cooling to room temperature, the solvents were evaporated to dryness. The crude compound obtained was used as such for the next step.

Step b: Synthesis of methyl (2E)-3-(3',5'-difluorobiphenyl-4-yl)prop-2-enoate

The compound obtained from step a above (0.75 g), 2,4-difluorophenyl boronic acid (0.737 g), tetrakis(triphenylphosphine)palladium(0) (0.07 g), and potassium carbonate (1.28 g) were taken in dimethylformamide (6 mL) under nitrogen atmosphere. The reaction mixture was refluxed under nitrogen atmosphere for 6 hours. After cooling to room temperature, water was added and the reaction mixture was extracted with ethyl acetate. The combined organic layers were washed with water and brine, dried over anhydrous sodium sulfate, and the solvents were evaporated under reduced pressure. The crude product was purified by silica gel flash column chromatography using 20% to 30% ethyl acetate in hexane to get the title compound (0.810 g).

Step c: Synthesis of methyl 3-(3',5'-difluorobiphenyl-4-yl)propanoate

To a solution of the compound obtained from step b above (0.79 g) in a mixture of ethyl acetate (~10 mL), 10% Palladium on charcoal (0.2 g) was added and stirred under hydrogen atmosphere at 30 psi for 2.5 hours. The reaction mixture was filtered through a celite pad washed with ethyl acetate and the filtrate was concentrated under reduced pressure to obtain the title compound (0.77 g) as white solid which was used as such for the next step.

Step d: Synthesis of 3-(3',5'-difluorobiphenyl-4-yl)propanoic acid

To a stirred solution of lithium aluminum hydride (0.2 g) in tetrahydrofuran (15 mL), the compound obtained from step c above (0.77 g) in tetrahydrofuran (50 mL) was added at 0° C. The reaction mixture was stirred at 0° C. for 3 hours. The reaction mixture was quenched carefully with saturated ammonium chloride solution, filtered through a celite pad, and washed with ethyl acetate. The organic layers were separated, washed with brine, and dried over anhydrous sodium sulfate, and solvents were evaporated under reduced pressure.

The crude product was purified by silica gel flash column chromatography using 20% to 30% ethyl acetate in hexane to get the title compound as a white crystalline solid (0.70 g).

Step e: Synthesis of 3-(3',5'-difluorobiphenyl-4-yl) propanal

To a stirred solution of the compound obtained from step d above (0.7 g) in dichloromethane (10 mL), 2,2,6,6-tetramethylpiperidine N-oxyl (4.36 mg) and potassium bromide (33.32 mg) were added at 0° C. under nitrogen atmosphere. Sodium hypochlorite (6.5 mL, 4% solution) was added at pH 8-9 (maintained by adding aqueous sodium bicarbonate solution). The reaction was stirred for 20 minutes at 0° C. The organic layer was separated and the aqueous layer was extracted with dichloromethane. The combined organic layers were washed with saturated aqueous sodium bicarbonate solution, water, and brine. The organic layer was dried over anhydrous sodium sulphate, filtered, and concentrated under reduced pressure to afford the title compound (0.57 g).

Step f: Synthesis of 3-[(2R,3S)-2-{[(4S)-4-benzyl-2-oxo-1,3-thiazolidin-3-yl]carbonyl}-5-(3',5'-difluorobiphenyl-4-yl)-3-hydroxypentyl]-1,2,3-benzotriazin-4(3H)-one In a flame-dried flask, 3-{3-[(4S)-4-benzyl-2-oxo-1,3-thiazolidin-3-yl]-3-oxopropyl}-1,2,3-benzotriazin-4(3H)-one (0.25 g) was taken up in dichloromethane (10 mL) and cooled to 0° C. Titanium tetrachloride (0.76 mL, 1 M solution) was added drop-wise and the reaction mixture was stirred for 10 to 15 minutes. (−)-Sparteine (0.36 mL) was added slowly to the reaction mixture and stirred at 0° C. for 20 minutes. A solution of the compound obtained from step e above (0.187 g) in dichloromethane (10 mL) was added slowly and stirring was continued at 0° C. After 3 hours, the reaction was quenched with the drop-wise addition of saturated ammonium chloride solution, and dichloromethane was added. The organic layer was separated and the aqueous layer was extracted with dichloromethane. The organic layer was washed with brine, dried over anhydrous sodium sulphate, and concentrated under reduced pressure. The crude product thus obtained was purified by silica gel flash column chromatography using 30% ethyl acetate in hexane as eluant to afford the title compound (0.24 g).

Step g: Synthesis of (2S,3R)-5-(3',5'-difluorobiphenyl-4-yl)-3-hydroxy-2-[(4-oxo-1,2,3-benzotriazin-3(4H)-yl)methyl]pentanoic acid To a stirred solution of the compound obtained from step f above (0.2 g) in tetrahydrofuran:water (3:1, 10 mL) aqueous hydrogen peroxide solution (30%, 0.16 mL) was added at 0° C., followed by the addition of lithium hydroxide monohydrate (19.53 mg) in water (2 mL). The reaction mixture was stirred at 0° C. until the completion of the hydrolysis. The reaction mixture was concentrated and the residue was extracted with ethyl acetate. The aqueous layer was acidified with sodium hydrogen sulphate and extracted with ethyl acetate. The combined layers were washed with water and brine and dried over anhydrous sodium sulphate. The solvents were evaporated under reduced pressure, and the crude residue was purified by silica gel flash column chromatography using 10% methanol in dichloromethane as eluant to afford the title compound (0.090 g).

Mass (m/z): 466.06 (M$^+$+1);

$^1$HNMR (CD$_3$OD): δ 8.17-8.8.15 (m, 1H), 8.05-8.01 (m, 1H), 7.90-7.88 (m, 1H), 7.86-7.84 (m, 1H), 7.46-7.42 (m, 2H), 7.40-7.29 (m, 2H), 7.03-6.98 (m, 2H), 4.82-4.84 (m, 2H), 3.94 (s, 1H), 3.22-3.21 (m, 1H), 2.91-2.89 (m, 1H), 2.78-2.75 (m, 1H), 1.94-1.90 (m, 2H).

Example 7C

Synthesis of (2S,3R)-5-(4'-fluorobiphenyl-4-yl)-3-hydroxy-2-[(4-oxo-1,2,3-benzotriazin-3(4H)-yl)methyl]pentanoic acid (Compound No. 217)

Step a: Synthesis of methyl (2E)-3-(4-bromophenyl)prop-2-enoate

To a stirred solution of 4-bromocinnamic acid (16 g) in methanol (150 mL), thionyl chloride (30 mL) was added at 0° C. The reaction mixture was warmed to room temperature and refluxed for 3 hours. After cooling to room temperature, the solvents were evaporated to dryness. The crude compound obtained was used as such for the next step.

Step b: Synthesis of methyl (2E)-3-(4'-fluorobiphenyl-4-yl)prop-2-enoate

The compound obtained from step a above (0.75 g), 4-fluorophenyl boronic acid (0.65 g), tetrakis(triphenylphosphine) palladium(0) (0.07 g), and potassium carbonate (1.28 g) were taken in dimethylformamide (6 mL) under nitrogen atmosphere. The reaction mixture was refluxed under nitrogen atmosphere for 6 hours. After cooling to room temperature, water was added and the reaction mixture was extracted with ethyl acetate. The combined organic layers were washed with water and brine and dried over anhydrous sodium sulfate, and the solvents were evaporated under reduced pressure. The crude product was purified by silica gel flash column chromatography using 20% to 30% ethyl acetate in hexane to get the title compound (0.720 g).

Step c: Synthesis of methyl 3-(4'-fluorobiphenyl-4-yl) propanoate

To a solution of the compound obtained from step b above (0.7 g) in a mixture of ethyl acetate (~20 mL), 10% palladium on charcoal (0.2 g) was added and stirred under hydrogen atmosphere at 30 psi in a Paar apparatus for 2.5 hours. The reaction mixture was filtered through a celite pad, washed with ethyl acetate, and the filtrate was concentrated under reduced pressure to obtain the title compound (0.7 g) as a white solid which was used as such for the next step.

Step d: Synthesis of 3-(4'-fluorobiphenyl-4-yl)propanoic acid

To a stirred solution of lithium aluminium hydride (0.2 g) in tetrahydrofuran (15 mL), the compound obtained from step c above (0.7 g) in tetrahydrofuran (50 mL) was added at 0° C. The reaction mixture was stirred at 0° C. for 3 hours. The reaction mixture was quenched carefully with saturated ammonium chloride solution, filtered through a celite pad, and washed with ethyl acetate. The organic layers were separated, washed with brine, and dried over anhydrous sodium sulfate, and solvents were evaporated under reduced pressure. The crude product was purified by silica gel flash column chromatography using 20% to 30% ethyl acetate in hexane to get the title compound as a white crystalline solid (0.70 g).

Step e: Synthesis of 3-(4'-fluorobiphenyl-4-yl)propanal

To a stirred solution of the compound obtained from step d above (0.7 g) in dichloromethane (10 mL), 2,2,6,6-tetramethylpiperidine N-oxyl (4.74 mg) and potassium bromide (36.05 mg) were added at 0° C. under nitrogen atmosphere. Sodium hypochlorite (0.28 g, 4% solution) was added at pH 8-9 (maintained by adding aqueous sodium bicarbonate solution). The reaction mixture was stirred for 20 minutes at 0° C. The organic layer was separated and the aqueous layer was extracted with dichloromethane. The combined organic layers were washed with saturated aqueous sodium bicarbonate solution, water, and brine. The organic layer was dried over anhydrous sodium sulphate, filtered, and concentrated under reduced pressure to afford the title compound (0.55 g).

Step f: Synthesis of 3-[(2R,3S)-2-{[(4S)-4-benzyl-2-oxo-1,3-thiazolidin-3-yl]carbonyl}-5-(4'-fluorobiphenyl-4-yl)-3-hydroxypentyl]-1,2,3-benzotriazin-4(3H)-one In a flame-dried flask, 3-{3-[(4S)-4-benzyl-2-oxo-1,3-thiazolidin-3-yl]-3-oxopropyl}-1,2,3-benzotriazin-4(3H)-one (0.25 g) was taken up in dichloromethane (10 mL) and cooled to 0° C. Titanium tetrachloride (0.76 mL, 1 M solution) was added drop-wise and the reaction mixture was stirred for 10 to 15 minutes. (−)-Sparteine (0.36 mL) was added slowly to the reaction mixture and stirred at 0° C. for 20 minutes. A solution of the compound obtained from step e above (0.17 g) in dichloromethane (10 mL) was added slowly, and stirring was continued at 0° C. After 3 hours, the reaction was quenched with the drop-wise addition of saturated ammonium chloride solution, and dichloromethane was added. The organic layer was separated and the aqueous layer was extracted with dichloromethane. The organic layer was washed with brine, dried over anhydrous sodium sulphate, and concentrated under reduced pressure. The crude product thus obtained was purified by silica gel flash column chromatography using 30% ethyl acetate in hexane as eluant to afford the title compound (0.2 g).

Step g: Synthesis of (2S,3R)-5-(4'-fluorobiphenyl-4-yl)-3-hydroxy-2-[(4-oxo-1,2,3-benzotriazin-3(4H)-yl)methyl]pentanoic acid To a stirred solution of the compound obtained from step f above (0.18 g) in tetrahydrofuran:water (3:1, 10 mL), aqueous hydrogen peroxide solution (30%, 0.15 mL) was added at 0° C., followed by the addition of lithium hydroxide monohydrate (17.6 mg) in water (2 mL). The reaction mixture was stirred at 0° C. until the completion of the hydrolysis. The reaction mixture was concentrated and the residue was extracted with ethyl acetate. The aqueous layer was acidified with sodium hydrogen sulphate and extracted with ethyl acetate. The combined layers were washed with water and brine, and dried over anhydrous sodium sulphate. The solvents were evaporated under reduced pressure and the crude residue was purified by silica gel flash column chromatography using 10% methanol in dichloromethane as eluant to afford the title compound (0.075 g).

Mass (m/z): 448.07 ($M^+$+1);

$^1$HNMR (CD$_3$OD): δ 8.25-8.8.30 (d, 1H, J=8 Hz), 8.15-8.12 (d, 1H, J=8 Hz), 8.05-8.00 (t, 1H, J=8 Hz), 7.89-7.85 (t, 1H, J=8 Hz), 7.58-7.55 (m, 1H), 7.47-7.45 (d, 1H, J=8 Hz), 7.28-7.26 (d, 1H, J=8 Hz), 7.89-7.87 (m, 1H), 7.61 (m, 2H), 7.53-7.59 (m, 1H), 7.30-7.25 (d, 2H J=8 Hz), 7.15-7.11 (t, 2H, J=8 Hz), 4.81-4.79 (m, 2H), 3.92 (s, 1H), 3.22-3.16 (m, 1H), 2.92-2.90 (m, 1H), 2.75-2.73 (m, 1H), 1.93-1.87 (m, 2H).

The following compounds were prepared employing procedures as provided in Examples 1 to 7C described above.

Compound Nos. 1 to 81, 86-88, 90-95, 97-119, 121-142, 144-203, 211-213, and 226-232 were prepared following Example 1; Compound Nos. 82-83 were prepared following Example 2; Compound Nos 84-85 and 204 were prepared following Example 3; Compound Nos. 89 and 96 were prepared following Example 4; Compound Nos. 120 and 205-207 were prepared following Example 5; Compound Nos. 143 and 208 were prepared following Example 6; and Compound Nos. 86, 209-210, and 214-225 were prepared following Example 7.

Specific compounds, suitable for use, prepared in the present invention, are listed below:

(2S,3R)-3-hydroxy-2-[2-(4-oxo-1,2,3-benzotriazin-3(4H)-yl)ethyl]-5-(4-pyrimidin-5-ylphenyl)pentanoic acid (Compound No. 1);
Mass (m/z): 446.0 ($M^+$+1).

(2S,3R)-2-[2-(5-tert-butyl-1,3-dioxo-1,3-dihydro-2H-isoindol-2-yl)ethyl]-3-hydroxy-5-[4-(6-methoxypyridin-3-yl)phenyl]pentanoic acid (Compound No. 2)
Mass (m/z): 531.09 ($M^+$+1);

(2S,3R)-2-[2-(1,3-dioxo-1,3-dihydro-2H-isoindol-2-yl)ethyl]-3-hydroxy-5-[4-(6-methylpyridin-3-yl)phenyl]pentanoic acid (Compound No. 3)
Mass (m/z): 458.82 ($M^+$+1);

(2S,3R)-2-[2-(1,3-dioxo-1,3-dihydro-2H-isoindol-2-yl)ethyl]-5-(4'-fluorobiphenyl-4-yl)-3-hydroxypentanoic acid (Compound No. 4);

(2S,3R)-5-(3',4'-difluorobiphenyl-4-yl)-2-[2-(1,3-dioxo-1,3-dihydro-2H-isoindol-2-yl)ethyl]-3-hydroxypentanoic acid (Compound No. 5)
Mass (m/z): 479.70 ($M^+$+1);

(2S,3R)-3-hydroxy-5-[4-(6-methylpyridin-3-yl)phenyl]-2-[2-(4-oxo-1,2,3-benzotriazin-3(4H)-yl)ethyl]pentanoic acid (Compound No. 6)
Mass (m/z): 458.94 ($M^+$+1);

(2S,3R)-3-hydroxy-2-[2-(5-methyl-1,3-dioxo-1,3-dihydro-2H-isoindol-2-yl)ethyl]-5-[4-(6-methylpyridin-3-yl)phenyl]pentanoic acid (Compound No. 7)
Mass (m/z): 472.87 ($M^+$+1);

(2S,3R)-5-(4'-fluorobiphenyl-4-yl)-3-hydroxy-2-[2-(5-methyl-1,3-dioxo-1,3-dihydro-2H-isoindol-2-yl)ethyl]pentanoic acid (Compound No. 8);

(2S,3R)-5-(4'-fluorobiphenyl-4-yl)-3-hydroxy-2-[2-(4-oxo-1,2,3-benzotriazin-3(4H)-yl)ethyl]pentanoic acid (Compound No. 9)
Mass (m/z): 461.87 ($M^+$+1);

(2S,3R)-3-hydroxy-5-(4'-methoxybiphenyl-4-yl)-2-[2-(4-oxo-1,2,3-benzotriazin-3(4H)-yl)ethyl]pentanoic acid (Compound No. 10)
Mass (m/z): 473.79 ($M^+$+1);

(2S,3R)-5-(3',4'-difluorobiphenyl-4-yl)-3-hydroxy-2-[2-(5-methyl-1,3-dioxo-1,3-dihydro-2H-isoindol-2-yl)ethyl]pentanoic acid (Compound No. 11)
Mass (m/z): 493.81 ($M^+$+1);

(2S,3R)-5-(3',4'-difluorobiphenyl-4-yl)-3-hydroxy-2-[2-(4-oxo-1,2,3-benzotriazin-3(4H)-yl)ethyl]pentanoic acid (Compound No. 12)
Mass (m/z): 479.77 ($M^+$+1);

(2S,3R)-2-[2-(1,3-dioxo-1,3-dihydro-2H-isoindol-2-yl)ethyl]-3-hydroxy-5-(4'-methoxybiphenyl-4-yl)pentanoic acid (Compound No. 13)
Mass (m/z): 473.86 ($M^+$+1);

(2S,3R)-2-[2-(1,3-dioxo-1,3-dihydro-2H-isoindol-2-yl)
ethyl]-3-hydroxy-5-[4'-(trifluoromethoxy)biphenyl-4-yl]
pentanoic acid (Compound No. 14)
Mass (m/z): 510.66 (M$^+$–18);

(2S,3R)-5-(4'-chloro-3'-fluorobiphenyl-4-yl)-3-hydroxy-2-
[2-(4-oxo-1,2,3-benzotriazin-3(4H)-yl)ethyl]pentanoic
acid (Compound No. 15)
Mass (m/z): 496.10 (M$^+$+1);

(2S,3R)-2-[2-(5-tert-butyl-1,3-dioxo-1,3-dihydro-2H-isoindol-2-yl)ethyl]-5-(3',4'-difluorobiphenyl-4-yl)-3-hydroxypentanoic acid (Compound No. 16)
Mass (m/z): 536.11 (M$^+$+1);

(2S,3R)-2-[2-(5-tert-butyl-1,3-dioxo-1,3-dihydro-2H-isoindol-2-yl)ethyl]-3-hydroxy-5-(4'-methoxybiphenyl-4-yl)
pentanoic acid (Compound No. 17)
Mass (m/z): 530.09 (M$^+$+1);

(2S,3R)-3-hydroxy-2-[2-(4-oxo-1,2,3-benzotriazin-3(4H)-yl)ethyl]-5-[4'-(trifluoromethyl)biphenyl-4-yl]pentanoic
acid (Compound No. 18)
Mass (m/z): 512.04 (M$^+$+1);

(2S,3R)-2-[2-(5-tert-butyl-1,3-dioxo-1,3-dihydro-2H-isoindol-2-yl)ethyl]-5-(4'-fluorobiphenyl-4-yl)-3-hydroxypentanoic acid (Compound No. 19)
Mass (m/z): 518.14 (M$^+$+1);

(2S,3R)-2-[2-(5-tert-butyl-1,3-dioxo-1,3-dihydro-2H-isoindol-2-yl)ethyl]-5-(4'-chlorobiphenyl-4-yl)-3-hydroxypentanoic acid (Compound No. 20)
Mass (m/z): 534.09 (M$^+$);

(2S,3R)-2-[2-(1,3-dioxo-1,3-dihydro-2H-isoindol-2-yl)
ethyl]-3-hydroxy-5-[4'-(trifluoromethyl)biphenyl-4-yl]
pentanoic acid (Compound No. 21)
Mass (m/z): 512.08 (M$^+$+1);

(2S,3R)-2-[2-(1,3-dioxo-1,3-dihydro-2H-isoindol-2-yl)
ethyl]-3-hydroxy-5-(4'-methylbiphenyl-4-yl)pentanoic
acid (Compound No. 22)
Mass (m/z): 458.14 (M$^+$+1);

(2S,3R)-2-[2-(1,3-dioxo-1,3-dihydro-2H-isoindol-2-yl)
ethyl]-5-(3'-fluoro-4'-methoxybiphenyl-4-yl)-3-hydroxypentanoic acid (Compound No. 23)
Mass (m/z): 492.07 (M$^+$+1).

(2S,3R)-3-hydroxy-5-[4-(6-methoxypyridin-3-yl)phenyl]-2-
[2-(5-methyl-1,3-dioxo-1,3-dihydro-2H-isoindol-2-yl)
ethyl]pentanoic acid (Compound No. 24)
Mass (m/z): 489.11 (M$^+$+1);

(2S,3R)-3-hydroxy-5-(4'-methylbiphenyl-4-yl)-2-[2-(4-oxo-1,2,3-benzotriazin-3(4H)-yl)ethyl]pentanoic acid (Compound No. 25)
Mass (m/z): 458.14 (M$^+$+1);

(2S,3R)-5-(4'-ethylbiphenyl-4-yl)-3-hydroxy-2-[2-(4-oxo-1,2,3-benzotriazin-3(4H)-yl)ethyl]pentanoic acid (Compound No. 26)
Mass (m/z): 472.15 (M$^+$+1);

(2S,3R)-5-(4'-chlorobiphenyl-4-yl)-3-hydroxy-2-[2-(5-methyl-1,3-dioxo-1,3-dihydro-2H-isoindol-2-yl)ethyl]pentanoic acid (Compound No. 27)
Mass (m/z): 492.08 (M$^+$+1);

(2S,3R)-5-(4'-chlorobiphenyl-4-yl)-3-hydroxy-2-[2-(4-oxo-1,2,3-benzotriazin-3(4H)-yl)ethyl]pentanoic acid (Compound No. 28)
Mass (m/z): 478.09 (M$^+$+1);

(2S,3R)-2-[2-(1,3-dioxo-1,3-dihydro-2H-isoindol-2-yl)
ethyl]-3-hydroxy-5-(4-pyrimidin-5-ylphenyl)pentanoic
acid (Compound No. 29)
Mass (m/z): 446.12 (M$^+$+1);

(2S,3R)-2-[2-(1,3-dioxo-1,3-dihydro-2H-isoindol-2-yl)
ethyl]-3-hydroxy-5-[4-(1-methyl-1H-pyrazol-4-yl)phenyl]pentanoic acid (Compound No. 30)
Mass (m/z): 448.25 (M$^+$+1);

(2S,3R)-2-[2-(1,3-dioxo-1,3-dihydro-2H-isoindol-2-yl)
ethyl]-3-hydroxy-5-(4-pyridin-3-ylphenyl)pentanoic acid
(Compound No. 31)
Mass (m/z): 445.23 (M$^+$+1);

(2S,3R)-5-[4-(2,3-dihydro-1,4-benzodioxin-6-yl)phenyl]-3-
hydroxy-2-[2-(4-oxo-1,2,3-benzotriazin-3(4H)-yl)ethyl]
pentanoic acid (Compound No. 32)
Mass (m/z): 502.19 (M$^+$+1);

(2S,3R)-3-hydroxy-5-[4-(6-methoxypyridin-3-yl)phenyl]-2-
[2-(8-methyl-4-oxo-1,2,3-benzotriazin-3(4H)-yl)ethyl]
pentanoic acid (Compound No. 33)
Mass (m/z): 489.0 (M$^+$+1);

(2S,3R)-3-hydroxy-2-[2-(8-methyl-4-oxo-1,2,3-benzotriazin-3(4H)-yl)ethyl]-5-[4-(6-methylpyridin-3-yl)phenyl]
pentanoic acid (Compound No. 34)
Mass (m/z): 473.0 (M$^+$+1);

(2S,3R)-3-hydroxy-5-[4-(1-methyl-1H-pyrazol-4-yl)phenyl]-2-[2-(4-oxo-1,2,3-benzotriazin-3(4H)-yl)ethyl]pentanoic acid (Compound No. 35)
Mass (m/z): 448.0 (M$^+$+1);

(2S,3R)-3-hydroxy-2-[2-(8-methoxy-4-oxo-1,2,3-benzotriazin-3(4H)-yl)ethyl]-5-[4-(6-methoxypyridin-3-yl)phenyl]pentanoic acid (Compound No. 36)
Mass (m/z): 505.0 (M$^+$+1);

(2S,3R)-2-[2-(7-chloro-4-oxo-1,2,3-benzotriazin-3(4H)-yl)
ethyl]-3-hydroxy-5-[4-(6-methoxypyridin-3-yl)phenyl]
pentanoic acid (Compound No. 37)
Mass (m/z): 509.0 (M$^+$+1);

(2S,3R)-3-hydroxy-2-{2-[7-(6-methoxypyridin-3-yl)-4-
oxo-1,2,3-benzotriazin-3(4H)-yl]ethyl}-5-[4-(6-methoxypyridin-3-yl)phenyl]pentanoic acid (Compound No. 38)
Mass (m/z): 582.0 (M$^+$+1);

(2S,3R)-2-[2-(6,7-difluoro-4-oxo-1,2,3-benzotriazin-3(4H)-yl)ethyl]-3-hydroxy-5-[4-(6-methoxypyridin-3-yl)phenyl]pentanoic acid (Compound No. 39)
Mass (m/z): 511.0 (M$^+$+1);

(2S,3R)-2-[2-(5-fluoro-4-oxo-1,2,3-benzotriazin-3(4H)-yl)
ethyl]-3-hydroxy-5-[4-(6-methoxypyridin-3-yl)phenyl]
pentanoic acid (Compound No. 40)
Mass (m/z): 493.3 (M$^+$+1);

(2S,3R)-3-hydroxy-2-[2-(8-methoxy-4-oxo-1,2,3-benzotriazin-3(4H)-yl)ethyl]-5-[4-(6-methylpyridin-3-yl)phenyl]
pentanoic acid (Compound No. 41)
Mass (m/z): 489.0 (M$^+$+1);

(2S,3R)-3-hydroxy-2-{2-[5-(6-methoxypyridin-3-yl)-4-
oxo-1,2,3-benzotriazin-3(4H)-yl]ethyl}-5-[4-(6-methoxypyridin-3-yl)phenyl]pentanoic acid (Compound No. 42)
Mass (m/z): 582.0 (M$^+$+1);

(2S,3R)-5-(4'-chloro-3'-fluorobiphenyl-4-yl)-2-[2-(1,3-dioxo-1,3-dihydro-2H-isoindol-2-yl)ethyl]-3-hydroxypentanoic acid (Compound No. 43)
Mass (m/z): 519.0 (M$^+$+23);

(2S,3R)-2-[2-(1,3-dioxo-1,3-dihydro-2H-isoindol-2-yl)
ethyl]-3-hydroxy-5-[4-(1-isobutyl-1H-pyrazol-4-yl)phenyl]pentanoic acid (Compound No. 44)
Mass (m/z): 490.0 (M$^+$+1);

(2S,3R)-5-biphenyl-4-yl-2-[2-(1,3-dioxo-1,3-dihydro-2H-isoindol-2-yl)ethyl]-3-hydroxypentanoic acid (Compound No. 45)
Mass (m/z): 444.0 (M$^+$+1);

(2S,3R)-2-[2-(1,3-dioxo-1,3-dihydro-2H-isoindol-2-yl)ethyl]-5-(3'-fluoro-4'-methylbiphenyl-4-yl)-3-hydroxypentanoic acid (Compound No. 46)
Mass (m/z): 476.0 (M$^+$+1);

(2S,3R)-5-(3',3'-difluoro-4'-methoxybiphenyl-4-yl)-2-[2-(1,3-dioxo-1,3-dihydro-2H-isoindol-2-yl)ethyl]-3-hydroxypentanoic acid (Compound No. 47)
Mass (m/z): 510.0 (M$^+$+1);

(2S,3R)-5-[4-(2,3-dihydro-1,4-benzodioxin-6-yl)phenyl]-2-[2-(1,3-dioxo-1,3-dihydro-2H-isoindol-2-yl)ethyl]-3-hydroxypentanoic acid (Compound No. 48)
Mass (m/z): 502.0 (M$^+$+1);

(2S,3R)-2-[2-(1,3-dioxo-1,3-dihydro-2H-isoindol-2-yl)ethyl]-3-hydroxy-5-[4-(1H-tetrazol-1-yl)phenyl]pentanoic acid (Compound No. 49)
Mass (m/z): 458.0 (M$^+$+23);

(2S,3R)-2-[2-(1,3-dioxo-1,3-dihydro-2H-isoindol-2-yl)ethyl]-5-[2-fluoro-4-(6-methoxypyridin-3-yl)phenyl]-3-hydroxypentanoic acid (Compound No. 50)
Mass (m/z): 493.0 (M$^+$+1);

(2S,3R)-5-(3'-fluoro-4'-methylbiphenyl-4-yl)-3-hydroxy-2-[2-(4-oxo-1,2,3-benzotriazin-3(4H)-yl)ethyl]pentanoic acid (Compound No. 51)
Mass (m/z): 498.0 (M$^+$+23);

(2S,3R)-3-hydroxy-5-[4-(1-isobutyl-1H-pyrazol-4-yl)phenyl]-2-[2-(4-oxo-1,2,3-benzotriazin-3(4H)-yl)ethyl]pentanoic acid (Compound No. 52)
Mass (m/z): 490.0 (M$^+$+1);

(2S,3R)-5-biphenyl-4-yl-3-hydroxy-2-[2-(4-oxo-1,2,3-benzotriazin-3(4H)-yl)ethyl]pentanoic acid (Compound No. 53)
Mass (m/z): 444.0 (M$^+$+1);

(2S,3R)-3-hydroxy-5-[4-(6-methoxypyridin-3-yl)phenyl]-2-[2-(7-methyl-4-oxo-1,2,3-benzotriazin-3(4H)-yl)ethyl]pentanoic acid (Compound No. 54)
Mass (m/z): 489.34 (M$^+$+1);

(2S,3R)-2-[2-(1,3-dioxo-1,3-dihydro-2H-isoindol-2-yl)ethyl]-5-[6-(3-fluoro-4-methoxyphenyl)pyridin-3-yl]-3-hydroxypentanoic acid (Compound No. 55)
Mass (m/z): 493.16 (M$^+$+1);

(2S,3R)-5-(4'-chloro-3-fluorobiphenyl-4-yl)-2-[2-(1,3-dioxo-1,3-dihydro-2H-isoindol-2-yl)ethyl]-3-hydroxypentanoic acid (Compound No. 56)
Mass (m/z): 496.13 (M$^+$+1);

(2S,3R)-2-[2-(1,3-dioxo-1,3-dihydro-2H-isoindol-2-yl)ethyl]-3-hydroxy-5-[6-(4-methoxyphenyl)pyridin-3-yl]pentanoic acid (Compound No. 57)
Mass (m/z): 475.13 (M$^+$+1);

(2S,3R)-2-[2-(1,3-dioxo-1,3-dihydro-2H-isoindol-2-yl)ethyl]-5-(3-fluoro-4'-methoxybiphenyl-4-yl)-3-hydroxypentanoic acid (Compound No. 58)
Mass (m/z): 492.13 (M$^+$+1);

(2S,3R)-5-[6-(4-chlorophenyl)pyridin-3-yl]-2-[2-(1,3-dioxo-1,3-dihydro-2H-isoindol-2-yl)ethyl]-3-hydroxypentanoic acid (Compound No. 59)
Mass (m/z): 479.12 (M$^+$+1);

(2S,3R)-2-[2-(1,3-dioxo-1,3-dihydro-2H-isoindol-2-yl)ethyl]-3-hydroxy-5-(6'-methoxy-2,3'-bipyridin-5-yl)pentanoic acid (Compound No. 60)
Mass (m/z): 476.16 (M$^+$+1);

(2S,3R)-5-[4-(4-chlorophenyl)-2-thienyl]-2-[2-(1,3-dioxo-1,3-dihydro-2H-isoindol-2-yl)ethyl]-3-hydroxypentanoic acid (Compound No. 61)
Mass (m/z): 484.0 (M$^+$+1);

(2S,3R)-2-[2-(1,3-dioxo-1,3-dihydro-2H-isoindol-2-yl)ethyl]-3-hydroxy-5-[4-(6-methoxypyridin-3-yl)-2-thienyl]pentanoic acid (Compound No. 62)
Mass (m/z): 481.0 (M$^+$+1);

(2S,3R)-2-[2-(1,3-dioxo-1,3-dihydro-2H-isoindol-2-yl)ethyl]-3-hydroxy-5-{4-[4-(trifluoromethyl)phenyl]-2-thienyl}pentanoic acid (Compound No. 63)
Mass (m/z): 518.0 (M$^+$+1);

(2S,3R)-2-[2-(1,3-dioxo-1,3-dihydro-2H-isoindol-2-yl)ethyl]-5-[4-(3-fluoro-4-methoxyphenyl)-2-thienyl]-3-hydroxypentanoic acid (Compound No. 64)
Mass (m/z): 498.0 (M$^+$+1);

(2S,3R)-3-hydroxy-2-[2-(7-methyl-4-oxo-1,2,3-benzotriazin-3(4H)-yl)ethyl]-5-[4'-(trifluoromethyl)biphenyl-4-yl]pentanoic acid (Compound No. 65)
Mass (m/z): 526.0 (M$^+$+1);

(2S,3R)-3-hydroxy-2-[2-(6-methyl-4-oxo-1,2,3-benzotriazin-3(4H)-yl)ethyl]-5-[4'-(trifluoromethyl)biphenyl-4-yl]pentanoic acid (Compound No. 66)
Mass (m/z): 526.0 (M$^+$+1);

(2S,3R)-2-[2-(7-chloro-4-oxo-1,2,3-benzotriazin-3(4H)-yl)ethyl]-3-hydroxy-5-(4'-methylbiphenyl-4-yl)pentanoic acid (Compound No. 67)
Mass (m/z): 492.0 (M$^+$+1);

(2S,3R)-3-hydroxy-2-[2-(8-methoxy-4-oxo-1,2,3-benzotriazin-3(4H)-yl)ethyl]-5-[4'-(trifluoromethyl)biphenyl-4-yl]pentanoic acid (Compound No. 68)
Mass (m/z): 542.29 (M$^+$+1);

(2S,3R)-2-[2-(6,7-difluoro-4-oxo-1,2,3-benzotriazin-3(4H)-yl)ethyl]-3-hydroxy-5-[4'-(trifluoromethyl)biphenyl-4-yl]pentanoic acid (Compound No. 69)
Mass (m/z): 548.54 (M$^+$+1);

(2S,3R)-2-[2-(1,3-dioxo-1,3-dihydro-2H-isoindol-2-yl)ethyl]-5-[2-fluoro-5-(6-methoxypyridin-3-yl)phenyl]-3-hydroxypentanoic acid (Compound No. 70)
Mass (m/z): 493.30 (M$^+$+1);

(2S,3R)-5-(4'-chloro-4-fluorobiphenyl-3-yl)-2-[2-(1,3-dioxo-1,3-dihydro-2H-isoindol-2-yl)ethyl]-3-hydroxypentanoic acid (Compound No. 71)
Mass (m/z): 495.72 (M$^+$+1);

(2S,3R)-2-[2-(1,3-dioxo-1,3-dihydro-2H-isoindol-2-yl)ethyl]-5-[6-fluoro-4'-(trifluoromethyl)biphenyl-3-yl]-3-hydroxypentanoic acid (Compound No. 72)
Mass (m/z): 530.13 (M$^+$+1);

(2S,3R)-2-[2-(1,3-dioxo-1,3-dihydro-2H-isoindol-2-yl)ethyl]-5-[4-fluoro-3-(6-methoxypyridin-3-yl)phenyl]-3-hydroxypentanoic acid (Compound No. 73)
Mass (m/z): 493.37 (M$^+$+1);

(2S,3R)-5-(4'-chloro-6-fluorobiphenyl-3-yl)-2-[2-(1,3-dioxo-1,3-dihydro-2H-isoindol-2-yl)ethyl]-3-hydroxypentanoic acid (Compound No. 74)
Mass (m/z): 496.26 (M$^+$+1);

(2S,3R)-5-(3',6-difluoro-4'-methoxybiphenyl-3-yl)-2-[2-(1,3-dioxo-1,3-dihydro-2H-isoindol-2-yl)ethyl]-3-hydroxypentanoic acid (Compound No. 75)
Mass (m/z): 509.77 (M$^+$+1);

(2S,3R)-2-[2-(5-fluoro-4-oxo-1,2,3-benzotriazin-3(4H)-yl)ethyl]-3-hydroxy-5-(4'-methoxybiphenyl-4-yl)pentanoic acid (Compound No. 76)
Mass (m/z): 492.56 (M$^+$+1);

(2S,3R)-5-(4'-fluorobiphenyl-4-yl)-2-[2-(5-fluoro-4-oxo-1,2,3-benzotriazin-3(4H)-yl)ethyl]-3-hydroxypentanoic acid (Compound No. 77)
Mass (m/z): 480.0 (M$^+$+1);

(2S,3R)-3-hydroxy-2-[2-(6-methyl-4-oxo-1,2,3-benzotriazin-3(4H)-yl)ethyl]-5-[4-(1-methyl-1H-pyrazol-4-yl)phenyl]pentanoic acid (Compound No. 78)
Mass (m/z): 462.19 (M$^+$+1);

(2S,3R)-2-[2-(5-chloro-1,3-dioxo-1,3-dihydro-2H-isoindol-2-yl)ethyl]-3-hydroxy-5-[4'-(trifluoromethyl)biphenyl-4-yl]pentanoic acid (Compound No. 79)
Mass (m/z): 546.32 (M$^+$+1);

(2S,3R)-2-[2-(4-fluoro-1,3-dioxo-1,3-dihydro-2H-isoindol-2-yl)ethyl]-3-hydroxy-5-[4'-(trifluoromethyl)biphenyl-4-yl]pentanoic acid (Compound No. 80)
Mass (m/z): 529.25 (M$^+$+1);

(2S,3R)-5-(3',4'-difluorobiphenyl-4-yl)-2-[2-(5-fluoro-4-oxo-1,2,3-benzotriazin-3(4H)-yl)ethyl]-3-hydroxypentanoic acid (Compound No. 81)
Mass (m/z): 498.27 (M$^+$+1);

(2S,3R)-3-hydroxy-2-[2-(4-oxo-1,2,3-benzotriazin-3(4H)-yl)ethyl]-5-phenylpentanoic acid (Compound No. 82)
Mass (m/z): 368.0 (M$^+$+1);

(2S,3R)-2-[2-(1,3-dioxo-1,3-dihydro-2H-isoindol-2-yl)ethyl]-3-hydroxy-5-phenylpentanoic acid (Compound No. 83)
Mass (m/z): 368.07 (M$^+$+1);

(2S,3R)-2-[2-(1,3-dioxo-1,3-dihydro-2H-isoindol-2-yl)ethyl]-3-hydroxy-5-[4(trifluoromethyl)phenyl]pentanoic acid (Compound No. 84)
Mass (m/z): 458.0 (M$^+$+23);

(2S,3R)-5-(4-tert-butylphenyl)-2-[2-(1,3-dioxo-1,3-dihydro-2H-isoindol-2-yl)ethyl]-3-hydroxypentanoic acid (Compound No. 85)
Mass (m/z): 424.0 (M$^+$+1);

(2S,3R)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 86)
Mass (m/z): 474.87 (M$^+$+1);

(2S,3R)-5-(4'-chlorobiphenyl-4-yl)-2-[2-(1,3-dioxo-1,3-dihydro-2H-isoindol-2-yl)ethyl]-3-hydroxypentanoic acid (Compound No. 87)
Mass (m/z): 478.09 (M$^+$+1);

(2S,3R)-2-[2-(1,3-dioxo-1,3-dihydro-2H-isoindol-2-yl)ethyl]-3-hydroxy-5-[4-(6-methoxypyridin-3-yl)phenyl]pentanoic acid (Compound No. 88)
Mass (m/z): 474.88 (M$^+$+1);

(2R,3R)-5-(4'-chlorobiphenyl-4-yl)-2-[2-(1,3-dioxo-1,3-dihydro-2H-isoindol-2-yl)ethyl]-3-hydroxypentanoic acid (Compound No. 89)
Mass (m/z): 478.2 (M$^+$+1);

(2S,3R)-3-hydroxy-2-[2-(7-methyl-4-oxo-1,2,3-benzotriazin-3(4H)-yl)ethyl]-5-[4-(1-methyl-1H-pyrazol-4-yl)phenyl]pentanoic acid (Compound No. 90)
Mass (m/z): 462.32 (M$^+$+1);

(2S,3R)-3-hydroxy-2-[2-(8-methoxy-4-oxo-1,2,3-benzotriazin-3(4H)-yl)ethyl]-5-[4-(1-methyl-1H-pyrazol-4-yl)phenyl]pentanoic acid (Compound No. 91)
Mass (m/z): 478.38 (M$^+$+1);

(2S,3R)-2-[2-(7-chloro-4-oxo-1,2,3-benzotriazin-3(4H)-yl)ethyl]-5-(3',4'-difluorobiphenyl-4-yl)-3-hydroxypentanoic acid (Compound No. 92)
Mass (m/z): 514.20 (M$^+$+1);

(2S,3R)-2-[2-(7-chloro-4-oxo-1,2,3-benzotriazin-3(4H)-yl)ethyl]-3-hydroxy-5-(4'-methoxybiphenyl-4-yl)pentanoic acid (Compound No. 93)
Mass (m/z): 508.29 (M$^+$+1);

(2S,3R)-2-[2-(7-chloro-4-oxo-1,2,3-benzotriazin-3(4H)-yl)ethyl]-5-(4'-fluorobiphenyl-4-yl)-3-hydroxypentanoic acid (Compound No. 94);

(2S,3R)-2-[2-(7-chloro-4-oxo-1,2,3-benzotriazin-3(4H)-yl)ethyl]-3-hydroxy-5-[4-(6-methylpyridin-3-yl)phenyl]pentanoic acid (Compound No. 95)
Mass (m/z): 493.37 (M$^+$+1);

(2R,3R)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 96)
Mass (m/z): 474.87 (M$^+$+1);

(2S,3R)-5-(2',4'-difluorobiphenyl-4-yl)-2-[2-(1,3-dioxo-1,3-dihydro-2H-isoindol-2-yl)ethyl]-3-hydroxypentanoic acid (Compound No. 97)
Mass (m/z): 480.13 (M$^+$+1);

(2S,3R)-2-[2-(6-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 98)
Mass (m/z): 482.15 (M$^+$+1);

(2S,3R)-2-[2-(5-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 99)
Mass (m/z): 482.15 (M$^+$+1);

(2S,3R)-2-[2-(1,3-dioxo-1,3-dihydro-2H-isoindol-2-yl)ethyl]-3-hydroxy-5-(4'-isopropylbiphenyl-4-yl)pentanoic acid (Compound No. 100)
Mass (m/z): 486.18 (M$^+$+1);

(2S,3R)-5-(3'-chloro-4'-fluorobiphenyl-4-yl)-2-[2-(1,3-dioxo-1,3-dihydro-2H-isoindol-2-yl)ethyl]-3-hydroxypentanoic acid (Compound No. 101)
Mass (m/z): 496.12 (M$^+$+1);

(2S,3R)-5-(4'-butylbiphenyl-4-yl)-3-hydroxy-2-[2-(4-oxo-1,2,3-benzotriazin-3(4H)-yl)ethyl]pentanoic acid (Compound No. 102)
Mass (m/z): 500.42 (M$^+$+1);

(2S,3R)-5-(2'-fluorobiphenyl-4-yl)-3-hydroxy-2-[2-(4-oxo-1,2,3-benzotriazin-3(4H)-yl)ethyl]pentanoic acid (Compound No. 103)
Mass (m/z): 462.32 (M$^+$+1);

(2S,3R)-2-[2-(5-fluoro-4-oxo-1,2,3-benzotriazin-3(4H)-yl)ethyl]-3-hydroxy-5-[4-(1-methyl-1H-pyrazol-4-yl)phenyl]pentanoic acid (Compound No. 104)
Mass (m/z): 466.31 (M$^+$+1);

(2S,3R)-3-hydroxy-2-[2-(8-methyl-4-oxo-1,2,3-benzotriazin-3(4H)-yl)ethyl]-5-[4-(1-methyl-1H-pyrazol-4-yl)phenyl]pentanoic acid (Compound No. 105)
Mass (m/z): 462.38 (M$^+$+1);

(2S,3R)-2-[2-(1,3-dioxo-1,3-dihydro-2H-isoindol-2-yl)ethyl]-3-hydroxy-5-{6-[4-(trifluoromethyl)phenyl]pyridin-3-yl}pentanoic acid (Compound No. 106)
Mass (m/z): 513.35 (M$^+$+1);

(2S,3R)-5-[6-(3,4-difluorophenyl)pyridin-3-yl]-2-[2-(1,3-dioxo-1,3-dihydro-2H-isoindol-2-yl)ethyl]-3-hydroxypentanoic acid (Compound No. 107)
Mass (m/z): 481.32 (M$^+$+1);

(2S,3R)-5-[6-(4-chloro-3-fluorophenyl)pyridin-3-yl]-2-[2-(1,3-dioxo-1,3-dihydro-2H-isoindol-2-yl)ethyl]-3-hydroxypentanoic acid (Compound No. 108)
Mass (m/z): 497.30 (M$^+$+1);

(2S,3R)-2-[2-(1,3-dioxo-1,3-dihydro-2H-isoindol-2-yl)ethyl]-5-[6-(4-fluorophenyl)pyridin-3-yl]-3-hydroxypentanoic acid (Compound No. 109)
Mass (m/z): 463.35 (M$^+$+1);

(2S,3R)-2-[2-(1,3-dioxo-1,3-dihydro-2H-isoindol-2-yl)ethyl]-5-[6-(3-fluoro-4-methylphenyl)pyridin-3-yl]-3-hydroxypentanoic acid (Compound No. 110)
Mass (m/z): 477.34 (M$^+$+1);

(2S,3R)-2-[2-(7-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 111)
Mass (m/z): 482.38 (M$^+$+1);

(2S,3R)-2-[2-(8-chloro-4-oxo-1,2,3-benzotriazin-3(4H)-yl)ethyl]-3-hydroxy-5-[4-(1-methyl-1H-pyrazol-4-yl)phenyl]pentanoic acid (Compound No. 112);

(2S,3R)-2-[2-(6,7-difluoro-4-oxo-1,2,3-benzotriazin-3(4H)-yl)ethyl]-3-hydroxy-5-[4-(1-methyl-1H-pyrazol-4-yl)phenyl]pentanoic acid (Compound No. 113)
Mass (m/z): 484.39 (M$^+$+1);

(2S,3R)-3-hydroxy-2-[2-(7-methyl-4-oxo-1,2,3-benzotriazin-3(4H)-yl)ethyl]-5-[4'-(trifluoromethoxy)biphenyl-4-yl]pentanoic acid (Compound No. 114)
Mass (m/z): 542.36 (M$^+$+1);

(2S,3R)-3-hydroxy-5-(4'-methylbiphenyl-4-yl)-2-[2-(7-methyl-4-oxo-1,2,3-benzotriazin-3(4H)-yl)ethyl]pentanoic acid (Compound No. 115)
Mass (m/z): 472.12 (M$^+$+1);

(2S,3R)-5-(4'-fluorobiphenyl-4-yl)-3-hydroxy-2-[2-(7-methyl-4-oxo-1,2,3-benzotriazin-3(4H)-yl)ethyl]pentanoic acid (Compound No. 116)
Mass (m/z): 476.23 (M$^+$+1).

(2S,3R)-5-(3',4'-difluorobiphenyl-4-yl)-3-hydroxy-2-[2-(7-methyl-4-oxo-1,2,3-benzotriazin-3(4H)-yl)ethyl]pentanoic acid (Compound No. 117)
Mass (m/z): 494.24 (M$^+$+1);

(2S,3R)-3-hydroxy-2-[2-(7-methyl-4-oxo-1,2,3-benzotriazin-3(4H)-yl)ethyl]-5-[4-(6-methylpyridin-3-yl)phenyl]pentanoic acid (Compound No. 118)
Mass (m/z): 473.38 (M$^+$+1);

(2S,3R)-5-[4-(2,3-dihydro-1,4-benzodioxin-6-yl)phenyl]-3-hydroxy-2-[2-(7-methyl-4-oxo-1,2,3-benzotriazin-3(4H)-yl)ethyl]pentanoic acid (Compound No. 119)
Mass (m/z): 516.28 (M$^+$+1);

(2R,3S)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 120)
Mass (m/z): 474.87 (M$^+$+1);

(2S,3R)-2-[2-(5-chloro-4-oxo-1,2,3-benzotriazin-3(4H)-yl)ethyl]-3-hydroxy-5-(6'-methoxy-2,3'-bipyridin-5-yl)pentanoic acid (Compound No. 121)
Mass (m/z): 510.23 (M$^+$+1);

(2S,3R)-2-[2-(7-chloro-4-oxo-1,2,3-benzotriazin-3(4H)-yl)ethyl]-3-hydroxy-5-(6'-methoxy-2,3'-bipyridin-5-yl)pentanoic acid (Compound No. 122)
Mass (m/z): 510.23 (M$^+$+1);

(2S,3R)-2-[2-(6,7-difluoro-4-oxo-1,2,3-benzotriazin-3(4H)-yl)ethyl]-3-hydroxy-5-(6'-methoxy-2,3'-bipyridin-5-yl)pentanoic acid (Compound No. 123)
Mass (m/z): 512.31 (M$^+$+1);

(2S,3R)-5-(3'-fluoro-4'-methylbiphenyl-4-yl)-3-hydroxy-2-[2-(7-methyl-4-oxo-1,2,3-benzotriazin-3(4H)-yl)ethyl]pentanoic acid (Compound No. 124)
Mass (m/z): 490.30 (M$^+$+1);

(2S,3R)-3-hydroxy-5-[4-(1-isobutyl-1H-pyrazol-4-yl)phenyl]-2-[2-(7-methyl-4-oxo-1,2,3-benzotriazin-3(4H)-yl)ethyl]pentanoic acid (Compound No. 125)
Mass (m/z): 504.33 (M$^+$+1);

(2S,3R)-2-[2-(5-fluoro-4-oxo-1,2,3-benzotriazin-3(4H)-yl)ethyl]-3-hydroxy-5-(6'-methoxy-2,3'-bipyridin-5-yl)pentanoic acid (Compound No. 126)
Mass (m/z): 510.23 (M$^+$+1);

(2S,3R)-5-(4'-fluorobiphenyl-4-yl)-3-hydroxy-2-[2-(8-methoxy-4-oxo-1,2,3-benzotriazin-3(4H)-yl)ethyl]pentanoic acid (Compound No. 127)
Mass (m/z): 492.26 (M$^+$+1).

(2S,3R)-5-(3',4'-difluorobiphenyl-4-yl)-3-hydroxy-2-[2-(8-methoxy-4-oxo-1,2,3-benzotriazin-3(4H)-yl)ethyl]pentanoic acid (Compound No. 128)
Mass (m/z): 510.30 (M$^+$+1);

(2S,3R)-3-hydroxy-5-(4'-methoxybiphenyl-4-yl)-2-[2-(8-methoxy-4-oxo-1,2,3-benzotriazin-3(4H)-yl)ethyl]pentanoic acid (Compound No. 129)
Mass (m/z): 504.38 (M$^+$+1);

(2S,3R)-2-[2-(7-chloro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 130)
Mass (m/z): 547.29 (M$^+$+1);

(2S,3R)-2-[2-(6,7-difluoro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 131)
Mass (m/z): 549.30 (M$^+$+1);

(2S,3R)-2-[2-(5-chloro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 132)
Mass (m/z): 547.29 (M$^+$+1);

(2S,3R)-3-hydroxy-2-[2-(7-methyl-4-oxo-1,2,3-benzotriazin-3(4H)-yl)ethyl]-5-{6-[4-(trifluoromethyl)phenyl]pyridin-3-yl}pentanoic acid (Compound No. 133)
Mass (m/z): 527.40 (M$^+$+1);

(2S,3R)-2-[2-(5-fluoro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 134)
Mass (m/z): 531.36 (M$^+$+1);

(2S,3R)-3-hydroxy-2-[2-(8-methoxy-4-oxo-1,2,3-benzotriazin-3(4H)-yl)ethyl]-5-(4'-methylbiphenyl-4-yl)pentanoic acid (Compound No. 135)
Mass (m/z): 488.34 (M$^+$+1);

(2S,3R)-5-(3'-fluoro-4'-methylbiphenyl-4-yl)-2-[2-(5-fluoro-4-oxo-1,2,3-benzotriazin-3(4H)-yl)ethyl]-3-hydroxypentanoic acid (Compound No. 136)
Mass (m/z): 494.33 (M$^+$+1);

(2S,3R)-2-[2-(6,7-difluoro-4-oxo-1,2,3-benzotriazin-3(4H)-yl)ethyl]-3-hydroxy-5-(4'-methylbiphenyl-4-yl)pentanoic acid (Compound No. 137)
Mass (m/z): 494.33 (M$^+$+1);

(2S,3R)-2-[2-(5-fluoro-4-oxo-1,2,3-benzotriazin-3(4H)-yl)ethyl]-3-hydroxy-5-(4'-methylbiphenyl-4-yl)pentanoic acid (Compound No. 138)
Mass (m/z): 476.30 (M$^+$+1);

(2S,3R)-5-(4'-chlorobiphenyl-4-yl)-2-[2-(5-fluoro-4-oxo-1,2,3-benzotriazin-3(4H)-yl)ethyl]-3-hydroxypentanoic acid (Compound No. 139)
Mass (m/z): 496.30 (M$^+$+1);

(2S,3R)-3-hydroxy-5-(6'-methoxy-2,3'-bipyridin-5-yl)-2-[2-(4-oxo-1,2,3-benzotriazin-3(4H)-yl)ethyl]pentanoic acid (Compound No. 140)
Mass (m/z): 476.35 (M$^+$+1);

(2S,3R)-3-hydroxy-5-(6'-methoxy-2,3'-bipyridin-5-yl)-2-[2-(6-methyl-4-oxo-1,2,3-benzotriazin-3(4H)-yl)ethyl]pentanoic acid (Compound No. 141);

(2S,3R)-3-hydroxy-5-(6'-methoxy-2,3'-bipyridin-5-yl)-2-[2-(7-methyl-4-oxo-1,2,3-benzotriazin-3(4H)-yl)ethyl]pentanoic acid (Compound No. 142)
Mass (m/z): 490.34 (M$^+$+1);

(2S,3S)-3-hydroxy-5-[4-(6-methoxypyridin-3-yl)phenyl]-2-[2-(4-oxo-1,2,3-benzotriazin-3(4H)-yl)ethyl]pentanoic acid (Compound No. 143)
Mass (m/z): 475.21 (M$^+$+1);

(2S,3R)-2-[2-(6,7-difluoro-4-oxo-1,2,3-benzotriazin-3(4H)-yl)ethyl]-5-(3'-fluoro-4'-methylbiphenyl-4-yl)-3-hydroxypentanoic acid (Compound No. 144)
Mass (m/z): 512.32 (M$^+$+1);

(2S,3R)-5-(4'-chlorobiphenyl-4-yl)-2-[2-(6,7-difluoro-4-oxo-1,2,3-benzotriazin-3(4H)-yl)ethyl]-3-hydroxypentanoic acid (Compound No. 145)
Mass (m/z): 514.37 (M$^+$+1);

(2S,3R)-5-(3'-fluoro-4'-methylbiphenyl-4-yl)-3-hydroxy-2-[2-(8-methoxy-4-oxo-1,2,3-benzotriazin-3(4H)-yl)ethyl]pentanoic acid (Compound No. 146)
Mass (m/z): 506.38 (M$^+$+1);

(2S,3R)-5-[4-(2,3-dihydro-1,4-benzodioxin-6-yl)phenyl]-3-hydroxy-2-[2-(8-methoxy-4-oxo-1,2,3-benzotriazin-3(4H)-yl)ethyl]pentanoic acid (Compound No. 147)
Mass (m/z): 532.38 (M$^+$+1);

(2S,3R)-5-[4-(6-chloropyridin-3-yl)phenyl]-3-hydroxy-2-[2-(4-oxo-1,2,3-benzotriazin-3(4H)-yl)ethyl]pentanoic acid (Compound No. 148)
Mass (m/z): 479.36 (M$^+$+1);

(2S,3R)-3-hydroxy-2-[2-(6-methoxy-4-oxo-1,2,3-benzotriazin-3(4H)-yl)ethyl]-5-[4'-(trifluoromethyl)biphenyl-4-yl]pentanoic acid (Compound No. 149)
Mass (m/z): 542.11 (M$^+$+1);

(2S,3R)-3-hydroxy-2-[2-(7-methoxy-4-oxo-1,2,3-benzotriazin-3(4H)-yl)ethyl]-5-[4'-(trifluoromethyl)biphenyl-4-yl]pentanoic acid (Compound No. 150)
Mass (m/z): 542.11 (M$^+$+1);

(2S,3R)-3-hydroxy-2-[2-(6-methoxy-4-oxo-1,2,3-benzotriazin-3(4H)-yl)ethyl]-5-(4'-methylbiphenyl-4-yl)pentanoic acid (Compound No. 151)
Mass (m/z): 488.09 (M$^+$+1);

(2S,3R)-3-hydroxy-5-(4'-methoxybiphenyl-4-yl)-2-[2-(6-methoxy-4-oxo-1,2,3-benzotriazin-3(4H)-yl)ethyl]pentanoic acid (Compound No. 152)
Mass (m/z): 504.06 (M$^+$+1);

(2S,3R)-5-[2-fluoro-4-(6-methoxypyridin-3-yl)phenyl]-3-hydroxy-2-[2-(4-oxo-1,2,3-benzotriazin-3(4H)-yl)ethyl]pentanoic acid (Compound No. 153)
Mass (m/z): 493.01 (M$^+$+1);

(2S,3R)-5-[2-fluoro-4-(6-methoxypyridin-3-yl)phenyl]-3-hydroxy-2-[2-(7-methoxy-4-oxo-1,2,3-benzotriazin-3(4H)-yl)ethyl]pentanoic acid (Compound No. 154)
Mass (m/z): 523.02 (M$^+$+1);

(2S,3R)-5-[2-fluoro-4-(6-methoxypyridin-3-yl)phenyl]-2-[2-(5-fluoro-4-oxo-1,2,3-benzotriazin-3(4H)-yl)ethyl]-3-hydroxypentanoic acid (Compound No. 155)
Mass (m/z): 511.04 (M$^+$+1);

(2S,3R)-5-[2-fluoro-4-(6-methoxypyridin-3-yl)phenyl]-3-hydroxy-2-[2-(7-methyl-4-oxo-1,2,3-benzotriazin-3(4H)-yl)ethyl]pentanoic acid (Compound No. 156)
Mass (m/z): 507.05 (M$^+$+1);

(2S,3R)-5-[2-fluoro-4-(6-methoxypyridin-3-yl)phenyl]-3-hydroxy-2-[2-(6-methyl-4-oxo-1,2,3-benzotriazin-3(4H)-yl)ethyl]pentanoic acid (Compound No. 157)
Mass (m/z): 507.05 (M$^+$+1);

(2S,3R)-3-hydroxy-5-(4'-methoxybiphenyl-4-yl)-2-[2-(7-methoxy-4-oxo-1,2,3-benzotriazin-3(4H)-yl)ethyl]pentanoic acid (Compound No. 158)
Mass (m/z): 504.09 (M$^+$+1);

(2S,3R)-5-(4'-chlorobiphenyl-4-yl)-3-hydroxy-2-[2-(6-methoxy-4-oxo-1,2,3-benzotriazin-3(4H)-yl)ethyl]pentanoic acid (Compound No. 159)
Mass (m/z): 508.03 (M$^+$+1);

(2S,3R)-3-hydroxy-2-[2-(7-methoxy-4-oxo-1,2,3-benzotriazin-3(4H)-yl)ethyl]-5-[4-(6-methoxypyridin-3-yl)phenyl]pentanoic acid (Compound No. 160)
Mass (m/z): 505.11 (M$^+$+1);

(2S,3R)-5-(3',4'-difluorobiphenyl-4-yl)-3-hydroxy-2-[2-(7-methoxy-4-oxo-1,2,3-benzotriazin-3(4H)-yl)ethyl]pentanoic acid (Compound No. 161)
Mass (m/z): 510.04 (M$^+$+1);

(2S,3R)-3-hydroxy-2-[2-(6-methoxy-4-oxo-1,2,3-benzotriazin-3(4H)-yl)ethyl]-5-[4-(6-methoxypyridin-3-yl)phenyl]pentanoic acid (Compound No. 162)
Mass (m/z): 505.11 (M$^+$+1);

(2S,3R)-2-[2-(5-chloro-4-oxo-1,2,3-benzotriazin-3(4H)-yl)ethyl]-5-[2-fluoro-4-(6-methoxypyridin-3-yl)phenyl]-3-hydroxypentanoic acid (Compound No. 163)
Mass (m/z): 526.95 (M$^+$+1);

(2S,3R)-2-[2-(6,7-difluoro-4-oxo-1,2,3-benzotriazin-3(4H)-yl)ethyl]-5-[2-fluoro-4-(6-methoxypyridin-3-yl)phenyl]-3-hydroxypentanoic acid (Compound No. 164)
Mass (m/z): 529.00 (M$^+$+1);

(2S,3R)-5-[2-fluoro-4-(6-methoxypyridin-3-yl)phenyl]-3-hydroxy-2-[2-(5-methyl-4-oxo-1,2,3-benzotriazin-3(4H)-yl)ethyl]pentanoic acid (Compound No. 165)
Mass (m/z): 507.03 (M$^+$+1);

(2S,3R)-5-(4'-fluorobiphenyl-4-yl)-3-hydroxy-2-[2-(5-methyl-4-oxo-1,2,3-benzotriazin-3(4H)-yl)ethyl]pentanoic acid (Compound No. 166)
Mass (m/z): 476.01 (M$^+$+1);

(2S,3R)-3-hydroxy-5-[4-(6-methoxypyridin-3-yl)phenyl]-2-[2-(5-methyl-4-oxo-1,2,3-benzotriazin-3(4H)-yl)ethyl]pentanoic acid (Compound No. 167)
Mass (m/z): 489.05 (M$^+$+1);

(2S,3R)-3-hydroxy-5-(4'-methoxybiphenyl-4-yl)-2-[2-(5-methyl-4-oxo-1,2,3-benzotriazin-3(4H)-yl)ethyl]pentanoic acid (Compound No. 168)
Mass (m/z): 488.06 (M$^+$+1);

(2S,3R)-3-hydroxy-5-(4'-methylbiphenyl-4-yl)-2-[2-(5-methyl-4-oxo-1,2,3-benzotriazin-3(4H)-yl)ethyl]pentanoic acid (Compound No. 169)
Mass (m/z): 472.03 (M$^+$+1);

(2S,3R)-5-(4'-chlorobiphenyl-4-yl)-3-hydroxy-2-[2-(5-methyl-4-oxo-1,2,3-benzotriazin-3(4H)-yl)ethyl]pentanoic acid (Compound No. 170)
Mass (m/z): 491.98 (M$^+$+1);

(2S,3R)-5-(4'-fluorobiphenyl-4-yl)-3-hydroxy-2-[2-(6-methoxy-4-oxo-1,2,3-benzotriazin-3(4H)-yl)ethyl]pentanoic acid (Compound No. 171)
Mass (m/z): 492.00 (M$^+$+1);

(2S,3R)-5-(3',4'-difluorobiphenyl-4-yl)-3-hydroxy-2-[2-(6-methoxy-4-oxo-1,2,3-benzotriazin-3(4H)-yl)ethyl]pentanoic acid (Compound No. 172)
Mass (m/z): 509.98 (M$^+$+1);

(2S,3R)-3-hydroxy-2-[2-(6-methoxy-4-oxo-1,2,3-benzotriazin-3(4H)-yl)ethyl]-5-[4'-(trifluoromethoxy)biphenyl-4-yl]pentanoic acid (Compound No. 173)
Mass (m/z): 557.99 (M$^+$+1);

(2S,3R)-5-(3'-fluoro-4'-methylbiphenyl-4-yl)-3-hydroxy-2-[2-(6-methoxy-4-oxo-1,2,3-benzotriazin-3(4H)-yl)ethyl]pentanoic acid (Compound No. 174)
Mass (m/z): 506.04 (M$^+$+1);

(2S,3R)-2-[2-(7-chloro-4-oxo-1,2,3-benzotriazin-3(4H)-yl)ethyl]-5-[2-fluoro-4-(6-methoxypyridin-3-yl)phenyl]-3-hydroxypentanoic acid (Compound No. 175)
Mass (m/z): 526.91 (M$^+$+1);

(2S,3R)-3-hydroxy-5-[4-(1-methyl-1H-pyrazol-4-yl)-2-thienyl]-2-[2-(4-oxo-1,2,3-benzotriazin-3(4H)-yl)ethyl]pentanoic acid (Compound No. 176);

(2S,3R)-5-[2-fluoro-4-(6-methoxypyridin-3-yl)phenyl]-3-hydroxy-2-[2-(6-methoxy-4-oxo-1,2,3-benzotriazin-3(4H)-yl)ethyl]pentanoic acid (Compound No. 177)
Mass (m/z): 523.01 (M$^+$+1);

(2S,3R)-3-hydroxy-5-(6'-methoxy-2,3'-bipyridin-5-yl)-2-[2-(6-methoxy-4-oxo-1,2,3-benzotriazin-3(4H)-yl)ethyl]pentanoic acid (Compound No. 178);

(2S,3R)-3-hydroxy-2-[2-(6-methoxy-4-oxo-1,2,3-benzotriazin-3(4H)-yl)ethyl]-5-[4-(6-methylpyridin-3-yl)phenyl]pentanoic acid (Compound No. 179)
Mass (m/z): 489.07 (M$^+$+1);

(2S,3R)-5-[4-(2-chloropyridin-3-yl)phenyl]-3-hydroxy-2-[2-(6-methoxy-4-oxo-1,2,3-benzotriazin-3(4H)-yl)ethyl]pentanoic acid (Compound No. 180)
Mass (m/z): 508.99 (M$^+$+1);

(2S,3R)-2-[2-(6-fluoro-4-oxo-1,2,3-benzotriazin-3(4H)-yl)ethyl]-3-hydroxy-5-[4-(6-methoxypyridin-3-yl)phenyl]pentanoic acid (Compound No. 181)
Mass (m/z): 493.19 (M$^+$+1);

(2S,3R)-5-(4'-chlorobiphenyl-4-yl)-2-[2-(6-fluoro-4-oxo-1,2,3-benzotriazin-3(4H)-yl)ethyl]-3-hydroxypentanoic acid (Compound No. 182)
Mass (m/z): 496.17 (M$^+$+1);

(2S,3R)-5-(3',4'-difluorobiphenyl-4-yl)-2-[2-(6-fluoro-4-oxo-1,2,3-benzotriazin-3(4H)-yl)ethyl]-3-hydroxypentanoic acid (Compound No. 183)
Mass (m/z): 498.15 (M$^+$+1);

(2S,3R)-2-[2-(6-fluoro-4-oxo-1,2,3-benzotriazin-3(4H)-yl)ethyl]-3-hydroxy-5-(4'-methoxybiphenyl-4-yl)pentanoic acid (Compound No. 184)
Mass (m/z): 492.16 (M$^+$+1);

(2S,3R)-3-hydroxy-5-[4-(2-methoxypyrimidin-5-yl)phenyl]-2-[2-(4-oxo-1,2,3-benzotriazin-3(4H)-yl)ethyl]pentanoic acid (Compound No. 185)
Mass (m/z): 476.13 (M$^+$+1);

(2S,3R)-5-[2-fluoro-4-(1-methyl-1H-pyrazol-4-yl)phenyl]-3-hydroxy-2-[2-(6-methyl-4-oxo-1,2,3-benzotriazin-3(4H)-yl)ethyl]pentanoic acid (Compound No. 186)
Mass (m/z): 480.08 (M$^+$+1);

(2S,3R)-5-[2-fluoro-4-(1-methyl-1H-pyrazol-4-yl)phenyl]-3-hydroxy-2-[2-(7-methyl-4-oxo-1,2,3-benzotriazin-3(4H)-yl)ethyl]pentanoic acid (Compound No. 187)
Mass (m/z): 480.15 (M$^+$+1);

(2S,3R)-2-[2-(5-chloro-4-oxo-1,2,3-benzotriazin-3(4H)-yl)ethyl]-5-[2-fluoro-4-(1-methyl-1H-pyrazol-4-yl)phenyl]-3-hydroxypentanoic acid (Cmpound No. 188)
Mass (m/z): 500.07 (M$^+$+1);

(2S,3R)-2-[2-(7-chloro-4-oxo-1,2,3-benzotriazin-3(4H)-yl)ethyl]-5-[2-fluoro-4-(1-methyl-1H-pyrazol-4-yl)phenyl]-3-hydroxypentanoic acid (Compound No. 189)
Mass (m/z): 500.13 (M$^+$+1);

(2S,3R)-5-[2-fluoro-4-(1-methyl-1H-pyrazol-4-yl)phenyl]-2-[2-(5-fluoro-4-oxo-1,2,3-benzotriazin-3(4H)-yl)ethyl]-3-hydroxypentanoic acid (Compound No. 190)
Mass (m/z): 484.15 (M$^+$+1);

(2S,3R)-2-[2-(6,7-difluoro-4-oxo-1,2,3-benzotriazin-3(4H)-yl)ethyl]-5-[2-fluoro-4-(1-methyl-1H-pyrazol-4-yl)phenyl]-3-hydroxypentanoic acid (Compound No. 191)
Mass (m/z): 502.16 (M$^+$+1);

(2S,3R)-5-[2-fluoro-4-(1-methyl-1H-pyrazol-4-yl)phenyl]-2-[2-(6-fluoro-4-oxo-1,2,3-benzotriazin-3(4H)-yl)ethyl]-3-hydroxypentanoic acid (Compound No. 192;
Mass (m/z): 507.22 (M$^+$+23);

(2S,3R)-5-[2-fluoro-4-(1-methyl-1H-pyrazol-4-yl)phenyl]-3-hydroxy-2-[2-(8-methyl-4-oxo-1,2,3-benzotriazin-3(4H)-yl)ethyl]pentanoic acid (Compound No. 193);

(2S,3R)-3-hydroxy-2-[2-(6-methoxy-4-oxo-1,2,3-benzotriazin-3(4H)-yl)ethyl]-5-[4-(2-methoxypyrimidin-5-yl)phenyl]pentanoic acid (Compound No. 194)
Mass (m/z): 506.12 (M$^+$+1);

(2S,3R)-2-[2-(1,3-dioxo-1,3-dihydro-2H-isoindol-2-yl)ethyl]-3-hydroxy-5-[4-(2-methoxypyrimidin-5-yl)phenyl]pentanoic acid (Compound No. 195)
Mass (m/z): 476.18 (M$^+$+1);

(2S,3R)-5-[2-fluoro-4-(1-methyl-1H-pyrazol-4-yl)phenyl]-3-hydroxy-2-[2-(1-oxophthalazin-2(1H)-yl)ethyl]pentanoic acid (Compound No. 196)
Mass (m/z): 465.26 (M$^+$+1);

(2S,3R)-5-[2-fluoro-4-(1-methyl-1H-pyrazol-4-yl)phenyl]-3-hydroxy-2-[2-(3-methyl-2,6-dioxo-3,6-dihydropyrimidin-1(2H)-yl)ethyl]pentanoic acid (Compound No. 197)
Mass (m/z): 445.25 (M$^+$+1);

(2S,3R)-3-hydroxy-5-[4-(6-methoxypyridin-3-yl)phenyl]-2-{2-[4-oxo-7-(trifluoromethyl)-1,2,3-benzotriazin-3(4H)-yl]ethyl}pentanoic acid (Compound No. 198)
Mass (m/z): 543.22 (M$^+$+1);

(2S,3R)-3-hydroxy-5-[4-(6-methoxypyridin-3-yl)phenyl]-2-[2-(1-oxophthalazin-2(1H)-yl)ethyl]pentanoic acid (Compound No. 199)
Mass (m/z): 474.25 (M$^+$+1);

(2S,3R)-3-hydroxy-5-[4-(6-methoxypyridin-3-yl)phenyl]-2-[2-(3-methyl-2,6-dioxo-3,6-dihydropyrimidin-1(2H)-yl)ethyl]pentanoic acid (Compound No. 200)
Mass (m/z): 454.24 (M$^+$+1);

(2S,3R)-2-[2-(7,9-dioxo-8-azaspiro[4.5]dec-8-yl)ethyl]-3-hydroxy-5-[4-(6-methoxypyridin-3-yl)phenyl]pentanoic acid (Compound No. 201)
Mass (m/z): 495.27 (M$^+$+1);

(2S,3R)-2-[2-(2,4-dioxo-2H-1,3-benzoxazin-3(4H)-yl)ethyl]-3-hydroxy-5-[4-(6-methoxypyridin-3-yl)phenyl]pentanoic acid (Compound No. 202)
Mass (m/z): 491.17 (M$^+$+1);

(2S,3R)-3-hydroxy-5-[4-(6-methoxypyridin-3-yl)phenyl]-2-[2-(3,4,4-trimethyl-2,5-dioxoimidazolidin-1-yl)ethyl]pentanoic acid (Compound No. 203)
Mass (m/z): 470.12 (M$^+$+1);

(2S,3R)-5-(4-chloro-3-fluorophenyl)-2-[2-(1,3-dioxo-1,3-dihydro-2H-isoindol-2-yl)ethyl]-3-hydroxypentanoic acid (Compound No. 204)
Mass (m/z): 420.06 (M$^+$+1);

(2R,3S)-2-[2-(1,3-dioxo-1,3-dihydro-2H-isoindol-2-yl)ethyl]-5-(3'-fluoro-4'-methylbiphenyl-4-yl)-3-hydroxypentanoic acid (Compound No. 205)
Mass (m/z): 476.07 (M$^+$+1);

(2R,3S)-2-[2-(1,3-dioxo-1,3-dihydro-2H-isoindol-2-yl)ethyl]-5-(4'-fluorobiphenyl-4-yl)-3-hydroxypentanoic acid (Compound No. 206)
Mass (m/z): 462.03 (M$^+$+1);

(2R,3S)-5-(3',4'-difluorobiphenyl-4-yl)-2-[2-(1,3-dioxo-1,3-dihydro-2H-isoindol-2-yl)ethyl]-3-hydroxypentanoic acid (Compound No. 207)
Mass (m/z): 480.03 (M$^+$+1);

(2S,3S)-3-hydroxy-5-(4'-methoxybiphenyl-4-yl)-2-[2-(4-oxo-1,2,3-benzotriazin-3(4H)-yl)ethyl]pentanoic acid (Compound No. 208)
Mass (m/z): 474.31 (M$^+$+1);

(2S,3R)-3-hydroxy-5-[4-(5-methylpyridin-2-yl)phenyl]-2-[2-(4-oxo-1,2,3-benzotriazin-3(4H)-yl)ethyl]pentanoic acid (Compound No. 209)
Mass (m/z): 459.21 (M$^+$+1);

(2S,3R)-5-[4-(6-fluoropyridin-3-yl)phenyl]-3-hydroxy-2-[2-(4-oxo-1,2,3-benzotriazin-3(4H)-yl)ethyl]pentanoic acid (Compound No. 210)
Mass (m/z): 463.17 (M$^+$+1);

(2S,3R)-2-[2-(5-fluoro-4-oxo-1,2,3-benzotriazin-3(4H)-yl)ethyl]-3-hydroxy-5-[4'-(trifluoromethyl)biphenyl-4-yl]pentanoic acid (Compound No. 211)
Mass (m/z): 530.33 (M$^+$+1);
(2S,3R)-5-(4'-chlorobiphenyl-4-yl)-3-hydroxy-2-[2-(7-methyl-4-oxo-1,2,3-benzotriazin-3(4H)-yl)ethyl]pentanoic acid (Compound No. 212)
Mass (m/z): 492.29 (M$^+$+1);
(2S,3R)-3-hydroxy-5-(6'-methoxy-2,3'-bipyridin-5-yl)-2-[2-(8-methyl-4-oxo-1,2,3-benzotriazin-3(4H)-yl)ethyl]pentanoic acid (Compound No. 213)
Mass (m/z): 490.34 (M$^+$+1);
(2S,3R)-5-(3'-fluoro-4'-methylbiphenyl-4-yl)-3-hydroxy-2-[(4-oxo-1,2,3-benzotriazin-3(4H)-yl)methyl]pentanoic acid (Compound No. 214);
(2S,3R)-3-hydroxy-2-[(4-oxo-1,2,3-benzotriazin-3(4H)-yl)methyl]-5-[4'-(trifluoromethyl)biphenyl-4-yl]pentanoic acid (Compound No. 215)
Mass (m/z): 498.09 (M$^+$+1);
(2S,3R)-5-(2',4'-difluorobiphenyl-4-yl)-3-hydroxy-2-[(4-oxo-1,2,3-benzotriazin-3(4H)-yl)methyl]pentanoic acid (Compound No. 216)
Mass (m/z): 466.06 (M$^+$+1);
(2S,3R)-5-(4'-fluorobiphenyl-4-yl)-3-hydroxy-2-[(4-oxo-1,2,3-benzotriazin-3(4H)-yl)methyl]pentanoic acid (Compound No. 217)
Mass (m/z): 448.07 (M$^+$+1);
(2S,3R)-5-(3'-fluoro-4'-methoxybiphenyl-4-yl)-3-hydroxy-2-[(4-oxo-1,2,3-benzotriazin-3(4H)-yl)methyl]pentanoic acid (Compound No. 218)
Mass (m/z): 478.22 (M$^+$+1);
(2S,3R)-3-hydroxy-5-[4-(2-methoxypyrimidin-5-yl)phenyl]-2-[(4-oxo-1,2,3-benzotriazin-3(4H)-yl)methyl]pentanoic acid (Compound No. 219)
Mass (m/z): 462.23 (M$^+$+1);
(2S,3R)-3-hydroxy-5-[4-(6-methoxypyridin-3-yl)phenyl]-2-[(4-oxo-1,2,3-benzotriazin-3(4H)-yl)methyl]pentanoic acid (Compound No. 220)
Mass (m/z): 461.23 (M$^+$+1)
(2S,3R)-3-hydroxy-5-(4'-methylbiphenyl-4-yl)-2-[(4-oxo-1,2,3-benzotriazin-3(4H)-yl)methyl]pentanoic acid (Compound No. 221)
Mass (m/z): 444.24 (M$^+$+1);
(2S,3R)-3-hydroxy-2-[(4-oxo-1,2,3-benzotriazin-3(4H)-yl)methyl]-5-[4'-(trifluoromethoxy)biphenyl-4-yl]pentanoic acid (Compound No. 222)
Mass (m/z): 514.14 (M$^+$+1);
(2S,3R)-3-hydroxy-5-[4-(6-methylpyridin-3-yl)phenyl]-2-[(4-oxo-1,2,3-benzotriazin-3(4H)-yl)methyl]pentanoic acid (Compound No. 223)
Mass (m/z): 445.18 (M$^+$+1);
(2S,3R)-5-(4'-chlorobiphenyl-4-yl)-3-hydroxy-2-[(4-oxo-1,2,3-benzotriazin-3(4H)-yl)methyl]pentanoic acid (Compound No. 224)
Mass (m/z): 464.18 (M$^+$+1);
(2S,3R)-5-(3',4'-difluorobiphenyl-4-yl)-3-hydroxy-2-[(4-oxo-1,2,3-benzotriazin-3(4H)-yl)methyl]pentanoic acid (Compound No. 225)
Mass (m/z): 466.20 (M$^+$+1);
(2S,3R)-3-hydroxy-5-[4-(6-hydroxypyridin-3-yl)phenyl]-2-[2-(4-oxo-1,2,3-benzotriazin-3(4H)-yl)ethyl]pentanoic acid (Compound No. 226)
Mass (m/z): 461.23 (M$^+$+1);
(2S,3R)-3-hydroxy-5-(4'-methylbiphenyl-4-yl)-2-{2-[4-oxo-7-(trifluoromethyl)-1,2,3-benzotriazin-3(4H)-yl]ethyl}pentanoic acid (Compound No. 227)
Mass (m/z): 526.16 (M$^+$+1);
(2S,3R)-2-[2-(2,4-dioxo-1,4-dihydroquinazolin-3(2H)-yl)ethyl]-3-hydroxy-5-[4-(6-methoxypyridin-3-yl)phenyl]pentanoic acid (Compound No. 228)
Mass (m/z): 490.17 (M$^+$+1);
(2S,3R)-3-(acetyloxy)-5-[4-(6-methoxypyridin-3-yl)phenyl]-2-[2-(4-oxo-1,2,3-benzotriazin-3(4H)-yl)ethyl]pentanoic acid (Compound No. 229)
Mass (m/z): 517.06 (M$^+$+1);
(2S,3R)-2-[2-(8-chloro-4-oxo-1,2,3-benzotriazin-3(4H)-yl)ethyl]-3-hydroxy-5-[4-(6-methoxypyridin-3-yl)phenyl]pentanoic acid (Compound No. 230)
Mass (m/z): 509.17 (M$^+$+1);
(2S,3R)-5-(4'-chlorobiphenyl-4-yl)-2-[2-(2,4-dioxo-2H-1,3-benzoxazin-3(4H)-yl)ethyl]-3-hydroxypentanoic acid (Compound No. 231)
Mass (m/z): 493.93 (M$^+$+1); and
(2S,3R)-5-(4'-chlorobiphenyl-4-yl)-3-hydroxy-2-(2-{[(2-hydroxyphenyl)carbonyl]amino}ethyl)pentanoic acid (Compound No. 232)
Mass (m/z): 468.14 (M$^+$+1).

Example

Assay for Matrix Metalloproteinases (MMPs)

New chemical entities of the present invention and corresponding standards used in the present invention were prepared (stock 10 mM) in 100% DMSO and subsequent dilutions were made in 50% DMSO-50% TCNB (50 mM Tris, 10 mM CaCl$_2$, 150 mM NaCl, 0.05% Brij-35, pH 7.5). 1 µl of the compound and 88 µl of TCNB was added to the wells of a 96 well plate to achieve the desired final concentration of NCE (final DMSO concentration should not exceed 0.5%). 1 µl of activated, recombinant MMPs was added to each well (20-100 mg/100 µl reaction mixture) except the "negative well". (MMP-1, 9, and 14 enzymes require prior activation. For this, the supplied enzyme was incubated with either APMA, final concentration 1 mM, for a time period of 1 hour at 37° C.). Incubation was done at room temperature for 4 to 5 minutes. Reaction was initiated with 10 µl of 100 µM substrate (ES001: Aliquots were freshly diluted in TCNB; stock: 2 mM) and increase in florescence was monitored at excitation wavelength 320 nm followed by emission at 405 nm for 25 to 30 cycles. Increase in florescence (RFU) was calculated for positive, negative, and NCE/standard wells. The percent inhibition compared to controls was calculated and IC$_{50}$ values were determined using Graph-prism software.

The present invention relates to compounds that act as dual MMP-9/12 inhibitors, which have desirable activity profiles and beneficial potency, selectivity, and/or pharmacokinetic properties.

In particular, compounds disclosed herein exhibited activity in MMP-9 assays from ≤0.02 nM to about 40 µM, or from ≤0.02 nM to about 200 nM, or from ≤0.02 nM to about 20 nM, or from ≤0.02 nM to about 1.0 nM, or from ≤0.02 nM to about 0.3 nM. Compounds disclosed herein exhibited activity in MMP-12 assays from ≤0.02 nM to about 3.8 µM, or from ≤0.02 nM to about 200 nM, or from ≤0.02 nM to about 20 nM, or from ≤0.02 nM to about 1.0 nM, or from ≤0.02 nM to about 0.3 nM. Particular compounds tested (Nos. 2-28, 30, 32-43, 46, 50-51, 55-58, 60-61, 63, 65-69, 76, 79-80, 86-89, 93-96, 98, 106-107, 113-122, 126, 130-132, 134, 136-138, 143-144, 148-150, 155, 157, 159, 173-175, 177, 179, 181-182, 184-186, 190, 192-195, 198, and 210-211) exhibited activity in MMP-1 assays from about 100 nM to about 10 µM, for example, from about 100 nM to about 5 µM, or from about 100 nM to about 2 µM, or from about 100 nM to about 1.04 indicating that compounds of the present invention can be selective over MMP-1 by ≥100 fold.

Assay for In Vivo LPS Induced Rat Neutrophilia Model

Male wistar rats were treated with vehicle/NCEs (new chemical entities) or standard drug and 2 hours later challenged with lipopolysaccharide (LPS) in phosphate buffered saline (PBS), by oro-intra tracheal route (400 μL of 50 μg/mL). Negative control animals received PBS alone. Intratracheal instillation was done under ketamine and xylazine anaesthesia. Two hours post-LPS challenge, the rats were euthanised and bronchoalveolar lavage (BAL) was performed. The TLC, DLC was done to enumerate neutrophil count in the BAL fluid and results were expressed as percent inhibition using the following formula $$\frac{NeuLPS - NeuTEST}{NeuLPS - NeuPBS} \times 100$$

Where,

NeuLPS=Neutrophil count in vehicle-treated LPS challenged group

NeuTEST=Neutrophil count in group treated with a given dose of test compound

NeuPBS=Neutrophil in vehicle-treated group challenged with PBS

Solubility Assessment

Equilibrium Solubility:

The pH-solubility profile of a compound is determined at 37° C. in aqueous media with a pH in the range of 1-7.5. A sufficient number of pH conditions are evaluated to accurately define the pH-solubility profile. Standard buffer solutions described in the USP are considered appropriate for use in solubility studies.

The compound is weighed and transferred to the flasks. Media are added to each conical flask, and the flask is sealed with a stopper and paraffin film. The volume added is dependant upon the volume required for analysis of the content of the compound. The pH of the solution is measured after addition of the compound. The flask is observed intermittently. If the drug substance is completely dissolved, additional amounts of the compound are added until saturation (undissolved residue) is observed and the pH is measured. Flasks are removed from the water bath after equilibrium is achieved. The saturated solution is filtered through 0.45 μm membrane filter and the samples are analyzed to estimate the content of the test compound.

Pharmacokinetic Screening Assays for Matrix Metalloproteinase (MMP 9/12) Inhibitors Intrinsic Clearance:

Intrinsic clearance (or metabolism stability) is assessed by estimating the rate of initial decay of the parent compound in a suitable biological matrix, like human liver microsomes.

The study reaction consists of NADPH regeneration system and liver microsomes of the various species of interest (human, rat, dog, mouse) added into buffer at a concentration of 0.5 mg/mL. After a short preincubation, the metabolic reaction is initiated by the addition of 5 μL of the substrate stock (100 μM) to yield a final concentration of 0.5 μM in the reaction. Periodic aliquots are drawn every three minutes for 30 minutes, quenched, and the test compound concentration is estimated by LCMS. The rate of disappearance is estimated as the first order slope of the % of parent remaining vs. time graph. The rate of decay is normalized to the unit concentration of the test compound and protein and extrapolated to 1 g of liver by using scaling factors (52.5 mg of CYP microsomal protein per gram of liver).

In Vitro Glucuronidation:

A comparative assay in the form of intrinsic clearance (see above) with the addition of glucuronic acid and alamethacin to compare primarily the parent disappearance due to glucuronidation. Expressed as rate of clearance and normalized to per gram of liver.

Plasma Protein Binding:

Assessment by the equilibrium dialysis method where the unbound compound diffuses across a semi-permeable membrane and equilibrates with phosphate buffer (pH 7.4) is estimated, and is subtracted from the total drug in plasma to determine the percentage bound.

Equilibrium dialysis membranes are soaked overnight and the assembly is prepared. The test drug is spiked into plasma (100 and 1000 ng/mL) and incubated at 37° C. and is transferred into the equilibrium apparatus with plasma added in one compartment and buffer added in the other. The unit is rotated at constant rpm at 37° C. for four hours to allow the unbound compound to dialyse and distribute within the buffer chamber. After four hours the plasma and the buffer are removed from the respective compartments and the test compound concentrations are estimated. The percentage bound is estimated from the test compound concentrations.

Alternate methods include the ultra filtration method where the compound spiked in plasma (100 and 1000 ng/mL) is filtered with Centricon® filters having molecular weight cut off of 30,000 DA to prepare the retentate and ultra filtrate. The test compound is estimated in both and the percentage bound is calculated.

We claim:

1. A compound which is selected from:
 (2S,3R)-2-[2-(5-chloro-4-oxo-1,2,3-benzotriazin-3(4H)-yl)ethyl]-3-hydroxy-5-(6'-methoxy-2,3'-bipyridin-5-yl)pentanoic acid (Compound No. 121);
 (2S,3R)-2-[2-(7-chloro-4-oxo-1,2,3-benzotriazin-3(4H)-yl)ethyl]-3-hydroxy-5-(6'-methoxy-2,3'-bipyridin-5-yl)pentanoic acid (Compound No. 122);
 (2S,3R)-2-[2-(6,7-difluoro-4-oxo-1,2,3-benzotriazin-3(4H)-yl)ethyl]-3-hydroxy-5-(6'-methoxy-2,3'-bipyridin-5-yl)pentanoic acid (Compound No. 123);
 (2S,3R)-2-[2-(5-fluoro-4-oxo-1,2,3-benzotriazin-3(4H)-yl)ethyl]-3-hydroxy-5-(6'-methoxy-2,3'-bipyridin-5-yl)pentanoic acid (Compound No. 126);
 (2S,3R)-2-[2-(7-chloro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 130);
 (2S,3R)-2-[2-(6,7-difluoro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 131);
 (2S,3R)-2-[2-(5-chloro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 132);
 (2S,3R)-3-hydroxy-2-[2-(7-methyl-4-oxo-1,2,3-benzotriazin-3(4H)-yl)ethyl]-5-{6-[4-(trifluoromethyl)phenyl]pyridin-3-yl}pentanoic acid (Compound No. 133);
 (2S,3R)-2-[2-(5-fluoro-4-oxo-1,2,3-benzotriazin-3(4H)-yl)ethyl]-3-hydroxy-5-{6-[4-(trifluoromethyl)phenyl]pyridin-3-yl}pentanoic acid (Compound No. 134);
 (2S,3R)-3-hydroxy-5-(6'-methoxy-2,3'-bipyridin-5-yl)-2-[2-(4-oxo-1,2,3-benzotriazin-3(4H)-yl)ethyl]pentanoic acid (Compound No. 140);

(2S,3R)-3-hydroxy-5-(6'-methoxy-2,3'-bipyridin-5-yl)-2-[2-(6-methyl-4-oxo-1,2,3-benzotriazin-3(4H)-yl)ethyl]pentanoic acid (Compound No. 141);

(2S,3R)-3-hydroxy-5-(6'-methoxy-2,3'-bipyridin-5-yl)-2-[2-(7-methyl-4-oxo-1,2,3-benzotriazin-3(4H)-yl)ethyl]pentanoic acid (Compound No. 142);

(2S,3R)-3-hydroxy-5-[4-(1-methyl-1H-pyrazol-4-yl)-2-thienyl]-2-[2-(4-oxo-1,2,3-benzotriazin-3(4H)-yl)ethyl]pentanoic acid (Compound No. 176);

(2S,3R)-3-hydroxy-5-(6'-methoxy-2,3'-bipyridin-5-yl)-2-[2-(6-methoxy-4-oxo-1,2,3-benzotriazin-3(4H)-yl)ethyl]pentanoic acid (Compound No. 178); and (2S,3R)-3-hydroxy-5-(6'-methoxy-2,3'-bipyridin-5-yl)-2-[2-(8-methyl-4-oxo-1,2,3-benzotriazin-3(4H)-yl)ethyl]pentanoic acid (Compound No. 213).

2. A pharmaceutical composition comprising a therapeutically effective amount of a compound of claim 1, together with pharmaceutically acceptable carriers, excipients, or diluents.

3. The pharmaceutical composition of claim 2 further comprising one or more additional active ingredients selected from the group consisting of:

a. Anti-inflammatory agents, selected from (i) the nonsteroidal anti-inflammatory agents piroxicam, diclofenac, propionic acids, fenamates, pyrazolones, salicylates, PDE-4/p38 MAP Kinase/Cathepsin inhibitors, CCR-3 antagonists, iNOS inhibitors, tryptase and elastase inhibitors, beta-2 integrin antagonists, cell adhesion inhibitors, and adenosine 2a agonists; (ii) leukotrienes LTC4/LTD4/LTE4/LTB4-Inhibitors, 5-lipoxygenase inhibitors, and PAF-receptor antagonists; (iii) Cox-2 inhibitors; (iv) other MMP inhibitors; (v) interleukin-1 inhibitors; (vi) the corticosteroids alclometasone, amcinonide, amelometasone, beclometasone, betamethasone, budesonide, ciclesonide, clobetasol, cloticasone, cyclomethasone, deflazacort, deprodone, dexbudesonide, diflorasone, difluprednate, fluticasone, flunisolide, halometasone, halopredone, hydrocortisone, methylprednisolone, mometasone, prednicarbate, prednisolone, rimexolone, tixocortol, triamcinolone, ulobetasol, rofleponide, GW 215864, KSR 592, ST-126, dexamethasone, and pharmaceutically acceptable salts or solvates thereof;

b) Beta-agonists, selected from β2-agonists albuterol, salbutamol, biltolterol, pirbuterol, levosalbutamol, tulobuterol, terbutaline, bambuterol, metaproterenol, fenoterol, salmeterol, carmoterol, arformoterol, formoterol, and pharmaceutically acceptable salts or solvates thereof;

c) antihypertensive agents selected from (i) ACE inhibitors enalapril, lisinopril, valsartan, Telmisartan, and quinapril; (ii) angiotensin II receptor antagonists and agonists losartan, candesartan, irbesartan, valsartan, and eprosartan; (iii) β-blockers; and (iv) calcium channel blockers;

d) immunosuppressive agents selected from cyclosporine, azathioprine, and methotrexate; anti-inflammatory corticosteroids; and e) antiinfective agents consisting of antibiotics and antiviral.

* * * * *